(12) United States Patent  (10) Patent No.: US 7,591,949 B2
Cevc et al.  (45) Date of Patent: *Sep. 22, 2009

(54) METHOD FOR THE IMPROVEMENT OF TRANSPORT ACROSS ADAPTABLE SEMI-PERMEABLE BARRIERS

(75) Inventors: Gregor Cevc, Gauting (DE); Holger Richardsen, München (DE); Andrea Weiland-Waibel, Hohenbrunn (DE)

(73) Assignee: IDEA AG, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/984,450

(22) Filed: Nov. 8, 2004

(65) Prior Publication Data

US 2005/0123897 A1 Jun. 9, 2005

Related U.S. Application Data

(63) Continuation of application No. 10/037,480, filed on Jan. 4, 2002, and a continuation of application No. PCT/EP00/06367, filed on Jul. 5, 2000, which is a continuation of application No. PCT/EP99/04659, filed on Jul. 5, 1999.

(51) Int. Cl.
*B01D 61/00* (2006.01)
*A61K 9/127* (2006.01)

(52) U.S. Cl. ............... 210/645; 210/650; 424/450; 424/94.3; 424/96.3

(58) Field of Classification Search ............ 210/645, 210/767, 650; 424/450, 94.3, 9, 484, 321, 424/9.51, 96.3; 436/829; 935/54; 428/402.2; 514/772.6; 426/829

See application file for complete search history.

(56) References Cited

U.S. PATENT DOCUMENTS 4,369,182 A  1/1983  Ghyczy et al.

(Continued)

FOREIGN PATENT DOCUMENTS

AU  1740283  7/1983

(Continued)

OTHER PUBLICATIONS

Prof. Dr. K-U Benner, "Der Korper des Menschen", p. 49 (1995).

(Continued)

*Primary Examiner*—Ana Fortuna
(74) *Attorney, Agent, or Firm*—Wilson Sonsini Goodrich & Rosati PC

(57) ABSTRACT

The invention relates to a method, a kit and a device for controlling the flux of penetrants across an adaptable semi-permeable porous barrier, the method comprising the steps of: preparing a formulation by suspending or dispersing said penetrants in a polar liquid in the form of fluid droplets surrounded by a membrane-like coating of one or several layers, said coating comprising at least two kinds of forms of amphiphilic substances with a tendency to aggregate, said penetrants being able to transport agents through the pores of said barrier or to enable agent permeation through the pores of said barrier after penetrants have entered the pores, selecting a dose amount of said penetrants to be applied on a predetermined area of said barrier to control the flux of said penetrants across said barrier, and applying the selected dose amount of said formulation containing said penetrants onto said area of said porous barrier.

102 Claims, 14 Drawing

U.S. PATENT DOCUMENTS

| | | | |
|---|---|---|---|
| 4,619,794 A | 10/1986 | Hauser | 264/4.1 |
| 4,666,747 A * | 5/1987 | Quinn | 427/4 |
| 4,731,210 A | 3/1988 | Weder et al. | |
| 4,746,509 A | 5/1988 | Haggiage et al. | 424/449 |
| 4,783,450 A | 11/1988 | Fawzi et al. | 514/78 |
| 4,849,224 A | 7/1989 | Chang et al. | |
| 4,897,269 A | 1/1990 | Mezei | |
| 4,911,928 A | 3/1990 | Wallach | |
| 4,921,706 A | 5/1990 | Roberts et al. | |
| 4,937,078 A | 6/1990 | Mezei et al. | |
| 4,937,182 A | 6/1990 | Hancock et al. | |
| 4,937,254 A | 6/1990 | Sheffield et al. | |
| RE33,273 E | 7/1990 | Speaker | |
| 4,944,948 A | 7/1990 | Uster et al. | 424/450 |
| 4,954,345 A | 9/1990 | Miller | |
| 4,983,395 A | 1/1991 | Chang et al. | |
| 5,043,165 A | 8/1991 | Radhakrishnan | |
| 5,104,661 A * | 4/1992 | Lau | 424/450 |
| 5,145,684 A | 9/1992 | Liversidge et al. | 424/489 |
| 5,154,930 A | 10/1992 | Popescu et al. | 424/489 |
| 5,202,125 A | 4/1993 | Ebert et al. | |
| 5,209,720 A | 5/1993 | Unger | |
| 5,238,613 A | 8/1993 | Anderson | |
| 5,244,678 A | 9/1993 | Legros et al. | |
| 5,322,685 A | 6/1994 | Nakagawa et al. | 424/78.03 |
| 5,460,820 A | 10/1995 | Ebert et al. | |
| 5,498,418 A | 3/1996 | Beutner et al. | |
| 5,498,420 A | 3/1996 | Mentrup Edgar et al. | |
| 5,510,118 A | 4/1996 | Bosch et al. | 424/489 |
| 5,552,160 A | 9/1996 | Liversidge et al. | 424/489 |
| 5,585,109 A | 12/1996 | Hayward et al. | |
| 5,607,692 A | 3/1997 | Ribier et al. | 424/450 |
| 5,614,178 A | 3/1997 | Bloom et al. | |
| 5,648,095 A | 7/1997 | Illum et al. | |
| 5,654,337 A | 8/1997 | Roentsch et al. | 514/570 |
| 5,681,849 A | 10/1997 | Richter et al. | |
| 5,716,638 A | 2/1998 | Touitou | 424/450 |
| 5,741,515 A | 4/1998 | Ciceri et al. | 424/450 |
| 5,763,422 A | 6/1998 | Lichtenberger et al. | |
| 5,783,208 A | 7/1998 | Venkateshwaran et al. | |
| 5,837,289 A * | 11/1998 | Grasela et al. | 424/484 |
| 5,858,330 A | 1/1999 | Boltri et al. | 424/45 |
| 5,874,095 A | 2/1999 | Deckner et al. | |
| 5,874,422 A | 2/1999 | Krause et al. | 514/165 |
| 5,891,472 A * | 4/1999 | Russell | 424/484 |
| 5,958,379 A | 9/1999 | Regenold et al. | 424/47 |
| 5,985,860 A | 11/1999 | Toppo | 514/159 |
| 6,028,066 A | 2/2000 | Unger | |
| 6,045,827 A | 4/2000 | Russell | 424/485 |
| 6,069,172 A | 5/2000 | Bertini et al. | 514/570 |
| 6,083,996 A * | 7/2000 | Buyuktimkin et al. | 514/772.6 |
| 6,165,500 A | 12/2000 | Cevc | 424/450 |
| 6,193,996 B1 | 2/2001 | Effing et al. | |
| 6,200,598 B1 | 3/2001 | Needham | |
| 6,214,386 B1 | 4/2001 | Santus et al. | 424/498 |
| 6,248,353 B1 | 6/2001 | Singh | |
| 6,277,892 B1 | 8/2001 | Deckner et al. | |
| 6,294,192 B1 | 9/2001 | Patel et al. | 424/451 |
| 6,303,141 B1 | 10/2001 | Fischer et al. | |
| 6,387,383 B1 | 5/2002 | Dow et al. | 424/401 |
| 6,448,296 B2 | 9/2002 | Yasueda et al. | 514/781 |
| 6,451,339 B2 | 9/2002 | Patel et al. | 424/451 |
| 6,517,864 B1 | 2/2003 | Jacobsen et al. | |
| 6,562,370 B2 | 5/2003 | Luo et al. | |
| 6,577,880 B1 * | 6/2003 | Ishida et al. | 455/562.1 |
| 6,582,724 B2 | 6/2003 | Hsu et al. | |
| 6,586,000 B2 | 7/2003 | Luo et al. | |
| 6,645,520 B2 | 11/2003 | Hsu et al. | |
| 6,645,529 B2 | 11/2003 | Gergely et al. | |
| 6,654,337 B2 | 11/2003 | Roentsch et al. | |
| 6,726,598 B1 | 4/2004 | Jarvis et al. | |
| 6,797,276 B1 * | 9/2004 | Glenn et al. | 424/278.1 |
| 6,835,392 B2 | 12/2004 | Hsu et al. | |
| 6,868,686 B2 * | 3/2005 | Ueda et al. | 62/228.4 |
| 7,063,859 B1 | 6/2006 | Kanios et al. | |
| 7,175,850 B2 | 2/2007 | Cevc | |
| 7,387,788 B1 | 6/2008 | Carrara et al. | |
| 7,459,171 B2 | 12/2008 | Cevc et al. | |
| 7,473,432 B2 | 1/2009 | Cevc et al. | |
| 2001/0012849 A1 | 8/2001 | Wechter | 514/330 |
| 2002/0003179 A1 | 1/2002 | Verhoff et al. | 241/21 |
| 2002/0012680 A1 | 1/2002 | Patel et al. | 424/400 |
| 2002/0037877 A1 | 3/2002 | Singh | 514/78 |
| 2002/0048596 A1 | 4/2002 | Cevc | |
| 2002/0106345 A1 | 8/2002 | Uhrich et al. | |
| 2002/0119188 A1 | 8/2002 | Niemiec et al. | 424/450 |
| 2002/0147238 A1 | 10/2002 | Jerussi et al. | 514/570 |
| 2003/0099694 A1 | 5/2003 | Cevc et al. | |
| 2004/0071767 A1 | 4/2004 | Cevc et al. | |
| 2005/0123897 A1 | 6/2005 | Cevc et al. | |
| 2007/0031483 A1 | 2/2007 | Cevc | |
| 2007/0042030 A1 | 2/2007 | Cevc | |
| 2007/0184114 A1 | 8/2007 | Cevc | |
| 2007/0243203 A1 | 10/2007 | Abrecht et al. | |

FOREIGN PATENT DOCUMENTS

| | | |
|---|---|---|
| AU | 724218 | 5/1998 |
| CA | 1 143 656 | 3/1983 |
| CA | 1289420 | 9/1991 |
| CA | 2 067 754 | 3/1992 |
| CA | 2052164 | 9/1992 |
| CA | 2160775 | 11/1994 |
| DE | 3016976 | 11/1980 |
| DE | 3713494 | 10/1987 |
| DE | P 40 26 833.0-43 | 2/1992 |
| DE | P 40 26 834.9-41 | 2/1992 |
| DE | 4107152 | 9/1992 |
| DE | 4107153 | 9/1992 |
| DE | 44 47 287 | 12/1994 |
| DE | 4447287 | 11/1996 |
| EP | 0 088 046 | 9/1983 |
| EP | 0102 324 | 3/1984 |
| EP | 0102324 | 3/1984 |
| EP | 0152379 A2 | 2/1985 |
| EP | 0 152 379 | 8/1985 |
| EP | 0224837 | 11/1986 |
| EP | 0211647 | 2/1987 |
| EP | 0220797 | 5/1987 |
| EP | 0280492 | 8/1988 |
| EP | 0 298 280 | 1/1989 |
| EP | 0 393 707 | 4/1990 |
| EP | 0475160 A1 * | 5/1991 |
| EP | 0 475 160 | 8/1991 |
| EP | 0475160 | 3/1992 |
| EP | 0 355 095 | 8/1993 |
| EP | 0582239 | 2/1994 |
| EP | 0674913 | 4/1995 |
| EP | 0704206 | 4/1996 |
| EP | 0707847 | 4/1996 |
| EP | 0 382 716 | 1/1998 |
| EP | 0382716 | 1/1998 |
| EP | 0 995 435 | 4/2000 |
| EP | 0995435 | 4/2000 |
| EP | 1031347 | 4/2002 |
| EP | 1031346 | 5/2002 |
| EP | 1140021 B1 | 8/2002 |
| EP | 0475160 B2 | 7/2004 |
| HU | 9903363 | 3/2000 |
| HU | 0104424 | 3/2002 |
| HU | 0105400 | 5/2002 |
| JP | 61-271204 | 12/1986 |
| JP | 07-324029 | 12/1995 |
| JP | 2006131597 | 5/2006 |

| WO | WO-87/01938 | 4/1987 |
| WO | WO 87/01938 | 4/1987 |
| WO | WO 88/07362 | 10/1988 |
| WO | WO-88/07362 | 10/1988 |
| WO | WO-90/09385 | 8/1990 |
| WO | WO-90/09782 | 9/1990 |
| WO | WO 90/09782 | 9/1990 |
| WO | WO-90/11065 | 10/1990 |
| WO | WO-91/01146 | 2/1991 |
| WO | WO 91/04013 | 4/1991 |
| WO | WO 92/03122 | 3/1992 |
| WO | WO-92/04009 | 3/1992 |
| WO | WO 92/05771 | 4/1992 |
| WO | WO-92/22292 | 12/1992 |
| WO | WO 92/22292 | 12/1992 |
| WO | WO 93/19736 | 10/1993 |
| WO | WO 93/19737 | 10/1993 |
| WO | WO 94/26257 | 11/1994 |
| WO | WO-94/26257 | 11/1994 |
| WO | WO-95/35095 | 12/1995 |
| WO | WO-96/19205 | 6/1996 |
| WO | WO-96/29999 | 10/1996 |
| WO | WO 96/29999 | 10/1996 |
| WO | WO 98/06750 | 2/1998 |
| WO | WO-98/07414 | 2/1998 |
| WO | WO-98/17255 | 4/1998 |
| WO | WO 98/17255 | 4/1998 |
| WO | WO-98/24407 | 6/1998 |
| WO | WO 98/30215 | 7/1998 |
| WO | WO 98/33483 | 8/1998 |
| WO | WO-98/33483 | 8/1998 |
| WO | WO 99/22703 | 5/1999 |
| WO | WO-99/22703 | 5/1999 |
| WO | WO-00/00597 | 1/2000 |
| WO | WO 0 0/12060 | 3/2000 |
| WO | WO-00/13684 | 3/2000 |
| WO | WO-00/24377 | 5/2000 |
| WO | WO 00/24377 | 5/2000 |
| WO | WO-00/25822 | 5/2000 |
| WO | WO-00/38653 | 7/2000 |
| WO | WO 00/38653 | 7/2000 |
| WO | WO-00/44349 | 8/2000 |
| WO | WO-00/44350 | 8/2000 |
| WO | WO-00/50007 | 8/2000 |
| WO | WO-01/00247 | 1/2001 |
| WO | WO-01/01962 | 1/2001 |
| WO | WO-01/01963 | 1/2001 |
| WO | WO 01/01963 | 1/2001 |
| WO | WO-02/07767 | 1/2002 |
| WO | WO-02/11683 | 2/2002 |
| WO | WO-02/32398 | 4/2002 |
| WO | WO-02/058670 | 8/2002 |
| WO | WO-2004/032900 | 4/2004 |
| WO | WO-2005/063213 | 7/2005 |
| WO | WO-2006/050926 | 5/2006 |

OTHER PUBLICATIONS

Serva Feinbiochemica, Katalog, pp. 201-202 (1986/1987).
Fluka Chemica-BioChemica, Katalog 16, pp. 204, 830 (1988/1989).
Louis F. Fieser, Mary Fieser, "Organische Chemie", p. 1250 (1968).
J. Roeding, "Visualisierungstechniken von vesikularen Systemen, Wechselwirkungen von Liposomen mit der Haut", Kurs 502 of APV, (May 14-16, 1990).
Hans Schreier, "Liposomen—ein neuartiger Arzneistoffträger", Pharmazie in unserer Zeit, pp. 97-108 (1982).
D. Lichtenberg, "Solubilization of Phospholipids by Detergents Structural and Kinetic Aspects", Biochimica et Biophysica Acta, pp. 285-304 (1983).
Reviews on Biomembranes, Biochimica et Biophysica Acta, vol. 415 No. 1, pp. 29-79 (1975).
M. L. Jackson, et al., Solubilization of Phospatidylcholine Bilayers by Octyl Glucoside, Biochemistry, vol. 21, pp. 4576-4582 (1982).
P. K. Vinson, et al., "Vesicle-micelle transition of phosphatidylcholine and octyl glucoside elucidated by cryo-transmission electron microscopy", Biophysical Journal, vol. 56, pp. 669-681 (1989).
K. Edwards, et al., Effects of Triton X-100 on Sonicated Lecithin Vesicles, Langmuir, vol. 5, pp. 473-478 (1989).
A. Brendzel, et al., "Effects of Lipid-Soluble substances on the Thermotropic Properties of Liposome Filtration", Biochimica et Biophysica Acta, vol. 601, pp. 260-270 (1980).
C. Beyer, "Mikroemulsionen", Pharmazie in unserer Seit, pp. 55-60 (1983).
J. Lasch, et al., "Interactions of external lipids (lipid vesicles) with the skin", Journal of Liposome Research, vol. 5, No. 3, pp. 543-569 (1995).
M. Berger, "Oral Insulin 1922-1992: The History of Continuous Ambition and Failure".
G. Cevc, et al., "The skin: a pathway for systemic treatment with patches and lipid-base agent carriers", Adv. Drug Delivery Reviews, vol. 18, pp. 349-378 (1996).
V. M. Knepp, et al., "Controlled drug release from a novel liposomal deliver system. II. Transdermal deliver charateristics", *Journal of Controlled Release*, vol. 12, No. 1, pp. 25-30 (Mar. 1990).
G. Cevc, "Transfersomes-mediated transepidermal delivery improves the regiospecificity and biological activity of corticosteroids in vivo", *Journal of Controlled Release*, vol. 45, No. 37, pp. 211-226 (Apr. 1997).
L. Löbbecke, et al. "Effects Of Short-Chain Alcohols On The Phase Behavior And Interdigitation Of Phosphatidylcholine Bilayer Membranes", Biochimiea et Biophysica Aeta 1237 (1995) 59-69.
R. Singh, et al. "Liposomally Encapsulated Diclofenac For Sonophoresis Induced Systemic Delivery", J. Microencapsulation, 1995, vol. 12, No. 2, 149-154.
A. Calpena, et al., "Influence of the Formulation on the In Vitro Transdermal Penetration of Sodium Diclofenac", Arzneim.-Forsch./Drug Res. 49 (II), 1012-1017 (1999).
I. Stoye, et al., "Transformation of a Liposomal Dispersion Containing Ibuprofen Lysinate and Phospholipids into Mixed Micelles—Physico-chemical Characterization and Influence on Drug Permeation through Excised Human Stratum Corneum," European Journal of Pharmaceutics and Biopharmaceutics 46 (1998) 191-200.
T. Henmi, et al., "Application of an Oily Gel Formed by Hydrogenated Soybean Phgospholipids as a Percutaneous Absorption-Type Ointment Base", Chem. Pharm. Bull. 42(3) 651-655 (1994).
J. Schramlova, et al., "The Effect of an Antiphlogistic Incorporated in Liposomes on Experimentally Induced Inflammation", Folia Biologica (Praha) 43, 195-199 (1997).
M. Foldvari, et al., "Dermal Drug Delivery by Liposome Encapsulation: Clinical and Electron Microscopic Studies", J. Microencapsulation, 1990, vol. 7, No. 4, 479-489.
M. Foldvari, "In Vitro cutaneous and Percutaneous Delivery and in Vivo Efficacy of Tetracaine from Liposomal and Conventional Vehicles", Pharmaceutical Research, vol. 11 No. 11, 1994.
M. Foldvari, "Effect of Vehicle on Topical Liposomal Drug Delivery: Petrolatum Bases", J. Microencapsulation, 1996, vol. 13, No. 5, 589-600.
M.E. Planas, et al., "Noninvasive Percutaneous Induction of Topical Analgesia by a New Type of Drug Carrier, and Prolongation of Local Pain Insensitivity by Anesthetic Liposomes", Anesth Analg 1992; 75 615-621.
H. Peters, et al., "Pharmacodynamics of a Liposomal Preparation for Local Anaesthesia", Arzneim.-Forsch./Drug Res. 45 (II), Nr 12 (1995).
G. Cevc, "Drug Delivery Across the Skin", Exp. Opin. Invest. Drugs (1997) 6(12) 1887-1937.
A. Klibanov et al., *Biochimica et Biophysica Acta.*, 1062:142-148 (1991).
G. Cevc et al., *Journal of Controlled Release*, 36:3-16 (1995).
S. Yuan et al., *Progress in Physiological Science*, 28(2):163-165 (1997).
G. Cevc et al., *Critical Review in Therapeutic Drug Carrier Systems*, 13(3&4):257-388 (1996).

Lasch, J. et al., "Interactions of external lipids (lipids vesicles) with the skin" Journal of Liposome Research 5(3) pp. 543-569 (1995).
Berger, M. "Oral Insulin 1922-1992: The History of Continuous Ambition and Failure" Heinrich-Heine-University, Dusseldorf, Germany.
Cevc. G. et al., "The skin: a pathway for systemic treatment with patches and lipid-based agent carriers" Advanced Drug Delivery Reviews 18 pp. 349-378 (1996).
M.L. Jacks on, et al. "Solubilization of Phosphatidylcholine Bilayers by Octyl Glucoside", biochemistry 1982, 21, 4576-4582.
P. Vinson, et al. "Vesicle-Micelle Transition of Phosphatidylcholine and Octyl Glucoside Elucidated by Cryo-Transmission Ele Tron Microscopy", Biophys. J., Biophysical Society vol. 56 Oct. 1989 669-681.
K. Edwards, et al. "Effects of Triton X-100 on Sonicated Lecithin Vesicles", Langmuir, vol. 5, No. 3, 1989 pp. 473-478.
A. Brendzel, et al., "Effects of Lipid-Soluble Substances on the Thermotropic Properties of Liposome Filtration", Biochimica et Biophysica Acta, 601 (1980) 260-270.
G. Blu me, et al. "Drug-Carrier and Stability Properties of the Long-Lived Lipid Vesicles, Cryptosomes, in Vitro and in Vivo", Journal of Liposome Research, 2(3), 355-368 (1992).
Swenson, E. Scott and William J. Curatolo. "Intestinal permeability enhancement for proteins, peptides and other polar drugs: mechanisms and potential toxicity." Advanced Drug Delivery Reviews, 8:39-92. (1992).
Pending Claims of U.S. Appl. No. 11/634,091 (Unpublished).
Blume, et al., "Drug-Carrier and Stability Properties of the Long-Lived Lipid Vesicles, Cryptosomes, In Vitro and In Vivo," Journal of Liposome Research, 2(3), 355-368 (1992).
Cevc et al.: "Transdermal drug carriers: basic properties, optimization and transfer efficiency in the case of epicutaneously applied peptides," J. Contr. Rel., 36, pp. 3-16, 1995.
Cevc, "Transfersomes, Liposomes, and Other Lipid Suspensions on the Skin: Permeation Enhancement, Vesicle Penetration, and Transdermal Drug Delivery," Crit. Rev. Ther. Drug Carrier Syst., 13 (3&4), pp. 257-388, 1996.
Guia M. Golden et al., "Role of Stratum Corneum Lipid Fluidity Transdermal Drug Flux," on Journal of Pharmaceutical Sciences vol. 76, No. 1, Jan. 1987, American Pharmaceuticals Association, pp. 25-28.
Helenius, et al.: "Solubilization of Membranes by Detergents," Biochimica et Biophysica Acta, 415 (1975) 29-79.
Ito, Yoshimasa et al. "Percutaneous Absorption of Acemetacin from a Membrane Controlled Transdermal System and Prediction of the Disposition of the Drug in Rats." Biol. Pharm. Bull., 16(6):583-588. (1993).
Kilbanov, et al., Activity of amphipathic poly(ethylene glycol) 5000 to prolong the circulation time of liposomes depends on the liposome size and is unfavorable for immunoliposome binding to target, BBA, 1062, pp. 141-148, 1991.
Lasch, J. et al., "Internactions of external lipids (lipids vesicles) with the skin" Journal of Liposome Research 5(3) pp. 543-569 (1995).
Lobbecke, et al,"Effects of Short-Chain Alcohols on the Phase Behavior and Interdigitation of Phospatidylcholine Bilayer Membranes," Biochimiea et Biophysica Aeta 1237 (1995) 59-69.
Mezei, "Liposomes as a Skin Drug Delivery System," 1985 Elsevier Science Publishers B.V. (Biomedical Division), pp. 345-358.
Ogiso, Taro et al. "Membrane-Controlled Transdermal Therapeutic System Containing Clonazepam and Anticonvulsant Activity after its Application." Chem. Pharm. Bull., 37(2):446-449. (1989).
Schreier, H. "Liposomes—A Novel Drug Carrier, I. Phospholipids; Production and Characterization of Liposomes; II. Destiny of liposomes in vivo; use in therapy," Pharmazie in underer Zeit, No. 4 (1982).
Siddiqui, O. et al., "Nonparenteral Administration of Peptide and Protein Drugs," CRC Critical Reviews in Therapeutic Drug Carrier Systems, vol. 3, Issue 3 p. 195-208.
Almeida et al., "Nasal delivery of vaccines," Journal of Drug Targeting, vol. 3, No. 6, pp. 455-467 (1996).
Byas-Smith et al., "Transdermal clonidine compared to placebo in painful diabetic neuropathy using two stage 'enriched enrollment' design," Pain, vol. 60, pp. 267-274 (1995).

Carafa, M. et al. "Lidocaine-loaded Non-ionic Surfactant Vesicles: Characterization and In Vitro Permeation Studies," International Journal of Pharmaceutics 231:21-32. (2002).
Castillo et al., "Glucocorticoids Prolong Rat Sciatic Nerve Blockade In Vivo from Bupivacaine Microspheres," Anethesiology, vol. 85, No. 5, pp. 1157-1166 (1996).
Cevc et al., "Phospholipids handbook", Marcel Dekker, Inc., New York, Basel, Hong Kong, pp. 375-376 and 404 (1993).
Cevc, G. et al."New, Highly Efficient Formulation of Diclofenac for the Topical, Transdermal Administration in Ultradeformable Drug Carriers, Transfersomes," Biochimica et Biophysica Acta 1514 (2001) 191-205.
Claims filed Feb. 4, 2003, in connection with U.S. Appl. No. 10/357,617 (U.S. Patent Publication No. US 2004/0071767 A1).
Claims filed Oct. 20, 2006, in connection with U.S. Appl. No. 10/357,617 (U.S. Patent Publication No. US 2004/0071767 A1).
Claims filed Jan. 22, 2007, in connection with U.S. Appl. No. 10/037,480 (U.S. Patent Publication No. US 2003/0099694 A1).
Claims filed Mar. 20, 2006, in connection with U.S. Appl. No. 10/037,480 (U.S. Patent publication No. US 2003/0099694 A1).
Claims filed Sep. 21, 2005, in connection with U.S. Appl. No. 10/037,480 (U.S. Patent Publication No. US 2003/0099694 A1).
Claims filed Oct. 20, 2004, in connection with U.S. Appl. No. 10/037,480 (U.S. Patent Publication No. US 2003/0099694 A1).
Claims filed Jan. 4, 2002, in connection with U.S. Appl. No. 10/037,480 (U.S. Patent Publication No. US 2003/0099694 A1).
Claims filed Feb. 26, 2007, in connection with U.S. Appl. No. 10/984,450 (U.S. Patent Publication No. US 2005/0123897 a1).
Claims filed May 31, 2006, in connection with U.S. Appl. No. 10/984,450 (U.S. Patent Publication No. US 2005/0123897 A1).
Claims filed May 31, 2005, in connection with U.S. Appl. No. 10/984,450 (U.S. Patent Publication No. US 2005/0123897 A1).
Claims filed May 12, 2004, in connection with U.S. Appl. No. 10/357,618 (U.S. Patent Publication No. US 2004/0105881 A1).
Claims presently pending in U.S. Appl. No. 09/890,335.
Claims presently pending in U.S. Appl. No. 09/890,371.
International Search Report for International Patent Application No. PCT/EP2005/011986. (Jul. 4, 2006).
Definition of Microbicide, Wikipedia, The Free Online encyclopedia (2007).
Edwards, K. et al., "Effects of Trito X-100 on Sonicated Lecithin Vesicles," Langmuir, vol. 5, No. 2, 1989 pp. 473-478.
Frantzen et al., "Assessing the accuracy of routine Photon Correlation Sepectroscopy Analysis of Heterogeneous Size Distributions," AAPS PharmSciTech, vol. 4, No. 3, Article 36, pp. 1-9 (2003).
Friedrich, et al., "Physicochemical Characterization of a Reverse Micellar Solution after Loading with Different Drugs," Pharmazie 55 (2000) 10, 755-758.
Glen et al, "Skin immunization made possible by cholera toxin 'letter!'", Nature, GB, MacMillan Journal Ltd., London, vol. 391, No. 6670, pp. 851 (Feb. 1998).
Grahame R, "Transdermal non-steroidal anti-inflammatory agents," BJCP, vol. 49, No. 1, pp. 33-35 (Jan.-Feb. 1995).
Holzbach RT, "Detection of Vesicles in native and model Biles by Morphological and other structural Techniques: applications and limitations," Hepatology, Sep. 12 (3 Pt 2), pp. 106S-112S (1990).
Lehmann, J. et al. "Analgesic and anti-inflammatory efficacy of IDEA-070 in UVB-induced sunburn." Journal of the European Academy of Dermatology and Venereology, 18(S2):167-168. (Oct. 2004).
Merck Index: 10th Edition. pp. 779-780. (1983).
Office Action issued Apr. 11, 2007, in connection with U.S. Appl. No. 10/037,480 (U.S. Patent Publication No. US 2003/0099694 A1).
Office Action issued Dec. 19, 2005, in connection with U.S. Appl. No. 10/037,480 (U.S. Patent Publication No. US 2003/0099694 A1).
Office Action issued Dec. 28, 2006, in connection with U.S. Appl. No. 10/357,618 (U.S. Patent Publication No. 2004/0105881 A1).
Office Action issued Jan. 19, 2007, in connection with U.S. Appl. No. 10/357,617 (U.S. Patent Publication No. US 2004/0071767 A1).
Office Action issued Mar. 30, 2005, in connection with the U.S. Appl. No. 10/037,480 (U.S. Patent Publication No. U.S. 2003/0099694 A1).
Office Action issued May 30, 2006, in connection with U.S. Appl. No. 10/357,617 (U.S. Patent Publication No. US 2004/0071767 A1).

Office Action issued on Aug. 28, 2006, in connection with U.S. Appl. No. 10/984,450 (U.S. Patent Publication No. US 2005/0123897 A1).
Office Action issued on Feb. 7, 2006, in connection with U.S. Appl. No. 10/984,450 (U.S. Patent Publication No. US 2005/0123897 A1).
Office Action issued on May 16, 2007, in connection with U.S. Appl. No. 10/984,450 (U.S. Patent Publication No. US 2005/0123897 A1).
Office Action issued on Oct. 16, 2003, in connection with U.S. Appl. No. 10/037,480 (U.S. Patent Publication No. US 2003/0099694 A1).
Office Action issued on Sep. 20, 2006, in connection with U.S. Appl. No. 10/037,480 (U.S. Patent Publication No. US 2003/0099694 A1).
Paul et al., "Non Invasive administration of protein antigens: transdermal immunization with bovine serum albumin in transfersomes," Vaccine Research, vol. 4, No. 3, pp. 145-164 (1995).
Paul et al., "Transdermal immunisation with an integral membrane component gap junction protein, by means of ultradeformable drug carriers, transfersomes," Vaccine, vol. 16, No. 2-3, pp. 188-195 (Jan. 1998).
Product Information, "Polysorbate 80 VG" (2004).
Product Information, "Tween 80 Pure" (2004).
Ranade V., "Drug Delivery Systems.6. Transdermal Drug Delivery," J. Clin Pharmacol, vol. 31, pp. 401-418 (1991).
Trotta, M. et al. "Deformable liposomes for dermal administration of methotrexate." International Journal of Pharmaceutics, 270:119-125. (Feb. 11, 2004).
Trotta, M. et al. "Elastic liposomes for skin delivery of dipotassium glycyrrhizinate." International Journal of Pharmaceutics, 241(2):319-327. (Jul. 25, 2002).
Valenta, C. et al., "Evalutation of Novel Soya-lecithin Formulations for Dermal use containing Ketoprofen as a Model Drug," Journal of Controlled Release 63 (2000) 165-173.
Wess, L. "Down, down, deeper and down." Biocentury, The Bernstein Report on BioBusiness, 12(22):A11-A12. (May 17, 2004).
Benner, "The Human Body, The Wonderwork of the Human Body, Structure, Functions, Interactions, Processes and Mechanisms" Weltbild GmbH Augsburg (1995).
Serva, Feinbiochemica Fur Forschung for *Serva Feinbiochemica GmbH & Co.* (1986/1987).
Clark, J.M., Jr., "Experimental Biochemistry" Biochemistry Division, Department of Chemistry, University of Illinois, pp. 47-48, non dated.
Patel, H.M. "Liposomes as a Controlled-release System" Biomedical Society Transaction 609th Meeting, Leeds, pp. 513-516, non-dated.
Fieser, L.F., et al. "Organische Chemie" *Hans Ruprecht Hensel, 2nd revised edition, Verlag Chemie GmbH, Weinheim/ Bergstr* (1968).
Fluka Chemika-BioChemika Catalogue 16 (1988/89).
Roeding, J. "Liposomes and Niosomes in Pharmacy and Cosmetic State of the Art Prospects, Techniques of Visualizing Vesicular Systems, Interaction of Liposomes with the Skin" Training Course No. 105 from May 14 to 16, 1990, *Maritim Hotel Nurnberg, Frauentorgraben 11*, 8500 Nurenberg.
G. Ceve et al.,Transfersomes-mediated transepidermal delivery improves the regio-specificity and biological actibity of corticosteroids in vivo, *Journal of Controlled Release* 45 (1997) 211-226, non dated.
V.M. Knep P et al. "Controlled Drug Release From a Novel Liposomal Delivery System II. Transdermal Delivery Characteristics", Journal of Controlled Release 12 (Mar. 1990), No. 1, Amsterdam, NL, pp. 25-30.
C.E. Price, "A Review of the F Actors Influencing the Penetration of Pesticides Through Plant Leaves" on I.C.I. Ltd., Plant Protection Division, Jealott's Hill Research Station, Bracknell, Berkshire RG12 6EY, U.K., pp. 237-252, non-dated.
K. Karzel and R. K. Liedtke, "Mechanismen Transkutaner Resorption" on Grandlagen/Basics, pp. 1487-1491, non-dated.
Micha el Mezei, "Liposomes as a Skin Drug Delivery System" 1985 Elsevier Science Publishers B.V. (Biomedical Division), pp. 345-358, non-dated.
Adrienn Gesztes and Michael Mezei, "Topical Anesthesia of the Skin by Liposome-Encapsulated Tetracaine" on Anesth Analg 1988; 67: pp. 1079-1081, non dated.
A. Helenius, et al, "Solubilization of Membranes by Detergents", Biochimica et Biophysica Acta, 415 (1975) 29-79, non-dated.

Phillip G. Green, et al., "In Vitro and in Vivo Enhancement of Skin Permeation With Oleic and Lauric Acids" on International Journal of Pharmaceutics, 48 (1988), pp. 103-111, non-dated.
Guia M. Golden et al. "Role of Stratum Corneum Lipid Fluidity in Transdermal Drug Flux" on Journal of Pharmaceutical Sciences vol. 76, No. 1, Jan. 1987, American Pharmaceutical Association, pp. 25-28.
Bruce J. Aungst et al., "Enhancement of Naloxone Penetration Through Human Skin in Vitro Using Fatty Acids, Fatty Alcohols, Surfactants, Sulfoxides and Amides" on International Journal of Pharmaceutics, 33 (1986) pp. 225-234.
Ronal d R. Burnette et al., "Characterization of the Permselective Properties of Excised Human Skin During Lontophoresis" on Journal of Pharmaceutical Sciences vol. 76, No. 10, Oct. 1987, American Pharmaceutical Association, pp. 765-773.
E.C. Katoulis et al., "Efficacy of a New Needeless Insuling Delivery System Monitoring of Blood Glucose Fluctuations and Free Insulin Levels" on International Journal of Artificial Organs vol. 12, No. 5, 1989, pp. 333-338.
Ovals Siddiqui et al., "NonParenteral Administration of Peptide and Protein Drugs" on CRC Critical Reviews in Therapeutic Drug Carrier Systems, vol. 3, Issue 3, pp. 195-208, date unknown.
Cevc, G. et al., "U1 traflexible vesicles, Transfersomes, have an extremely low pore penetration resistance and transport therapeutic amounts of insuling across the intact mammalian skin", Biochimica et Biophysica Acta. 1368 pp. 201-215 (1998).
Cevc, G. "Material Transport Across Permeability Barriers by Means of Lipid Vesicles", Handbook of Biological Physics, vol. 1, pp. 465-490 (1995).
Mayer, L.D. et al., "Vesicles of variables sizes produced by a rapid extrusion procedure", Biochimica et Biophysica Acta, 858 pp. 161-165 (1986).
Patel, H.M. et al., "Oral Administration of Insulin by Encapsulation Within Liposomes", FEBS Letters, 62(1):60-63 (Feb. 1976).
Schreier, H. "Lipos omes—A Novel Drug Carrier, I. Phospholipids; Production and Characterization of Liposomes; II. Destiny of liposomes in vivo; use in therapy", Pharmazie in unserer Zeit, No. 4 (1982).
Beyer, C. et al., "Micro Emulsions" Pharmazie in unserer Zeit, No. 2 (1983).
Lichtenberg, D. et al., "Solubilization of Phospholipids by Detergents Structural and Kinetic Aspects" Biochimica et Biophysica Acta, 737 pp. 285-304 (1983).
Claims filed Oct. 5, 2007, in connection with U.S. Appl. No. 10/037,480 (U.S. Appl. No. US 2003/0099694 A1), under examination by Examiner Fortuna of the USPTO.
Anosov, et al. Electrical capacitance of hydrogenated egg lecithin bilayer lipid membranes in the lipid crystal to gel phase transition. Biofizika. 2003; 48(2): 240-245. (English Abstract).
Appeal by Opponent - Dec. 4, 1998, in connection with EP 0475160B1 Opposition (in German).
Attachment filed by Opponent Nov. 14, 1996 in connection with EP 0475160B1 Opposition (in German).
Burnham et al. The effectiveness of topical diclofenac for lateral epicondylitis. Clin J Sport Med. 1998; 8(2):78-81.
Cevc et al. Ultradeformable lipid vesicles can penetrate the skin and other semi- permeable barriers unfragmented. Evidence from double label CLSM experiments and direct size measurements. Biochimica et Biophysica Acta. 2002; 1564:21-30.
Decision of EP Opposition Division Jul. 30, 1998 in connection with EP 0475160B1 Opposition (in German).
English translation of counterstatement of Patentee filed Jul. 11, 1997 in connection with DE 4447287 Cl Opposition.
English translation of Opponent's response to Office Action filed Mar. 17, 1998 in connection with DE 4447287 Cl Opposition.
English translation of Opposition filed Feb. 6, 1997 in connection with DE 4447287 Cl Opposition.
English translation of Patentee's response to Office Action filed Feb. 9, 1999 in connection with DE 4447287 Cl Opposition.
Erjavec, et al. In Vivo Study of Liposomes as Drug Carriers to Oral Mucosa using EPR Oximetry. Int. J. Pharmaceut. 2006; 307:1-8.
FR1SKEN, et al. Studies of vesicle extrusion. Langmuir. 2000; 16:928-933.

Hunter, et al. Effect of extrusion pressure and lipid properties on the size and polydispersity of lipid vesicles. Biophys J. 1998; 74:2996-3002.
Opponent's response filed May 22, 1998 in connection with EP 0475160B1 Opposition (in German).
Patentee communication to the EPO filed May 22, 1998 in connection with EP 0475160B1 Opposition (in German).
Patentee's response to Opposition Request filed Apr. 21, 1997 in connection with EP 0475160B1 Opposition (in German).
Pending claims in U.S. Appl. No. 09/555,986.
Pending claims in U.S. Appl. No. 10/037,480.
Pending claims in U.S. Appl. No. 10/357,617.
Pending claims in U.S. Appl. No. 10/357,618.
Pending claims in U.S. Appl. No. 10/984,450.
Pending claims in U.S. Appl. No. 11/545,904.
Response by Patentee filed Apr. 19, 1999 in connection with EP 0475160B1 Opposition (in German).
Saunders et al. A novel skin penetration enhancer: evaluation by membrane diffusion and confocal microscopy. J Pharm Pharmaceut Sci. 1999; 2(3):99-107.
Search Report for PCT/EP91/01596.
Gregor CEVC. U.S.Appl. No. 11/667,325, entitled "Extended Surface Aggregates in the Treatment of Skin Conditions," filed May 8, 2007.
Gregor CEVC. U.S. Appl. No. 11/929,480, entitled "Method For Developing Testing, And Using Associates Of Macromolecules And Complex Aggregates For Improved Payload And Controllable De/Association Rates," filed Oct. 30, 2007.
Gregor CEVC. U.S. Appl. No. 11/929,544, entitled "Method For Developing testing, And Using Associates Of Macromolecules And Complex Aggregates For Improved Payload And Controllable De/Association Rates," filed on Oct. 30, 2007.
Office Action mailed Apr. 2, 2008 in connection with U.S. Appl. No. 09/284,683, assigned to IDEA AG, under examination by Examiner Kishore at the USPTO.
Claims pending on Apr. 2, 2008 in connection with U.S. Appl. No. 09/284,683, assigned to IDEA AG, under examination by Examiner Kishore at the USPTO.
Office Action mailed Aug. 10, 2006 in connection with U.S. Appl. No. 09/555,986, assigned to IDEA AG, now abandoned.
Claims pending on Aug. 10, 2006 in connection with U.S. Appl. No. 09/555,986, assigned to IDEA AG, now abandoned.
Office Action mailed Jan. 9, 2008 in connection with U.S. Appl. No. 10/037,480, assigned to IDEA AG, under examination by Examiner Fortuna at the USPTO.
Claims pending on Jan. 9, 2008 in connection with U.S. Appl. No. 10/037,480, assigned to IDEA AG, under examination by Examiner Fortuna at the USPTO.
Office Action mailed May 15, 2008 in connection with U.S. Appl. No. 10/984,450, assigned to IDEA AG, under examination by Examiner Fortuna at the USPTO.
Claims pending on May 15, 2008 in connection with U.S. Appl. No. 10/984,450, assigned to IDEA AG, under examination by Examiner Fortuna at the USPTO.
Office Action mailed Sep. 21, 2007 in connection with U.S. Appl. No. 10/357,617, assigned to IDEA AG, under examination by Examiner Kishore at the USPTO.
Claims pending on Sep. 21, 2007 in connection with U.S. Appl. No. 10/357,617, assigned to IDEA AG, under examination by Examiner Kishore at the USPTO.
Amendment filed on May 19, 2008 in connection with U.S. Appl. No. 10/357,617, assigned to IDEA AG, under examination by Examiner Kishore at the USPTO.
Office Action mailed Mar. 19, 2008 in connection with U.S. Appl. No. 10/357,618, assigned to IDEA AG, under examination by Examiner Ghali at the USPTO.
Claims pending on Mar. 19, 2008 in connection with U.S. Appl. No. 10/357,618, assigned to IDEA AG, under examination by Examiner Ghali at the USPTO.
Declaration of Gregor CEVC under 37 C.F.R. §1.132, filed on Oct. 20, 2006 in U.S. Appl. No. 10/357,617, now U.S. Patent No. 7,473,432, assigned to IDEA AG, which was examined at the USPTO by Examiner Kishore.
Supplemental Declaration of Gregor CEVC under 37 C.F.R. §1.132, filed on Jul. 18, 2007, in U.S. Appl. No. 10/357,617, now U.S. Patent No. 7,473,432, assigned to IDEA AG, which was examined at the USPTO by Examiner Kishore.
Second Supplemental Declaration of Gregor CEVC under 37 C.F.R. §1.132, filed on Mar. 13, 2008 in U.S. Patent Application 10/357,617, now U.S. Patent No. 7,473,432, assigned to IDEA AG, which was examined at the USPTO by Examiner Kishore.
Third Supplemental Declaration of Gregor CEVC under 37 C.F.R. §1.132, filed on Apr. 18, 2008 in U.S. Appl. No. 10/357,617, now U.S. Patent No. 7,473,432, assigned to IDEA AG, which was examined at the USPTO by Examiner Kishore.
Declaration of Gregor CECV under 37 C.F.R. §1.132, filed on Jan. 15, 2009 in co-pending U.S. Appl. No. 12/244,703, assigned to IDEA AG, awaiting examination at the USPTO.
U.S. Appl. No. 12/244,703, entitled "NSAID Formulations, Based on Highly Adaptable Aggregates, for Improved Transport Through Barriers and Topical Drug Delivery", and Preliminary Amendment filed on Oct. 2, 2008.
U.S. Appl. No. 12/250,823, entitled "NSAID Formulations, Based on Highly Adaptable Aggregates, for Improved Transport Through Barriers and Topical Drug Delivery", and Preliminary Amendment filed on Oct. 14, 2008.
U.S. Appl. No. 12/250,980, entitled "NSAID Formulations, Based on Highly Adaptable Aggregates, for Improved Transport Through Barriers and Topical Drug Delivery", and Preliminary Amendment filed on Oct. 14, 2008.
U.S. Appl. No. 12/356,381, entitled "Aggregates With Increased Deformability, Comprising At Least Three Amphipats, for Improved Transport Through Semi-Permeable Barriers and for the Non-Invasive Drug Application in Vivo, Especially Through the Skin", and Preliminary Amendment filed on Jan. 20, 2009.

* cited by examiner

METHOD FOR THE IMPROVEMENT OF TRANSPORT ACROSS ADAPTABLE SEMI-PERMEABLE BARRIERS

This application is a continuation of copending application(s) application Ser. No. 10/037,480, filed on Jan. 4, 2002 International Application PCT/EP00/06367 filed on Jul. 5, 2000 which designated the U.S., which is a continuation of PCT/EP99/04659 filed on Jul. 5, 1999.

Any nonprovisional application claiming the benefit of one or more prior filed copending provisional applications must contain or be amended to contain in the first sentence of the specification following the title a reference to each such prior provisional application, identifying it as a provisional application, and including the provisional application number (consisting of series code and serial number). 37 C.F.R. § 1.78(a)(4).

The present invention is in the field of administration of drugs and particularly drug delivery across barriers. It more particularly relates to a method for controlling the flux of penetrants across an adaptable, semi-permeable porous barrier. It further relates to a kit and a patch which both enable the drug to be controllably applied.

A porous barrier as used herein is any obstacle comprising pores which are too narrow to let the penetrants diffusively pass. This necessarily implies that the penetrants are bigger than the average diameter of such a pore.

Some barriers, such as artificial porous membranes, for example ion-track polycarbonate membranes, may have permanent properties, while others are characterised by a possible change of their properties. Most notably the pore size and more rarely the pore density, may change as a function of the surroundings and/or of the flux of the penetrants through the pores in the barrier. The latter can be found with living tissues which are separated by boundaries with such properties, for example, cells and cell organelles.

The skin is used to further illustrate the basic principle of such a barrier:

The maximum barrier properties of the skin reside in the outermost skin region, that is, in the horny layer (stratum corneum). This is owing to special chemical and anatomical characteristics of the horny layer, which preclude most efficiently the passage of essentially any material across the skin. In the stratum corneum, 20-30 consecutive layers of the skin cells (chiefly corneocytes) are organised into columns. These columns are oriented perpendicular to the skin surface, permitting the cells from adjacent columns to overlap laterally and forcing the cells from one layer to be overlaid and packed densely. Intercellular junctions in the horny layer, moreover, are tightly sealed with specialised lipids, chiefly ceramides, which abound in the skin. The skin lipids are also predominantly well packed: typically, they form lipid multilamellae, which are coupled covalently to the neighbouring cell (envelope) membranes. Individual multilamellar stacks that run parallel to the cells surface are joined together with the less well ordered lipid domains. In such domains, the non-ceramide lipids (fatty acids, cholesteryl-sulphate, etc.) prevail.

The skin lipid tendency to self-arrange into densely packed, multilamellar structures is enhanced or even driven, by the hydration or certain ion (e.g. $Ca^{2+}$) concentration gradients in the skin. This may explain why similar lipid organisation is not observed elsewhere in the body except, with a much lower abundance, in the oral cavity.

Chemical skin permeation enhancers, for example dimethylsulfoxide, promote the diffusion of drugs across the skin by solubilising or extracting some of the intercellular lipids from the barrier. Transcutaneous transport is therefore most efficient in the least tightly packed lipid regions, where hydrophobic pores in the barrier are created most easily. Through such pores sufficiently small and lipophilic agents can diffuse along the transcutaneous concentration gradient(s). The resulting skin permeability is unaffected by the agent concentration, unless the agent acts as an enhancer, but the permeability depends on the concentration and the selection of skin permeation enhancer(s).

However the hydrophobic pores in the skin are not big enough to allow an appreciable transport of large drugs of any kind. Owing to the self-sealing tendency of the intercellular lipid domains the pores are also rather short lived. The lipophilicity of typical pores in the skin also precludes the transport of hydrophilic, that is, of highly polar, molecules across the organ. Conventional skin permeation enhancement is therefore only useful for the delivery of fatty materials which do not irritate the skin too much, the enhancer-mediated transport and irritation being poorly tolerated by the consumers in many cases.

Therefore to date, permeation based drug delivery through the skin is really successful only for small drugs with a molecular weight below 400 Da. Such drugs can partition into the intercellular lipid matrix in the skin and then diffuse through small hydrophobic pores in the horny layer, first into the skin proper and then further down towards the deep body tissues. The resulting steady state transport is preceded by a short lag-time period, during which the drug traverses the barrier. Transcutaneous transport does not suffer from the first pass effect, however.

The bioavailability of drugs delivered through the skin by such conventional means is typically below 50%, and often does not even reach 25% (Hadgraft, 1996; Cevc, 1997).

Large hydrophobic molecules normally cross the skin in negligible quantity only. As already mentioned above this is due to the lack of suitable passages in the skin. Transcutaneous transport of macromolecules therefore chiefly relies on the molecular diffusion through shunts, such as pilosebaceous units. To deliver a bulky and highly polar agent across the skin other methods than those conventionally used are therefore required. For example various skin poration techniques were introduced to create hydrophilic pores in the skin suitable for the purpose (to avoid confusion we will call such hydrophilic pores channels):

The simplest, and crudest solution, for making a wide channel through the skin is to eliminate mechanically the skin barrier. For example, to deliver a large, hydrophilic antidiuretic peptide 1-deamino-8-D-arginine vasopressin across the human skin from an occlusive patch the removal of a small piece of epidermis by vacu-suction has been used (Svedman et al., 1996).

Further, a most common method for opening a wide channel through the skin is to use an injection needle or mechanical impact(s) (injection; powderjection). Locally restricted skin challenge is also possible. This can be done by local heat application (thermoporation); by using high voltage pulses (>150 V; electroporation); or by acoustic energy, such as ultrasound (few $W\ cm^{-2}$; sonoporation). The resulting channel size depends on the nature and intensity of the skin treatment, but not on the nature or the applied amount of molecules to be transported.

Openings or even craters in the skin created by the above mentioned methods heal rather slowly under normal application conditions; the wider the passage, the more so. The skin thus may behave as an adaptable, but slowly recoverable barrier.

Even the most commonly used methods for making pores in the skin rely on gadgets plus experience for the proper operation; they also involve skin disinfection to protect the patient. This notwithstanding, their harm and inconvenience is tolerated as long as therapeutic benefit is achieved.

The most recent tool for creating hydrophilic passages in those barriers, such as the skin is provided by microscopic barrier penetrants which directly and reversibly open said hydrophilic channels. Such penetrants are independent of external energy source and also do not rely on any gadgets. They are also well tolerated by the skin.

Such penetrants known to date all belong to the class of highly deformable complex droplets (Transfersomes®). Such droplets adapt to the pores of the barrier—which they then cross efficiently—provided that the droplet components and preparation are properly selected and/or optimised. A sufficiently adaptable and hydrophilic droplet can therefore cross the barrier, such as skin, spontaneously. Such hydrophilic channels are opened transiently by the moving penetrant after the latter has adjusted its shape to achieve the goal. This allows the adjustable droplets to act as vehicles for the delivery of various—hydrophilic or hydrophobic—agents across the barrier.

Most useful droplets comprise an aqueous core surrounded by an highly flexible mixed lipid bilayer, which makes the aggregate ultradeformable and superficially highly hydrophilic. Both is required for an efficient transcutaneous transport (Cevc, 1997). Said droplets were demonstrated to transport their mass rather efficiently across the skin under optimum application conditions (Cevc, 1997).

Other types of aggregates (liposomes, niosomes, nanoparticles, microemulsions, etc.) also have been claimed to traverse the skin efficiently but were seldom, if ever, proven really to deliver the associated drugs across the skin in practically meaningful quantities. It is believed that in contrast to the highly deformable droplets (Transfersomes®) the used aggregates are either insufficiently deformable and/or are too unstable to achieve the goal. Conventional aggregates instead act as simple drug reservoirs on the skin: the aggregates, incapable of crossing the barrier, remain on the skin while the drug is released gradually from the 'vehicle' to then probably diffuse through the skin barrier on its own. The main action of conventional drug loaded suspensions is thus to increase the skin barrier hydration and/or to shed the molecules with the skin permeation enhancing capability into the tissue.

Contrary, the composite, ultradeformable lipid droplets (Transfersomes®) deform and then penetrate the skin rather than to coalesce locally. Such aggregates motion across the skin seems to proceed along the natural moisture gradient(s) between the skin cells, which guides the aggregates into the hydrophilic (virtual) channels in the organ.

The predecessors of those channels that let highly adaptable droplets pass through the skin are originally so narrow that they only permit evaporation of (rather small) water molecules across the skin. These originally tiny pores (diameter<0.5 nm) seem to open reversibly, however, when the stress of partial dehydration of a droplet, which is thereby being forced into the channel mouth under non-occlusive conditions, becomes excessive. The strong hydrophilicity and the large mass of the droplet are the factors which maximise the droplets' tendency to move through the skin; however the droplet adaptability is the necessary condition for the success of said motion.

The movement of the droplets across the skin seems to proceed along the path pursued by the water molecules during the skin passage in the opposite direction. The droplets are thus guided into intercellular regions precisely at the points where the contacts between the above-cited skin sealing lipids are the weakest and the least tight. The corresponding skin region covered with the channels has been estimated to be around 4% of the total skin area, or less.

It is possible to associate small and large, hydrophobic and hydrophilic molecules with ultradeformable and highly adaptable droplet-like aggregates. Using such complex aggregate droplets all types of molecules can thus be delivered across the barrier, such as the stratum corneum.

High systemic availabilities of the drug transported are typically achieved. Relative efficiency of the transport across the skin exceeds 50%, in most cases (Cevc et al., 1996). The steady state is reached within few hours, by and large (Cevc et al., 1998).

It has already been proven that the skin barrier recovers fully after those droplets have been eliminated from the skin surface. In contrast, the channels created by other means, such as ultrasound remain open for at least 20 hours. In fact, they are not resealed properly before 2 days, even when relatively weak therapeutic ultrasound is used. Stronger perturbation causes more persistent skin damage (Mitragotri et al., 1995). (In the extreme case, when the barrier is eliminated by vacu-suction, the skin does not recover fully until after of 8 weeks.)

The precise size distribution of the channels in the skin, through which highly deformable droplets migrate spontaneously across the stratum corneum, is as yet unknown. It is probable, however, that it is asymmetric. The average width, that is, the distribution maximum has been estimated to be 20-30 nm under typically used application conditions. The skewed distribution could result from the existence of two quantitatively different but qualitatively similar intercellular transport routes across the skin (Schätzlein & Cevc, 1998) which together form the family of transcutaneous pathways.

The first, inter-cluster pathway leads between the groups of corneocytes. It represents the high-end tail of channel-size distribution and typically starts at the bottom of inter-cluster gorges. From here, it follows the dense material filling such gorge and offers the lowest resistance to penetration at the junctions where several clusters meet.

The second, intra-cluster pathway leads between the individual corneocytes in each cluster of corneocytes. This route typically proceeds along the lipid layers surface. In the projection over the outer third of the stratum corneum, the inter-corneocyte pathway resembles an interwoven three-dimensional network including all the cells in the organ. (Schätzlein & Cevc, 1998).

The above mentioned distinctions are quantitative in nature. No doubt exists that transcutaneous channels with the exception of pilosebaceous units are resistant to the passage of non-deformable, large aggregates.

Channel properties are also sufficiently constant to reveal little inter-site, inter-individual, inter-species or inter-carrier variability. According to the prior art, the relative bio-availability of different drugs in the blood after an epicutaneous administration in highly adaptable droplets (Transfersomes®) is fairly constant (Cevc, 1997). Pore distribution depends little on the nature of the penetrant or the drug. The same has been implied for the dose dependence, which was concluded to affect merely the depth of penetrant and drug distribution. Small dose per area was found to favour the local (superficial) retention whereas a large dose per area was shown to ensure a relatively great systemic availability.

Surprisingly, and contrary to the above-mentioned conclusion, we have now found out that changing the applied dose above a certain threshold and in sufficiently wide range not only affects the drug/penetrant distribution, but also determines the rate of penetrant transport across the barrier.

Our new and unexpected finding provides means for controlling the rate of transcutaneous drug delivery whenever highly deformable carriers are used on the barrier; it also provides the basis for better, i.e. more rational, design of the delivery device. There will especially be profit for the development of cutaneous patches suitable for the use in combination with highly adaptable carriers (Transfersomes®). Improved therapy and higher commercial value of the products should be the consequence.

It stands to reason that the observed new effect reflects the widening of channels in the barrier, but the applicant does not wish to be bound to this hypothesis. The newly found dosage-dependent pore widening is probably different for various transcutaneous channels: the originally narrower pores probably change more than the relatively wide (e.g. inter-cluster) channels. The effect of relative channel size, that is, of channel vs. penetrant size ratio, suggests that it will take much longer time to bring certain penetrants quantity through narrow than through wide channels.

If the channels act as transported mass discriminators, and adjust their width to the flux requirement, the narrow channels will persist much longer in their original, high penetration resistance state than the wide channels. However, after having responded to the multi-penetrant passage by increasing their width such channels will start to behave as the originally wider channels. Multiple adjustments are possible but only to certain upper limit.

Another potentially important factor acting in the same direction is the skin surface hydration, which is prone to increase with enlargement of the topically administered dosage. In either case, the average width and the size distribution of channels in the skin will shift towards greater values with increasing applied dosage. This then will result in higher final transcutaneous flux.

For the avoidance of doubt, all pertinent information, definitions and lists from the previous patent applications of the same applicant are incorporated herein by reference.

Kits and more particularly devices for administering drugs through a barrier such as skin or mucosa have also already been described. These devices can typically be divided into matrix systems and liquid reservoir systems.

Container-type reservoirs are often formed as a pocket between the backing layer and a rate controlling membrane through which the drug passes to the skin. The pressure sensitive adhesive layer normally underlies the membrane and the drug also passes through it on its way to the skin.

As mentioned above it is customary to prepare reservoir type patches for transdermal drug delivery with a backing membrane and a rate controlling membrane (Ogiso, T., Y. Ito, et al. (1989). "Membrane-controlled transdermal therapeutic system containing clonazepam and anticonvulsant activity after its application." *Chem Pharm Bull* (*Tokyo*) 37, 446-9; Ito, Y., T. Ogiso, et al. (1993). "Percutaneous absorption of acemetacin from a membrane controlled transdermal system and prediction of the disposition of the drug in rats" *Biol. Pharm. Bull* 16, 583-8)

A number of reservoir type systems have been described.

U.S. Pat. No. 829,224 to Chang et al., for instance, discloses a device with a reservoir that is defined by a backing layer and a drug-permeable membrane layer. A ring-shaped layer made of an adhesive is peripheral to the reservoir. A peelable liner layer underlies the membrane. A second peelable layer, the release liner, underlies the entire assembly. A first heat seal connects the backing layer and the membrane and surrounds the reservoir. A second heat seal concentric about the first heat seal connects the backing layer and the release liner. The second heat seal is broken when the release liner is removed. The device may include an inner liner that underlies the membrane and portions of the backing layer. This inner liner is removed following removal of the release liner so that the membrane is exposed.

U.S. Pat. No. 4,983,395 to Chang et al., relates to another device with a backing layer and a membrane layer that define a reservoir. A peelable inner liner underlies the reservoir and portions of the backing and membrane layers outside the periphery of the reservoir. An adhesive layer underlies the inner liner and remaining portions of the backing and membrane layers. A peelable release liner underlies the adhesive layer. A first heat seal connects the backing and membrane layers on the periphery of the reservoir. A second heat seal underlies the first heat seal and connects the membrane and the inner liner. In use, the release liner and inner liner are peeled away to expose the undersurfaces of the membrane and adhesive layers prior to placement of the device onto the skin or mucosa.

PCT-Application WO96-19205 to Theratech, Inc., discloses a device for administering an active agent to the skin or mucosa of an individual comprising a laminated composite of an adhesive overlay, a backing layer underlying the central portion of the adhesive overlay, an active agent-permeable membrane, the backing layer and membrane defining a reservoir that contains a formulation of the active agent, a peel-seal disc underlying the active agent-permeable membrane, a heat seal about the periphery of the peel seal disc, the active agent-permeable membrane and the backing layer and a removable release liner underlying the exposed overlay and peel seal disc. The adhesive layer is above and peripheral to the path of the active agent to the skin or mucosa and is protected from degradation by the components of the reservoir by a multiplicity of heat seals. The peel seal disc protects against release of the active agent-containing reservoir and the release liner protects the adhesive from exposure to the environment prior to use.

U.S. Pat. No. 5,202,125 to Theratech, Inc., describes a transdermal delivery system for delivery of nitroglycerin which deliver the drug at enhanced transdermal fluxes. The systems include, in addition to nitroglycerin, a permeation enhancer which is either a sorbitan ester, a C8-C22 aliphatic alcohol, or a mixture thereof. Methods for administering nitroglycerin using such permeation enhancers are also disclosed.

WO90-11065 to Theratech, Inc., discloses a transdermal drug delivery device comprising a drug formulation containing reservoir defined by a backing layer and a drug-permeable membrane layer, a peelable inner liner that underlies the reservoir and a portion of the backing/membrane outwardly of the reservoir periphery, an adhesive layer that underlies the inner liner and outwardly extending portions of the membrane/backing layers, and a peelable release liner layer that underlies the adhesive layer with a first permanent heat seal between the backing and the membrane about the perimeter of the reservoir and another peelable (impermeant) heat seal between the membrane and the inner liner underlying the first permanent heat seal, the heat seals and peelable barrier layer providing barriers that isolate the drug formulation from the adhesive.

Depending on the features to be achieved, backing films are either occlusive or permeable and commonly are derived from synthetic polymers, such as polyester, polyethylene, polyvinylidine chloride (PVDC), polyurethane or natural polymers, such as cotton, wool, etc. It is possible to use nonporous, microporous, such as polypropylene or polyethylene or also macroporous woven and nonwoven materials as a backing layer in transdermal patches. The backing layers are generally selected from these materials depending on the active agent to be delivered.

Occlusive backings in classical TTS (transdermal transport systems) tend to promote higher deposition and a higher rate of permeation of the active or inactive ingredients into the skin compared to non-occlusive backing. Occlusive backings are e.g. desirable to enhance the delivery of steroids to the lower layers of the epidermis to treat inflammation and dermatoses. Examples are Actiderm® (dermatological patch) or Cordran® (tape and patch).

Semi-occlusive films, such as polyurethanes and polyolefin copolymers, and non-occlusive woven and nonwoven fiber-based materials, such as cotton and to polyester, allow water vapor transmission from the skin surface and from the patch. These semi-occlusive or non-occlusive materials are rarely used as backing materials in TTS. Thicker non-occlusive backings were only desirable for corn and callus removal products since the active agent needs only to be delivered to the outer layers of the stratum corneum. The non-occlusive woven and nonwoven materials used in many of these products mainly serve as a protective cushion.

Rate controlling membranes usually used in commercial ITS are thin (26-78 μm) nonporous ethylene vinyl acetates films, such as Transderm-Nitro®(Ciba-Geigy and ZAF-FARONI) Duragesic®, Estraderm®, and EstraGest®). Moreover, thin (26-78 μm) microporous films of polyethylene, such as Transderm-Scop®, Catapres® are used as rate controlling membrane in multilaminate solid state reservoir patches or in liquid reservoir TTS. Further examples for such microporous PE-membranes are β-Estro® and Androderm®. These membranes usually serve to limit the rate of diffusion of the drug onto and through the skin As already described above Transfersomes® are able to mediate agent or drug delivery through the skin due to the hydration gradient across the biological barrier. In contrary to customary transdermal transport systems, wherein the agent mediation commonly depends on classical Fick's law of diffusion, therapeutic systems suitable for Transfersomes® and useful for the method of the present invention must fulfill different criteria.

It is also problematic that Transfersome®-mediated drug delivery through the skin from a patch is hindered if an occlusive backing material is used. The use of an occlusive membrane as backing layer causes an increased Transfersomes® hydration, since e.g. vapors cannot leak from the patch. Accordingly the hydration gradient and therefore the driving force for the Transfersome® transport is dramatically lowered.

Another problem is that many of the non-occlusive woven and nonwoven backings, which customary serve as a protective cushion, retain the Transfersomes® due to adsorption and trapping of lipids and proteins in the fibrous structure.

Moreover, any classical microporous and non-porous rate-controlling membranes having a pore size of smaller than about 20 run may interfere with the passage of Transfersomes® through the pores due to size exclusion.

It is obvious to someone skilled in the art that the known transdermal patches having conventional backing and rate controlling membranes are not suitable for the mediation of Transfersomes® according to the present invention. The same applies to matrix-type patches.

In matrix-type transdermal patches are those in which the drug is contained in and released from a polymer matrix. The matrix is typically made of a pressure sensitive adhesive and defines the basal surface of the patch (i.e. the surface affixed to the skin).

A number of matrix type systems have been described.

U.S. Pat. No. 5,460,820 to Theratech, Inc., discloses a method of providing testosterone replacement therapy to a woman in need of such therapy comprising applying a testosterone-delivering patch to the skin of said woman which patch transdermally delivers 50 to 500 μg/day testosterone to the woman. The skin patch comprises a laminated composite of a backing layer and a matrix layer comprising a solution of testerone in a polymeric carrier, said matrix layer providing a sufficient daily dose of testosterone to provide said therapy.

U.S. Pat. No. 5,783,208 to Theratech, Inc., discloses a matrix-type transdermal patch for coadministering estradiol and another steroid wherein the matrix is composed of a N-vinyl-2-pyrrolidone-containing acrylic copolymer pressure sensitive adhesive, estradiol the other steroid, and optionally a permeation enhancer, and the respective fluxes of estradiol and the other steroid from the matrix are independent of the respective concentrations of the other steroid and estradiol in the matrix.

All pertinent information, definitions and lists from the patents and patent applications of the US-company Theratech, Inc. are expressively incorporated herein by reference.

As mentioned above, it is customary to prepare reservoir type patches for transdermal drug delivery with a backing membrane and a rate controlling membrane. These membranes form typically one compartment, which contains the corresponding formulation. This can be a—mostly alcoholic or aqueous—solution, an aqueous suspension or a gel which contains gel forming polymers. Parameters as chemical and physical stability, viscosity, concentrations of active ingredient(s) and excipients are not critical with respect to commercial one-compartment reservoir-types, since the currently most active ingredients (drugs) are stable, low-molecular-weight substances (nicotine, fentanyl, estradiol, scopolemin and others), which commonly do not interfere with e.g. additional ingredients such as antioxidants, stabilizers, cosolvents or penetration enhancers.

As already mentioned, the Transfersome®-mediated drug delivery through barriers clearly differs from customary drug delivery through the skin. While it is not possible administering high molecular drugs by transdermal patches known in the art, Transfersomes® in principle are suitable carriers for a drug of high molecular weight such as peptides (e.g. insulin) and proteins (serum albumin). It is clear to someone skilled in the art that problems may arise if e.g. labile proteins are mixed with interfering or destabilizing ingredients over an extended storage period in customary one-compartment patches.

In many cases sufficient stabilities of all ingredients are not achievable within one compartment. For example Transfersome®-forming phospholipids are most stable at pH 6.5, while proteins may have other pH values of optimal stability (e.g. Interferon-α-2b at pH=7.4 or pH=3). Therefore, it would be necessary to keep said substances in different media if stored over an extended time period. For example, Transfersomes of type-T are formulated and stable in phosphate-buffer, while hepatocyte growth factor (HGF) is stable in citrate-buffer. Moreover, commonly organic (co-)solvents are used to introduce antioxidants such as BHT into lipid aggregates. Said (co-)solvents may contribute to reduced solubility of the proteins as they lower the bulk dielectricity constant, thus reducing electrostatic repulsion. This may lead to uncontrolled, at least unwanted, aggregation and denaturation of the proteins.

It is an important object of the present invention to control the flux of highly deformable penetrants (Transfersomes®) across an adaptable semi-permeable porous barrier, such as the skin of a human or animal body or a plant. It is another object of the present invention to control the flux of highly deformable penetrants (Transfersomes®) across an adaptable semi-permeable porous barrier in using a kit or transdermal transport system which enables the formulation to be applied at the selected dose per area. It is a further object of the present invention to provide a reservoir-type transdermal patch suitable for the Transfersome®-mediated agent or drug delivery through the intact skin. Another object of the present invention is the provision of a long term stable multicompartment reservoir-type transdermal patch, which comprises separate compartments and is suitable for the Transfersome®-mediated agent or drug delivery through the intact skin.

According to the present invention this is achieved by a method for controlling the flux of penetrants across an adaptable semi-permeable porous barrier comprising the steps of:

preparing a formulation by suspending or dispersing said penetrants in a polar liquid in the form of fluid droplets surrounded by a membrane-like coating of one or several layers, said coating comprising at least two kinds or forms of amphiphilic substances with a tendency to aggregate, provided that said at least two substances differ by at least a factor of 10 in solubility in said polar liquid, and/or said substances when in the form of homo-aggregates (for the more soluble substance) or of hetero-aggregates (for any combination of both said substances) have a preferred average diameter smaller than the diameter of homo-aggregates containing merely the less soluble substance, and/or the more soluble substance tends to solubilise the droplet and the content of such substance is to up to 99 mol-% of solubilising concentration or else corresponds to up to 99 mol-% of the saturating concentration in the unsolubilised droplet, whichever is higher;

and/or the presence of the more soluble substance lowers the average elastic energy of the membrane-like coating to a value at least 5 times lower, more preferably at least 10 times lower and most preferably more than 10 times lower, than the average elastic energy of red blood cells or of phospholipid bilayers with fluid aliphatic chains, said penetrants being able to transport agents through the pores of said barrier or to enable agent permeation through the pores of said barrier after penetrants have entered the pores, selecting a dose amount of said penetrants to be applied on a predetermined area of said barrier to control the flux of said penetrants across said barrier, and applying the selected dose amount of said formulation containing said penetrants onto said area of said porous barrier.

Preferably the flux of penetrants across said barrier is increased by enlarging the applied dose amount of said penetrants.

It then is preferred if the pH of the formulation is between 3 and 10, more preferably is between 4 and 9, and most preferably is between 5 and 8.

According to another preferred feature of the present invention the formulation containing the penentrants comprises:

at least one thickening agent in an amount to increase the formulation viscosity to maximally 5 Nm/s, more preferably up to 1 Nm/s, and most preferably up to 0.2 Nm/s, so that formulation spreading-over, and drug retention at the application area is enabled, and/or at least one antioxidant in an amount that reduces the increase of oxidation index to less than 100% per 6 months, more preferably to less than 100% per 12 months and most preferably to less than 50% per 12 months and/or at least one microbicide in an amount that reduces the bacterial count of 1 million germs added per g of total mass of the formulation to less than 100 in the case of aerobic bacteria, to less than 10 in the case of entero-bacteria, and to less than 1 in the case of *Pseudomonas aeruginosa* or *Staphilococcus aureus*, after a period of 4 days.

It then is preferred if said at least one microbicide is added in an amount that reduces the bacterial count of 1 million germs added per g of total mass of the formulation to less than 100 in the case of aerobic bacteria, to less than 10 in the case of entero-bacteria, and to less than 1 in the case of *Pseudomonas aeruginosa* or *Staphilococcus aureus*, after a period of 3 days, and more preferably after a period of 1 day.

It then is also preferred if said thickening agent is selected from the class of pharmaceutically acceptable hydrophilic polymers, such as partially etherified cellulose derivatives, like carboxymethyl-, hydroxyethyl-, hydroxypropyl-, hydroxypropylmethyl- or methyl-cellulose; completely synthetic hydrophilic polymers such as polyacrylates, polymethacrylates, poly(hydroxyethyl)-, poly(hydroxypropyl)-, poly(hydroxypropylmethyl)methacrylates, polyacrylonitriles, methallyl-sulphonates, polyethylenes, polyoxiethylenes, polyethylene glycols-, polyethylene glycol-lactides, polyethylene glycol-diacrylates, polyvinylpyrrolidones, polyvinyl alcohols, poly(propylmethacrylamides), poly(propylene fumarate-co-ethylene glycols), poloxamers, polyaspartamides, (hydrazine cross-linked) hyaluronic acids, silicones; natural gums comprising alginates, carrageenans, guar-gums, gelatines, tragacanths, (amidated) pectins, xanthans, chitosan collagens, agaroses; mixtures and further derivatives or co-polymers thereof and/or other pharmaceutically, or at least biologically, acceptable polymers.

Preferably the concentration of said polymer is chosen to be in the range between 0.01 w-% and 10 w-%, more preferably in the range between 0.1 w-% and 5 w-%, even more preferably in the range between 0.25 w-% and 3.5 w-% and most preferably in the range between 0.5 w-% and 2 w-%.

Further it is preferred that said anti-oxidant is selected from synthetic phenolic antioxidants, such as butylated hydroxyanisol (BHA), butylated hydroxytoluene (BHT) and di-tert-butylphenol (LY178002, LY256548, HWA-131, BF-389, CI-986, PD-127443, E-5119, BI-L-239XX, etc.), tertiary butylhydroquinone (TBHQ), propyl gallate (PG), 1-O-hexyl-2,3,5-trimethylhydroquinone (HTHQ); aromatic amines (such as diphenylamine, p-alkylthio-o-anisidine, ethylenediamine derivatives, carbazol, tetrahydroindenoindol); phenols and phenolic acids (such as guaiacol, hydroquinone, vanillin, gallic acids and their esters, protocatechuic acid, quinic acid, syringic acid, ellagic acid, salicylic acid, nordihydroguaiaretic acid (NDGA), eugenol); tocopherols (including tocopherols (alpha, beta, gamma, delta) and their derivatives, such as tocopheryl-acylate (e.g. -acetate, -laurate, myristate, -palmitate, -oleate, -linoleate, etc., or any other suitable tocopheryl-lipoate), tocopheryl-POE-succinate; trolox and corresponding amide- and thiocarboxamide analogues; ascorbic acid and its salts, isoascorbate, (2 or 3 or 6)-o-alkylascorbic acids, ascorbyl esters (e.g. 6-o-lauroyl, myristoyl, palmitoyl-, oleoyl, or linoleoyl-L-ascorbic acid, etc.); non-steroidal anti-inflammatory agents (NSAIDs), such as indomethacin, diclofenac, mefenamic acid, flufenamic acid, phenylbutazone, oxyphenbutazone acetylsalicylic acid, naproxen, diflunisal, ibuprofen, ketoprofen, piroxicam, penicillamine, penicillamine disulphide, primaquine, quinacrine, chloroquine, hydroxychloroquine, azathioprine, phenobarbital, acetaminephen); aminosalicylic acids and derivatives; methotrexate, probucol, antiarrhythmics (e.g. amiodarone, aprindine, asocainol), ambroxol, tamoxifen, b-hydroxytamoxifen; calcium antagonists (such as nifedipine, nisoldipine, nimodipine, nicardipine, nilvadipine), beta-receptor blockers (e.g. atenolol, propranolol, nebivolol); sodium bisulphite, sodium metabisulphite, thiourea; chelating agents, such as EDTA, GDTA, desferral; endogenous defence systems, such as transferrin, lactoferrin, ferritin, cearuloplasmin, haptoglobion, haemopexin, albumin, glucose, ubiquinol-10; enzymatic antioxidants, such as superoxide dismutase and metal complexes with a similar activity, including catalase, glutathione peroxidase, and less complex molecules, such as beta-carotene, bilirubin, uric acid; flavonoids (e.g. flavones, flavonols, flavonones, flavanonals, chacones, anthocyanins), N-acetylcystein, mesna, glutathione, thiohistidine derivatives, triazoles; tannines, cinnamic acid, hydroxycinnamatic acids and their esters (e.g. coumaric acids and esters, caffeic acid and their esters, ferulic acid, (iso-) chlorogenic acid, sinapic acid); spice extracts (e.g. from clove, cinnamon, sage, rosemary, mace, oregano, allspice, nutmeg); carnosic acid, carnosol, carsolic acid; rosmarinic acid, rosmarindiphenol, gentisic acid, ferulic acid; oat flour extracts, such as avenanthramide 1 and 2; thioethers, dithioethers, sulphoxides, tetralkylthiuram disulphides; phytic acid, steroid derivatives (e.g. U74006F); tryptophan metabolites (e.g. 3-hydroxykynurenine, 3-hydroxyanthranilic acid), and organochalcogenides, or else is an oxidation suppressing enzyme.

Then, the concentration of BHA or BHT is often chosen to be between 0.001 and 2 w-%, more preferably is between 0.0025 and 0.2 w-%, and most preferably is between 0.005 and 0.02 w-%, of TBHQ and PG is between 0.001 and 2 w-%, more preferably is between 0.005 and 0.2 w-%, and most preferably is between 0.01 and 0.02 w-%, of tocopherols is between 0.005 and 5 w-%, more preferably is between 0.01 and 0.5 w-%, and most preferably is between 0.05 and 0.075 w-%, of ascorbic acid esters is between 0.001 and 5, more preferably is between 0.005 and 0.5, and most preferably is between 0.01 and 0.15 w-%, of ascorbic acid is between 0.001 and 5, more preferably is between 0.005 and 0.5 w-%, and most preferably is between 0.01 and 0.1 w-%, of sodium bisulphite or sodium metabisulphite is between 0.001 and 5, more preferably is between 0.005 and 0.5 w-%, and most preferably is between 0.01-0.15 w-%, of thiourea is between 0.0001 and 2 w-%, more preferably is between 0.0005 and 0.2, and most preferably is between 0.001-0.01 w-%, most typically 0.005 w-%, of cystein is between 0.01 and 5, more preferably is between 0.05 and 2 w-%, and most preferably is between 0.1 and 1.0 w-%, most typically 0.5 w-%, of monothioglycerol is between 0.01 and 5 w-%, more preferably is between 0.05 and 2 w-%, and most preferably is between 0.1-1.0 w-%, most typically 0.5 w-%, of NDGA is between 0.0005-2 w-%, more preferably is between 0.001-0.2 w-%, and most preferably is between 0.005-0.02 w-%, most typically 0.01 w-%, of glutathione is between 0.005 and 5 w-%, more preferably is between 0.01 and 0.5 w-%, and most preferably is between 0.05 and 0.2 w-%, most typically 0.1 w-%, of EDTA is between 0.001 and 5 w-%, even more preferably is between 0.005 and 0.5 w-%, and most preferably is between 0.01 and 0.2 w-%, most typically between 0.05 and 0.975 w-%, of citric acid is between 0.001 and 5 w-%, even more preferably is between 0.005 and 3 w-%, and most preferably is between 0.01-0.2, most typically between 0.3 and 2 w-%.

Furthermore it is preferred if said microbicide is selected amongst short chain alcohols, such as ethyl and isopropyl alcohol, chlorbutanol, benzyl alcohol, chlorbenzyl alcohol, dichlorbenzylalcohol; hexachlorophene; phenolic compounds, such as cresol, 4-chloro-m-cresol, p-chloro-m-xylenol, dichlorophene, hexachlorophene, povidon-iodine; parabens, especially alkyl-paraben, such as methyl-, ethyl-, propyl-, or butyl-paraben, benzyl-paraben; acids, such as sorbic acid, benzoic acid and its salts; quaternary ammonium compounds, such as alkonium salts, e.g. benzalkonium salts, especially the chlorides or bromides, cetrimonium salts, e.g. the bromide; phenoalkecinium salt, such as phenododecinium bromide, cetylpyridinium chloride or other such salts; mercurium compounds, such as phenylmercuric acetate, borate, or nitrate, thiomersal; chlorhexidine or its gluconate; antibiotically active compounds of biological origin, or a mixture thereof.

Preferably the bulk concentration of short chain alcohols in the case of ethyl, propyl, butyl or benzyl alcohol is up to 10 w-%, more preferably is up to 5 w-%, and most preferably is in the range between 0.5-3 w-%, and in the case of chlorobutanol is in the range between 0.3-0.6 w-%; bulk concentration of parabens, especially in the case of methyl paraben is in the range between 0.05-0.2 w-%, and in the case of propyl paraben is in the range between 0.002-0.02 w-%; bulk concentration of sorbic acid is in the range between 0.05-0.2 w-%, and in the case of benzoic acid is in the range between 0.1-0.5 w-%; bulk concentration of phenols, triclosan, is in the range between 0.1-0.3 w-%, and bulk concentration of chlorhexidine is in the range between 0.01-0.05 w-%.

It is preferred that the less soluble amongst the aggregating substances is a lipid or lipid-like material, especially a polar lipid, whereas the substance which is more soluble in the suspending liquid and which lowers the average elastic energy of the droplet is a surfactant or else has surfactant-like properties and/or is a form of said lipid or lipid-like material which is comparably soluble as said surfactant or the surfactant-like material.

Preferably the lipid or lipid-like material is a lipid or a lipid from a biological source or a corresponding synthetic lipid or any of its modifications, said lipid preferably belonging to the class of pure phospholipids corresponding to the general formula

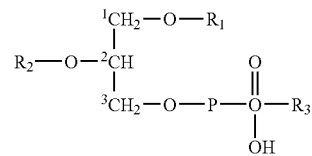

where $R_1$ and $R_2$ is an aliphatic chain, typically a $C_{10-20}$-acyl, or -alkyl or partly unsaturated fatty acid residue, in particular, an oleoyl-, palmitoeloyl-, elaidoyl-, linoleyl-, linolenyl-, linolenoyl-, arachidoyl-, vaccinyl-, lauroyl-, myristoyl-, palmitoyl-, or stearoyl chain; and where $R_3$ is hydrogen, 2-trimethylamino-1-ethyl, 2-amino-1-ethyl, $C_{1-4}$-alkyl, $C_{1-5}$-alkyl substituted with carboxy, $C_{2-5}$-alkyl substituted with hydroxy, $C_{2-5}$-alkyl substituted with carboxy and hydroxy, or $C_{2-5}$-alkyl substituted with carboxy and amino, inositol, sphingosine, or salts of said substances, said lipid comprising also glycerides, isoprenoid lipids, steroids, sterines or sterols, of sulphur- or carbohydrate-containing lipids, or any other bilayer-forming lipids, in particular half-protonated fluid fatty acids, said lipid is selected from the group comprising phosphatidylcholines, phosphatidylethanolamines, phosphatidylglycerols, phosphatidylinositols, phosphatidic acids, phosphatidylserines, sphingomyelins or other sphingophospholipids, glycosphingolipids (including cerebrosides, ceramidepolyhexosides, sulphatides, sphingoplasmalogens), gangliosides and other glycolipids or synthetic lipids, in particular with corresponding sphingosine derivatives, or any other glycolipids, whereby two similar or different chains can be ester-groups-linked to the backbone (as in diacyl and dialkenoyl compound) or be attached to the backbone with ether bonds, as in dialkyl-lipids.

The surfactant or surfactant-like material preferably is a nonionic, a zwitterionic, an anionic or a cationic surfactant, especially a fatty-acid or -alcohol, an alkyl-tri/di/methyl-ammonium salt, an alkylsulphate salt, a monovalent salt of cholate, deoxycholate, glycocholate, glycodeoxycholate, taurodeoxycholate, taurocholate, etc., an acyl- or alkanoyl-dimethyl-aminoxide, esp. a dodecyl-dimethyl-aminoxide, an alkyl- or alkanoyl-N-methylglucamide, N-alkyl-N,N-dimethylglycine, 3-(acyldimethylammonio)-alkanesulphonate, N-acyl-sulphobetaine, a polyethylene-glycol-octylphenyl ether, esp. a nonaethylene-glycol-octylphenyl ether, a polyethylene-acyl ether, esp. a nonaethylen-dodecyl ether, a polyethylene-glycol-isoacyl ether, esp. a octaethylene-glycol-isotridecyl ether, polyethylene-acyl ether, esp. octaethylenedodecyl ether, polyethylene-glycol-sorbitane-acyl ester, such as polyethylenglykol-20-monolaurate (Tween 20) or polyethylenglykol-20-sorbitan-monooleate (Tween 80), a polyhydroxyethyleneacyl ether, esp. polyhydroxyethylene-lauryl, -myristoyl, -cetylstearyl, or -oleoyl ether, as in polyhydroxyethylene-4 or 6 or 8 or 10 or 12, etc., -lauryl ether (as in Brij series), or in the corresponding ester, e.g. of polyhydroxyethylen-8-stearate (Myrj 45), -laurate or -oleate type, or in polyethoxylated castor oil 40, a sorbitane-monoalkylate (e.g. in Arlacel or Span), esp. sorbitane-monolaurate, an acyl- or alkanoyl-N-methylglucamide, esp. in or decanoyl- or dodecanoyl-N-methylglucamide, an alkyl-sulphate (salt), e.g. in lauryl- or oleoyl-sulphate, sodium deoxycholate, sodium glycodeoxycholate, sodium oleate, sodium taurate, a fatty acid salt, such as sodium elaidate, sodium linoleate, sodium laurate, a lysophospholipid, such as n-octadecylene(=oleoyl)-glycerophosphatidic acid, -phosphorylglycerol, or -phosphorylserine, n-acyl-, e.g. lauryl or oleoyl-glycero-phosphatidic acid, -phosphorylglycorol, or -phosphorylserine, n-tetradecyl-glycero-phosphatidic acid, -phosphorylglycerol, or -phosphorylserine, a corresponding palmitoeloyl-, elaidoyl-, vaccenyl-lysophospholipid or a corresponding short-chain phospholipid, or else a surface-active polypeptide.

According to a preferred feature of the present invention, the average diameter of the penetrant is between 30 nm and 500 nm, more preferably between 40 nm and 250 nm, even more preferably between 50 nm and 200 nm and particularly preferably between 60 nm and 150 nm.

It is another preferred feature of the present invention that the total dry weight of droplets in a formulation is 0.01 weight-% (w-%) to 40 w-% of total formulation mass, more preferably is between 0.1 w-% and 30 w-%, and most preferably is between 0,5 w-% and 20 w-%.

It is preferred that the total dry weight of droplets in a formulation is selected to increase the formulation viscosity to maximally 200 mPas, more preferably up to 40 mPas, and most preferably up to 8 mPas.

According to the present invention is is preferred if at least one edge-active substance or surfactant and/or at least one amphiphilic substance, and/or at least one hydrophilic fluid and the agent are mixed, if required separately, to form a solution, the resulting (partial) mixtures or solutions are then combined subsequently to induce, preferably by action of mechanical energy such as shaking, stirring, vibrations, homogenisation, ultrasonication, shearing, freezing and thawing, or filtration using convenient driving pressure, the formation of penetrants that associate with and/or incorporate the agent Preferrably this amphiphilic substances are dissolved in volatile solvents, such as alcohols, especially ethanol, or in other pharmaceutically acceptable organic solvents, such as ethanol, 1- and 2-propanol, benzyl alcohol, propylene glycol, polyethylene glycol (molecular weight: 200-400 D) or glycerol, other pharmaceutically acceptable organic solvents, such as undercooled gas, especially supercritical $CO_2$, which are then removed, especially by evaporation or dilution, prior to making the final preparation.

According to the present invention the formation of said penetrants preferrably is induced by the addition of required substances into a fluid phase, evaporation from a reverse phase, by injection or dialysis, if necessary under the influence of mechanical stress, such as shaking, stirring, especially high velocity stirring, vibrating, homogenising, ultrasonication, shearing, freezing and thawing, or filtration using convenient, especially low (1 MPa) or intermediate (up to 10 MPa), driving pressure.

Then the formation of said penetrants preferrably is induced by filtration, the filtering material having pores sizes between 0.01 μm and 0.8 μm, more preferably between 0.02 μm and 0.3 μm, and most preferably between 0.05 μm and 0.15 μm, whereby several filters may be used sequentially or in parallel.

According to the invention said agents and penetrants preferably are made to associate, at least partly, after the formation of said penetrants, e.g. after injecting a solution of the drug in a pharmaceutically acceptable fluid, such as ethanol, 1- and 2-propanol, benzyl alcohol, propylene glycol, polyethylene glycol (molecular weight: 200-400 D) or glycerol into the suspending medium, simultaneously with penetrant formation, if required using the drug co-solution and, at least some, penetrant ingredients.

It is preferred if said penetrants, with which the agent is associated are prepared immediately before the application of the formulation, if convenient, from a suitable concentrate or a lyophylisate.

The formulation according to the invention preferrably is applied by spraying, smearing, rolling or sponging on the application area, in particular by using a metering sprayer, spender, roller, sponge or a non-occlusive patch, as appropriate.

It is preferred if the barrier is a part of a mammalian body and/or a plant and preferably is skin and/or at least partly keratinised endothelium and/or nasal or any other mucosa.

The area dose of said penetrant then preferrably is between 0.1 mg per square centimeter (mg $cm^{-2}$) and 40 mg $cm^{-2}$, more preferably is between 0.25 mg $cm^{-2}$ and 30 mg $cm^{-2}$ and even more preferably is between 0.5 mg $cm^{-2}$ and 15 mg $cm^{-2}$, in the case that the penentrant is applied on said skin and/or said at least partly keratinised endothelium.

The area dose of said penetrant then preferrably is between 0.0001 mg per square centimeter (mg $cm^{-2}$) and 0.1 mg $cm^{-2}$, more preferrably is between 0.0005 mg $cm^{-2}$ and 0.05 mg $cm^{-2}$ and even more preferrably is between 0.001 mg $cm^{-2}$ and 0.01 mg $cm^{-2}$, in the case that the penetrant is applied on plant body, plant leaves or plant needles.

The area dose of said penetrant then preferrably is between 0.05 mg per square centimeter (mg $cm^{-2}$) and 20 mg $cm^{-2}$, more preferably is between 0.1 mg $cm^{-2}$ and 15 mg $cm^{-2}$ and even more preferably is between 0.5 mg cm$^{-2}$ and 10 mg cm$^{-2}$, in the case that the penentrant is applied on said nasal or other mucosa.

In another advantageous aspect of the invention, a kit containing said formulation in an amount which enables the formulation to be applied at the selected dose per area as afore-mentioned is provided.

It then is preferred if the formulation is contained in a bottle or any other packaging vessel.

The kit preferrably contains a device for administering the formulation.

According to another aspect of the present invention a patch is provided containing the formulation in an amount that yields the dose per area as mentioned above. The patch or transdermal patch according to the present invention is intended for the application to barriers including the skin, mucosa or plants. The term "transdermal" should include these aforesaid barriers.

Preferably the patch comprises
a non-occlusive backing liner;
an inner liner, wherein the backing liner and the inner liner define a reservoir; and/or a matrix layer.

It is preferred that said non-occlusive backing liner exhibits a mean vapor transmission rate (MVTR) of more than 1000 g/m$^2$day, preferably of more than 5.000 g/m$^2$day and most preferably of more than 10.000 g/m$^2$day. It is preferred that the non-occlusive backing liner has pores of smaller than 100 nm, preferably smaller than 70 nm, more preferably of smaller than 30 nm and most preferably as big as the intermolecular distances of the backing material. In a further preferred embodiment the non-occlusive backing liner comprises a polyurethane membrane, preferably a polyester track-etched porous membrane, more preferably a polycarbonate track-etched porous membrane and most preferably a polyethylene microporous membrane.

The inner liner and/or matrix layer according to the present invention establishes skin contact. The inner liner preferably prevents unwanted release of the formulation from the patch during storage and enables rapid skin wetting when contacted with the skin. According to the present invention it is further preferred that the inner liner comprises a homogeneous membrane, preferably a polyester track-etched porous membrane or a polycarbonate track-etched porous membrane. Moreover, these inner liner membranes preferably have a pore density of up to 5%, preferably of up to 15%, more preferably of up to 25% and most preferably of more than 25% and/or a pore size in the range between 20 rum and 200 nm, preferably between 50 nm and 140 nm and most preferably between 80 nm and 120 nm.

Further preferred inner liner materials comprise a hydrophobic mesh-membrane and/or a nonwoven fleece with mesh openings formed by hydrophobic threads. In another preferred embodiment the inner liner is a microporous polyethylene membrane having average pore sizes in the range of between 50 nm to 3000 nm, preferably between 500 nm to 2000 nm and most preferably of about 1500 nm.

According to a further preferred embodiment of the present invention the patch comprises a pressure sensitive adhesive layer, preferably an adhesive layer comprising polyacylate, polyisobutylene, silicone, ethylene vinyl acetate copolymer, polyvinylpyrrolidone or polyethylene oxide hydrogel.

According to another preferred feature of the present invention the formulation comprises penetrants having an average diameter of smaller than 150 nm, preferably of smaller than 100 nm. It is also preferred that the total dry weight of droplets in the formulation is at least 5 weight-% (w-%), preferably between 7.5 w-% and 30 w-%, and more preferably between 10 w-% and 20 w-%.

The patch according to the present invention preferably comprises a formulation, wherein the formulation up to maximally 200 mPas, more preferably up to 40 mPas, and most preferably up to 8 mPas.

The area of the drug releasing membrane is between 0.5 $cm^2$ and 250 $cm^2$, more preferably is between 1 $cm^2$ and 100 $cm^2$, even more preferably is between 2 $cm^2$ and 50 $cm^2$ and most preferred is between 4 $cm^2$ and 25 $cm^2$.

In an especially preferred embodiment it is preferred that the patch comprises one or more additional layers comprising desiccant containing layers, matrix layers, foam tape layers and/or protective layers.

The inventors found that it is advantageous to use backing liners having the capability to support the evaporation of the Transfersomes suspending medium. According to the present invention they preferably exhibit a mean vapor transmission rate (MVTR) of more than 1000 $g/m^2$day or, better, more than 10 000 $g/m^2$day. The solvent disappearance across such a barrier at sufficiently high rate helps to create and to maintain an activity gradient which drives the flux of Transfersome®-aggregates across a barrier.

Suited inventive backing liners are polyurethane membranes, such as CoTran 9701 (3M Medica, Borken Germany), Tegaderm (3M Medica, Borken Germany), Arcare 8311 (Adhesive Research, Limerick, Ireland), IV3000 (Smith and Nephew). Even better suited are polyester track-etched porous membranes (10 nm pore size) (Osmonics, Minnetonka, USA) and polycarbonate track-etched porous membranes (10 nm pore size) (Osmonics, Minnetonka, USA). Most suited are the polyethylene microporous membranes such as Cotran 9711 (3M Medica, Borken Germany), 14P01A, 10P05A, 8P07A, E011 D (DSM Solutech, Heerlen, The Netherlands). In classical TTS known in the art, the latter materials customary are used for rate controlling membranes.

Said backing liner need to be liquid-tight in order to prevent loss of active substance, which should be delivered erg. transdermally. In order to ensure or determine if the membrane is liquid-tight, the penetrability of Transfersomes® through the membranes is measured upon application of low hydrostatic pressures. The polyethylene membranes Cotran 9711 (3M Medica, Borken Germany) and 14P01A are liquid tight up to an applied pressure of 1 MPa. Further, all cited polyurethane membranes are liquid tight.

Another important feature of the patch according to the present invention is the use of an inner liner membrane instead-of conventional rate controlling membranes which enable rapid skin wetting with the Transfersome®-formulation, while blocking the (unwanted) release of the formulation during storage or during the application of the device on the skin. Since the present invention specifically is directed to Transfersome®-containing patches, the term "rate controlling membrane" is misleading, since the rate of Transfersome® mediated transport is ideally controlled by the water activity in and on the biological barrier. Thus, the term "inner liner" is used herein instead of "rate controlling membrane".

One inner liner membrane, which is suitable for the purpose of the present invention is a homogeneous membrane having a high pore density. The passage through the pores depends on the Laplace pressure/surface tension of lipid suspension within the pores $P_{min}=2\,\sigma\cos\theta/r$, where $P_{min}$ denotes the minimal pressure required to overcome the Laplace pressure, $\sigma$ is the surface tension of the suspension-air interface (~30 mN/m), $\theta$ is the contact angle of the formulation on the membrane material and r is the pore radius (~100 nm). Accordingly, retention of the formulation in the pores requires cos θ<0, which means that the membrane needs to be hydrophobic. According to this possible theory a Laplace pressure of 0.6 MPa is needed to move the air-suspension interface through the pores, thus enabling the suspension to cross the barrier.

Well suited inner liner membrane materials according to the present invention are polyester track-etched porous membranes (100 nm pore size) (Infiltec, Speyer, Germany) and polycarbonate track-etched porous membranes (100 nm pore size) (Infiltec, Speyer, Germany).

Morover, it is intended by the inventors to use hydrophobic mesh-membranes e.g. Fluortex 09/70/22, Fluortex 09/85/27 (INFILTEC, Speyer) and nonwoven fleeces e.g. Parafil R20, Parafil RK 20, Parafil R 30 Natur, Parafil RK 30, Paratherm PR 220/18, Paratherm PR 220/20 (LTS, Andernach, Germany). These sieving materials are well suited to act as inner liner in inventive patches.

Said liners constitute mesh openings built up by the hydrophobic threads. They prevent the passage of Transfersomes® when the liner is not in contact with the skin. The high contact angle γ of the air/water or air/Transfersome®-suspension interface, with respect to the hydrophobic surface of the thread, ensures this. The mesh openings allow for the passage of the Transfersomes® through the liner when contacting the skin. This is caused by the energy gained by the wetting of a more hydrophilic or of a less hydrophobic surface (e.g. the skin) exceeding the surface energy needed for the complete wetting of the threads.

In more concrete terms, said "switching-effect" can be explained as follows: Let d be the distance between two threads from midpoint to midpoint. Let r be the radius of a thread:

$$2\pi rz\gamma_{wt}\approx zd\gamma_{ws}$$

The surface tension of water on the skin is $\gamma_{ws}$=40 m N/nm according to "Transdermal and Drug Delivery Systems", Buffalo Grove, Interpharm Press, Ghosh, Pfister et al. 1997. The surface tension of water on the hydrophobic thread is $\gamma_{wt}$=70 m N/m. (The surface tension of a suspension on skin is again $\gamma_{ws}$=40 m N/m, the surface tension of the suspension on the hydrophobic thread is $\gamma_{wt}$=35 m N/m, due to the presence of a detergent monolayer). Rearranging the above formula yields $$2\pi r/d\approx\gamma_{ws}/\gamma_{wt}$$

for the case of the suspension ($\gamma_{ws}$~$\gamma_{wt}$). This suggests that the thread radius to mesh size ratio should preferably be in the range of about 0.3.

According to the present invention it is especially preferred to use microporous polyethylene membranes as inner liner. The term "microporous" for the purposes of the present invention means pore sizes of at least 20 nm preferably in the range between 50 nm to 3000 nm. Examples are Solupor-E011 D (mean pore size 1500 nm), Solupor-8P07A (mean pore size 700 nm) and Solupor-10P05A (mean pore size 500 nm) (DSM Solutech, Heerlen, The Netherlands), which exhibit a high penetrability at small pressures thus allowing for Transfersomes to wet the skin upon contact.

For all types of the above mentioned inner liner membranes the surface tension, σ, and the contact angle, γ, are changed when contacted with the skin There are various factors, which can cause said changes of the surface tension, σ, and the contact angle, γ. One factor may be an increase in humidity and capillary condensation of transepidermally released water. Hydrophilic bridging due to interaction between corneocytes/hair follicles and the inner membrane may also contribute to rapid skin wetting. Finally, hydrophilisation of the pore core by contaminants, such as microscopic skin fragments, may alter the surface tension, σ, and the contact angle, γ. As a consequence, the minimal pressure $P_{min}$, which is required to overcome the Laplace pressure, is reduced and the formulation can pass the inner liner and wet the skin surface.

Patches according to the present invention can be manufactured by different methods known in the art. On principle the lamination of the backing and the inner liner can be carried out by heat lamination or adhesive lamination or any other known lamination method.

In heat lamination processes the liners are adhered by melting at least one material at elevated temperatures and elevated pressures for short periods. The melt(s) merge and intercalate upon cooling and consolidation. The temperature and pressure is applied by metallic chops, either pulse heated, e.g. by microwave radiation, or continuously heated. Polyethylene and polyurethan membranes typically are heat laminated at temperatures of 120-200° C., preferably of 140-160° C. and pressures of 1-6 bar, preferably of 3-4 bar. Good lamination properties are achieved for Tranfersom® containing patches by applying a pressure of 4 bar for a period of about 0.1-5 seconds, preferably of about 1-2 seconds.

Adhesive lamination of the liners is achieved by a layer of pressure sensitive adhesive such as polyacylate, polyisobutylene, silicone, ethylene vinyl acetate copolymer or polyvinylpyrrolidone and polyethylene oxide hydrogel adhesive (PVP/PEO). The adhesive liner is precut to the appropiate shape for example a concentric ring having a width of 1 cm. The backing and the inner liners are laminated to the ring and the patch is punched out of the web. Suitable films are for example a pressure sensitive transfer film (Arcare 7396), a flexible plastic film coated on both sides with a medical grade pressure sensitive adhesive (Arcare 8570 clear polyester) or foam tapes (Polyolefin 3M 1777; 3M 1779; 3M 9751, polyvinyl chloride 3M 9772L) coated on both sides with pressure sensitive acrylate adhesive. The latter example mounts a reservoir of defined volume due to the finite thickness of the foam tape, while the former two examples draw their Transfersome® containing volume by the elasticity and/or hidden area of the liners.

The filling of the one compartment reservoir type patch according to the present invention can be achieved by several methods known in the art.

One possible filling procedure is based on a two-step lamination process. In the first step, the main compartment is laminated while retaining a small orifice. Through this port a tap or a tubing is induced and the Transfersome® formulation is injected into the preformed reservoir. After retraction of the tap or tubing the lamination of the port is finalized. Heat lamination as well as adhesive lamination can be used in said procedure. In the case of heat lamination the heat chop laminates a C-shaped ring. After the filling of the inner part of the C, the heat chop is revolved by 45° and the heat lamination is repeated a second time now closing the open part of the C. In the case of adhesive lamination the release liner of the transfer tape is not removed completely thus allowing for the establishment of the filling port. After filling the rest of the release liner is removed and the port is sealed. Back-folding of the backing and/or the inner liner leads to the same result: A collar-like port is formed, which is sealed by refolding the membranes after the filling process.

The form, fill and seal technique is well established and can also be used for the manufacture of the patches according to the present invention. In a first step the film for the backing liner is moved over a trough of desired dimensions. The liner adopts this shape under vacuum and lines the trough. Then a tap fills the Transfersome® formulation into the trough. After the tap is retracted the inner liner membrane is applied onto the web. A concentric seal ring laminates both films either by heat lamination or adhesive lamination as described above.

In a further suitable process for making TTS the Transfersome® formulation is injected through a preinstalled tubing after the lamination process. The tubing is laterally inserted into the foam in the same way as a venous catheter is set for continuous injection. The tubing is connected to a Transfersome®-formulation filled syringe by a luer lock. The desired amount of formulation is injected into the reservoir and the tubing is removed and/or sealed if necessary.

In another important aspect of the present invention a patch is provided which is further characterised in that the patch comprises at least two compartments, which are separated from each other during storage. According to another aspect of the present invention a patch is provided containing the formulation in an amount that yields the dose per area as mentioned above, wherein the patch comprises several, more preferably less than 5, even more preferably 3, and most preferred 2 separate inner compartments which are combined prior to or during the application of the formulation. Preferably at least one of the compartments is inside and/or outside the patch.

It is preferred that the formulation and/or the individual formulation components and/or the agent and/or the suspension/dispersion of penetrants without the agent are kept during the storage in several, preferably less than 5, more preferably in 3, and most preferred in 2 separate compartments of the patch which, in case, are combined prior to or during or after the application of the patch.

In another preferred embodiment the outer compartments comprise injection systems, preferably syringes, which are connected to the reservoir of the patch. It is preferred that the compartments are vertically stacked and/or are arranged side-by-side and/or one compartment is included in a second compartment, preferably without being fixed to the second compartment.

Preferably the compartments are inside the reservoir, which is defined by the backing liner and the inner liner. It is further preferred that the compartments are separated from each other by a controllably openable barrier, preferably a membrane and/or by a plug and/or by a compartment-forming lamination.

According to the present invention combining and mixing of the ingredients of the compartments is achieved by direct mechanical action, such as pressing, rubbing, kneading, twisting, tearing and/or indirectly by changing the temperature, osmotic pressure or electrical potential, thereby causing the removal or destroying of the separating barrier(s).

In a further preferred embodiment of the present invention the patch comprises
- an inventive non-occlusive backing liner
- a membrane defining a reservoir, which is divided in at least two compartments,
- wherein the formulation directly contacts the skin when the formulation releases from the reservoir or compartments.

The inventive multicompartment reservoir-type patch comprises at least two separate compartments and a mixing compartment, wherein said mixing compartment may be an storage compartment containing one ingredient of the formulation or the formulation or may be an compartment, which is not filled during the storage period.

According to the present invention the storage compartments containing the critical ingredients may be separated from the mixing compartment. The storage compartments are containing some, if not all, ingredients during the storage period after preparation and prior to application. The mixing compartment serves to mix the separated ingredients after the storage period. After mixing the formulation is released onto the skin from the mixing compartment. The mixing compartment may have an adjustable area of skin contact to allow for area-dose control. This can be done by the merger of smaller subunits of mixing compartments.

The mixing compartment has to be in contact with the skin. This can be achieved either by
1. direct contact with the skin (no inner liner membrane) or
2. an inner liner membrane according to the present invention. Reference is made to the one-compartment patch described above. The identical inner liner membranes may be used for multicompartment TTS.

The number of storage compartments may be at least two and is depending on the respective longterm-incompatibilities of the ingredients.

The storage compartments may be part of the patch and may be made of the same material(s). The storage compartments may be—in the simplest form—two syringes containing the liquid ingredients, which are injected sequentially or simultaneously into the mixing chamber through one ore more tubes. A twin-syringe of which the two pistons are connected facilitates simultaneous injection and constancy of the ingredients ratio. An additional tubing ideally with micro-arcs as used in HPLC sample preparation may cause turbulences of the merged liquid. A T-piece connector, ideally with turbulence chamber serves in the same manner. Thus, an optimal mixing of the components is achieved even at high viscosities and high lipid-concentrations.

The mixing compartment according to the present invention may be one separate compartment which is empty during storage but filled almost simultaneously, when the patch is applied onto the skin, or it may be one of the existing storage compartments in which the other ingredients are being added from other storage compartments, or it may be created by the merger of two or more storage compartments.

The combining or mixing of the ingredients can be achieved by perforating or destroying the compartment-separating membranes. This can be done, for example, by pressing or kneading the patch such that the compartment-separating membranes rupture upon this mechanical stress, or by the external or internal activation of a sharp tool, such as a needle by perforating the compartment-separating membrane.

Another method combining or mixing of the ingredients is based on opening a tube-system between the compartments. Said opening can be achieved e.g. by pressing or kneading the patch such that plug or squid which close the tubing between the separated compartments during the storage-period is released from the tubing due to the applied pressure.

It is also possible according to present invention to combine and mix the ingredients by unsealing of a lamination, which forms the separated storage compartments. This can be done, for example, by applying a small but a steady-state pressure onto the filled storage chambers, but also by heat lamination or adhesive lamination. The lamination of the compartment-forming membranes unseals and the liquids squeeze through the self-formed channels into the mixing compartment.

The storage and mixing compartments may be stacked vertically or placed side-by-side. For example, three membranes can be laminated in a manner that half of the middle membrane is sealed to the lower (e.g. inner liner) membrane and the other half is sealed to the upper membrane (backing liner). Upper and lower membranes are sealed at the edges on the very right, very left, forward-turned and backward-turned sides thus forming a two-compartment pouch. The middle membrane might be impermeable to liquids, but also easy to disrupt. Suitable materials for middle membranes might be e.g. thin polyurethanes. According to one possible embodiment the storage container for the Transfersomes®-formulation may be the left liquid-tight compartment, while the Transfersome®-release is performed from the right chamber through the inventive inner liner membrane when contacted to the skin. The right chamber may serve e.g. as a storage compartment for (lyophilized) drug(s). It is clear to someone skilled in the art that also combinations of the aforementioned embodiments, e.g. a combination of the vertical stacking and side-by-side alignment are suitable for the purposes of the present invention.

After the mixing process in the mixing compartment the emptied storage compartments are dispensable. They may be unplugged (in the case of external compartments, such as syringes) or clipped off. For example the tubes may be detached and the ports may be sealed with tape or squids or plugs. Open sealing may be re-laminated by applying pressure.

It another important aspect of the present invention, a method is provided of administering an agent to a mammalian body or a plant, by transporting said agent through a barrier, wherein the barrier is the intact skin, mucosa and/or cuticle of said mammalian body or a plant, said agent being associated to a penetrant capable of transporting said agent through the skin pores or through the passages in mucosa or cuticle, or capable of enabling agent permeation through skin pores after said penetrant has opened and/or entered said pores, comprising the steps of:

preparing a formulation by suspending or dispersing said penetrants in a polar liquid in the form of fluid droplets surrounded by a membrane-like coating of one or several layers, said coating comprising at least two kinds or forms of amphiphilic substances with a tendency to aggregate, provided that said at least two substances differ by at least a factor of 10 in solubility in said polar liquid, and/or said substances when in the form of homo-aggregates (for the more soluble substance) or of hetero-aggregates (for any combination of both said substances) have a preferred average diameter smaller than the diameter of homo-aggregates containing merely the less soluble substance, and/or the more soluble substance tends to solubilise the droplet and the content of such substance is to up to 99 mol-% of solubilising concentration or else corresponds to up to 99 mol-% of the saturating concentration in the unsolubilised droplet, whichever is higher, and/or the presence of the more soluble substance lowers the average elastic energy of the membrane-like coating to a value at least 5 times lower, more preferably at least 10 times lower and most preferably more than 10 times lower, than the average elastic energy of red blood cells or of phospholipid bilayers with fluid aliphatic chains, said penetrants being able to transport agents through the pores of said barrier or being able to promote agent permeation through the pores of said skin after penetrants have entered the pores, selecting a dose amount of said penetrants to be applied on a predetermined area of said barrier to control the flux of said penetrants across said barrier, and applying the selected dose amount of said formulation containing said penetrants onto said area of said porous barrier.

It then is preferred if the flux across said barrier is increased by enlarging the applied dose amount of said penetrants per area of barrier.

The pH of the formulation preferably is chosen to be between 3 and 10, more preferably is between 4 and 9, and most preferably is between 5 and 8.

In this aspect of the invention, it then is preferred if the formulation comprises:

at least one thickening agent in an amount to increase the formulation viscosity to maximally 5 Nm/s, more preferably up to 1 Nm/s, and most preferably up to 0.2 Nm/s, so that formulation spreading-over, and drug retention at the application area is enabled, and/or at least one antioxidant in an amount that reduces the increase of oxidation index to less than 100% per 6 months, more preferably to less than 100% per 12 months and most preferably to less than 50% per 12 months and/or at least one microbicide in an amount that reduces the bacterial count of 1 million germs added per g of total mass of the formulation to less than 100 in the case of aerobic bacteria, to less than 10 in the case of entero-bacteria, and to less than 1 in the case of *Pseudomonas aeruginosa* or *Staphilococcus aureus*, after a period of 4 days.

Said at least one microbicide then preferably is added in an amount that reduces the bacterial count of 1 million germs added per g of total mass of the formulation to less than 100 in the case of aerobic bacteria, to less than 10 in the case of entero-bacteria, and to less than 1 in the case of *Pseudomonas aeruginosa* or *Staphilococcus aureus*, after a period of 3 days, and more preferably after a period of 1 day.

Said thickening agent preferably is selected from the class of pharmaceutically acceptable hydrophilic polymers, such as partially etherified cellulose derivatives, like carboxymethyl-, hydroxyethyl-, hydroxypropyl-, hydroxypropylmethyl- or methyl-cellulose; completely synthetic hydrophilic polymers such as polyacrylates, polymethacrylates, poly(hydroxyethyl)-, poly(hydroxypropyl)-, poly(hydroxypropylmethyl)methacrylates, polyacrylonitriles, methallyl-sulphonates, polyethylenes, polyoxiethylenes, polyethylene glycols, polyethylene glycol-lactides, polyethylene glycol-diacrylates, polyvinylpyrrolidones, polyvinyl alcohols, poly(propylmethacrylamides), poly(propylene fumarate-co-ethylene glycols), poloxamers, polyaspartamides, (hydrazine cross-linked) hyaluronic acids, silicones; natural gums comprising alginates, carrageenans, guar-gums, gelatines, tragacanths, (amidated) pectins, xanthans, chitosan collagens, agaroses; mixtures and further derivatives or co-polymers thereof and/or other pharmaceutically, or at least biologically, acceptable polymers.

The concentration of said polymer then preferably is chosen to be in the range between 0.01 w-% and 10 w-%, more preferably in the range between 0.1 w-% and 5 w-%, even more preferably in the range between 0.25 w-% and 3.5 w-% and most preferably in the range between 0.5 w-% and 2 w-%.

According to the invention said anti-oxidant then preferably is selected from synthetic phenolic antioxidants, such as butylated hydroxyanisol (BHA), butylated hydroxytoluene (BHT ) and di-tert-butylphenol (LY178002, LY256548, HWA-131, BF-389, CI-986, PD-127443, E-5119, BI-L-239XX, etc.), tertiary butylhydroquinone (TBHQ), propyl gallate (PG), 1-O-hexyl-2,3,5-trimethylhydroquinone (HTHQ); aromatic amines (such as diphenylamine, p-alkylthio-o-anisidine, ethylenediamine derivatives, carbazol, tetrahydroindenoindol); phenols and phenolic acids (such as guaiacol, hydroquinone, vanillin, gallic acids and their esters, protocatechuic acid, quinic acid, syringic acid, ellagic acid, salicylic acid, nordihydroguaiaretic acid (NDGA), eugenol); tocopherols (including tocopherols (alpha, beta, gamma, delta) and their derivatives, such as tocopheryl-acylate (e.g. -acetate, -laurate, myristate, -palmitate, -oleate, -linoleate, etc., or any other suitable tocopheryl-lipoate), tocopheryl-POE-succinate; trolox and corresponding amide- and thiocarboxamide analogues; ascorbic acid and its salts, isoascorbate, (2 or 3 or 6)-o-alkylascorbic acids, ascorbyl esters (e.g. 6-o-lauroyl, myristoyl, palmitoyl-, oleoyl, or linoleoyl-L-ascorbic acid, etc.); non-steroidal anti-inflammatory agents (NSAIDs), such as indomethacin, diclofenac, mefenamic acid, flufenamic acid, phenylbutazone, oxyphenbutazone acetylsalicylic acid, naproxen, diflunisal, ibuprofen, ketoprofen, piroxicam, penicillamine, penicillamine disulphide, primaquine, quinacrine, chloroquine, hydroxychloroquine, azathioprine, phenobarbital, acetaminephen); aminosalicylic acids and derivatives; methotrexate, probucol, antiarrhythmics (e.g. amiodarone, aprindine, asocainol), ambroxol, tamoxifen, b-hydroxytamoxifen; calcium antagonists (such as nifedipine, nisoldipine, nimodipine, nicardipine, nilvadipine), beta-receptor blockers (e.g. atenolol, propranolol, nebivolol); sodium bisulphite, sodium metabisulphite, thiourea; chelating agents, such as EDTA, GDTA, desferral; endogenous defence systems, such as transferrin, lactoferrin, ferritin, cearuloplasmin, haptoglobion, haemopexin, albumin, glucose, ubiquinol-10; enzymatic antioxidants, such as superoxide dismutase and metal complexes with a similar activity, including catalase, glutathione peroxidase, and less complex molecules, such as beta-carotene, bilirubin, uric acid; flavonoids (e.g. flavones, flavonols, flavonones, flavanonals, chacones, anthocyanins), N-acetylcystein, mesna, glutathione, thiohistidine derivatives, triazoles; tannines, cinnamic acid, hydroxycinnamatic acids and their esters (e.g. coumaric acids and esters, caffeic acid and their esters, ferulic acid, (iso-) chlorogenic acid, sinapic acid); spice extracts (e.g. from clove, cinnamon, sage, rosemary, mace, oregano, allspice, nutmeg); carnosic acid, carnosol, carsolic acid; rosmarinic acid, rosmarindiphenol, gentisic acid, ferulic acid; oat flour extracts, such as avenanthramide 1 and 2; thioethers, dithioethers, sulphoxides, tetralkylthiuram disulphides; phytic acid, steroid derivatives (e.g. U74006F); tryptophan metabolites (e.g. 3-hydroxykynurenine, 3-hydroxyanthranilic acid), and organochalcogenides, or else is an oxidation suppressing enzyme.

It then is preferred if the concentration of BHA or BHT is between 0.001 and 2 w-%, more preferably is between 0.0025 and 0.2 w-%, and most preferably is between 0.005 and 0.02 w-%, of TBHQ and PG is between 0.001 and 2 w-%, more preferably is between 0.005 and 0.2 w-%, and most preferably is between 0.01 and 0.02 w-%, of tocopherols is between 0.005 and 5 w-%, more preferably is between 0.01 and 0.5 w-%, and most preferably is between 0.05 and 0.075 w-%, of ascorbic acid esters is between 0.001 and 5, more preferably is between 0.005 and 0.5, and most preferably is between 0.01 and 0.15 w-%, of ascorbic acid is between 0.001 and 5, more preferably is between 0.005 and 0.5 w-%, and most preferably is between 0.01 and 0.1 w-%, of sodium bisulphite or sodium metabisulphite is between 0.001 and 5, more preferably is between 0.005 and 0.5 w-%, and most preferably is between 0.01-0.15 w-%, of thiourea is between 0.0001 and 2 w-%, more preferably is between 0.0005 and 0.2, and most preferably is between 0.001-0.01 w-%, most typically 0.005 w-%, of cystein is between 0.01 and 5, more preferably is between 0.05 and 2 w-%, and most preferably is between 0.1 and 1.0 w-%, most typically 0.5 w-%, of monothioglycerol is between 0.01 and 5 w-%, more preferably is between 0.05 and 2 w-%, and most preferably is between 0.1-1.0 w-%, most typically 0.5 w-%, of NDGA is between 0.0005-2 w-%, more preferably is between 0.001-0.2 w-%, and most preferably is between 0.005-0.02 w-%, most typically 0.01 w-%, of glutathione is between 0.005 and 5 w-%, more preferably is between 0.01 and 0.5 w-%, and most preferably is between 0.05 and 0.2 w-%, most typically 0.1 w-%, of EDTA is between 0.001 and 5 w-%, even more preferably is between 0.005 and 0.5 w-%, and most preferably is between 0.01 and 0.2 w-%, most typically between 0.05 and 0.975 w-%, of citric acid is between 0.001 and 5 w-%, even more preferably is between 0.005 and 3 w-%, and most preferably is between 0.01-0.2, most typically between 0.3 and 2 w-%.

Preferably said microbicide is then selected amongst short chain alcohols, such as ethyl and isopropyl alcohol, chlorbutanol, benzyl alcohol, chlorbenzyl alcohol, dichlorbenzylalcohol; hexachlorophene; phenolic compounds, such as cresol, 4-chloro-m-cresol, p-chloro-m-xylenol, dichlorophene, hexachlorophene, povidon-iodine; parabens, especially alkyl-paraben, such as methyl-, ethyl-, propyl-, or butyl-paraben, benzyl-paraben; acids, such as sorbic acid, benzoic acid and its salts; quaternary ammonium compounds, such as alkonium salts, e.g. benzalkonium salts, especially the chlorides or bromides, cetrimonium salts, e.g. the bromide; phenoalkecinium salt, such as phenododecinium bromide, cetylpyridinium chloride or other such salts; mercurium compounds, such as phenylmercuric acetate, borate, or nitrate, thiomersal; chlorhexidine or its gluconate; antibiotically active compounds of biological origin, or a mixture thereof.

It then is preferred that the bulk concentration of short chain alcohols in the case of ethyl, propyl, butyl or benzyl alcohol is up to 10 w-%, more preferably is up to 5 w-%, and most preferably is in the range between 0.5-3 w-%, and in the case of chlorobutanol is in the range between 0.3-0.6 w-%; bulk concentration of parabens, especially in the case of methyl paraben is in the range between 0.05-0.2 w-%, and in the case of propyl paraben is in the range between 0.002-0.02 w-%; bulk concentration of sorbic acid is in the range between 0.05-0.2 w-%, and in the case of benzoic acid is in the range between 0.1-0.5 w-%; bulk concentration of phenols, triclosan, is in the range between 0.1-0.3 w-%, and bulk concentration of chlorhexidine is in the range between 0.01-0.05 w-%.

It then is also preferred that the less soluble amongst the aggregating substances is a lipid or lipid-like material, especially a polar lipid, whereas the substance which is more soluble in the suspending liquid and which lowers the average elastic energy of the droplet is a surfactant or else has surfactant-like properties and/or is a form of said lipid or lipid-like material which is comparably soluble as said surfactant or the surfactant-like material.

Preferably the lipid or lipid-like material is a lipid or a lipid from a biological source or a corresponding synthetic lipid or any of its modifications, said lipid preferably belonging to the class of pure phospholipids corresponding to the general formula

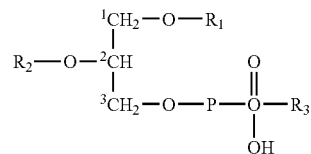

where $R_1$ and $R_2$ is an aliphatic chain, typically a $C_{10-20}$-acyl, or -alkyl or partly unsaturated fatty acid residue, in particular, an oleoyl-, palmitoeloyl-, elaidoyl-, linoleyl-, linolenyl-, linolenoyl-, arachidoyl-, vaccinyl-, lauroyl-, myristoyl-, palmitoyl-, or stearoyl chain; and where $R_3$ is hydrogen, 2-trimethylamino-1-ethyl, 2-amino-1-ethyl, $C_{1-4}$-alkyl, $C_{1-5}$-alkyl substituted with carboxy, $C_{2-5}$-alkyl substituted with hydroxy, $C_{2-5}$-alkyl substituted with carboxy and hydroxy, or $C_{2-5}$-alkyl substituted with carboxy and amino, inositol, sphingosine, or salts of said substances, said lipid comprising also glycerides, isoprenoid lipids, steroids, sterines or sterols, of sulphur- or carbohydrate-containing lipids, or any other bilayer-forming lipids, in particular half-protonated fluid fatty acids, said lipid is selected from the group comprising phosphatidylcholines, phosphatidylethanolamines, phosphatidylglycerols, phosphatidylinositols, phosphatidic acids, phosphatidylserines, sphingomyelins or other sphingophospholipids, glycosphingolipids (including cerebrosides, ceramidepolyhexosides, sulphatides, sphingoplasmalogens), gangliosides and other glycolipids or synthetic lipids, in particular with corresponding sphingosine derivatives, or any other glycolipids, whereby two similar or different chains can be ester-groups-linked to the backbone (as in diacyl and dialkenoyl compound) or be attached to the backbone with ether bonds, as in dialkyl-lipids.

The surfactant or surfactant-like material preferably is a nonionic, a zwitterionic, an anionic or a cationic surfactant, especially a fatty-acid or -alcohol, an alkyl-tri/di/methyl-ammonium salt, an alkylsulphate salt, a monovalent salt of cholate, deoxycholate, glycocholate, glycodeoxycholate, taurodeoxycholate, taurocholate, etc., an acyl- or alkanoyl-dimethyl-aminoxide, esp. a dodecyl-dimethyl-aminoxide, an alkyl- or alkanoyl-N-methylglucamide, N-alkyl-N,N-dimethylglycine, 3-(acyldimethylammonio)-alkanesulphonate, N-acyl-sulphobetaine, a polyethylene-glycol-octylphenyl ether, esp. a nonaethylene-glycol-octylphenyl ether, a polyethylene-acyl ether, esp. a nonaethylen-dodecyl ether, a polyethylene-glycol-isoacyl ether, esp. a octaethylene-glycol-isotridecyl ether, polyethylene-acyl ether, esp. octaethylenedodecyl ether, polyethylene-glycol-sorbitane-acyl ester, such as polyethylenglykol-20-monolaurate (Tween 20) or polyethylenglykol-20-sorbitan-monooleate (Tween 80), a polyhydroxyethyleneacyl ether, esp. polyhydroxyethylene-lauryl, -myristoyl, -cetylstearyl, or -oleoyl ether, as in polyhydroxyethylene-4 or 6 or 8 or 10 or 12, etc., -lauryl ether (as in Brij series), or in the corresponding ester, e.g. of polyhydroxyethylen-8-stearate (Myrj 45), -laurate or -oleate type, or in polyethoxylated castor oil 40, a sorbitane-monoalkylate (e.g. in Arlacel-or Span), esp. sorbitane-mono-laurate, an acyl- or alkanoyl-N-methylglucamide, esp. in or decanoyl- or dodecanoyl-N-methylglucamide, an alkyl-sulphate (salt), e.g. in lauryl- or oleoyl-sulphate, sodium deoxycholate, sodium glycodeoxycholate, sodium oleate, sodium taurate, a fatty acid salt, such as sodium elaidate, sodium linoleate, sodium laurate, a lysophospholipid, such as n-octadecylene(=oleoyl)-glycerophosphatidic acid, -phosphorylglycerol, or -phosphorylserine, n-acyl-, e.g. lauryl or oleoyl-glycero-phosphatidic acid, -phosphorylglycorol, or -phosphorylserine, n-tetradecyl-glycero-phosphatidic acid, -phosphorylglycerol, or -phosphorylserine, a corresponding palmitoeloyl-, elaidoyl-, vaccenyl-lysophospholipid or a corresponding short-chain phospholipid, or else a surface-active polypeptide.

The average diameter of the penetrant preferably is between 30 nm and 500 nm, more preferably between 40 nm and 250 nm, even more preferably between 50 nm and 200 nm and particularly preferably between 60 nm and 150 nm.

The total dry weight of droplets in a formulation is then preferably chosen to range from 0.01 weight-% (w-%) to 40 w-% of total formulation mass, more preferably is between 0.1 w-% and 30 w-%, and most preferably is between 0,5 w-% and 20 w-%.

Preferably the total dry weight of droplets in a formulation is selected to increase the formulation viscosity to maximally 200 mPas, more preferably up to 40 mPas, and most preferably up to 8 mPas.

Preferably at least one edge-active substance or surfactant and/or at least one amphiphilic substance, and/or at least one hydrophilic fluid and the agent are mixed, if required separately, to form a solution, the resulting (partial) mixtures or solutions are then combined subsequently to induce, preferably by action of mechanical energy such as shaking, stirring, vibrations, homogenisation, ultrasonication, shearing, freezing and thawing, or filtration using convenient driving pressure, the formation of penetrants that associate with and/or incorporate the agent It also is preferred if said amphiphilic substances then are dissolved in volatile solvents, such as alcohols, especially ethanol, or in other pharmaceutically acceptable organic solvents, such as ethanol, 1- and 2-propanol, benzyl alcohol, propylene glycol, polyethylene glycol (molecular weight: 200-400 D) or glycerol, other pharmaceutically acceptable organic solvents, such as undercooled gas, especially supercritical $CO_2$, which are then removed, especially by evaporation or dilution, prior to making the final preparation.

The formation of said penetrants then preferrably is induced by the addition of required substances into a fluid phase, evaporation from a reverse phase, by injection or dialysis, if necessary under the influence of mechanical stress, such as shaking, stirring, especially high velocity stirring, vibrating, homogenising, ultrasonication, shearing, freezing and thawing, or filtration using a convenient, especially low (1 MPa) or intermediate (up to 10 MPa), driving pressure.

It then is also preferred if the formation of said penetrants is induced by filtration, the filtering material having pores sizes between 0.01 μm and 0.8 μm, more preferably between 0.02 μm and 0.3 μm, and most preferably between 0.05 μm and 0.15 μm, whereby several filters may be used sequentially or in parallel.

Said agents and penetrants are made to associate, at least partly, after the formation of said penetrants, e.g. after injecting a solution of the drug in a pharmaceutically acceptable fluid, such as ethanol, 1- and 2-propanol, benzyl alcohol, propylene glycol, polyethylene glycol (molecular weight: 200-400 D) or glycerol into the suspending medium, simultaneously with penetrant formation, if required using the drug co-solution and, at least some, penetrant ingredients.

It then is preferred if said penetrants, with which the agent is associated, are prepared immediately before the application of the formulation, if convenient, from a suitable concentrate or a lyophylisate.

Accordingly the formulation is applied by spraying, smearing, rolling or sponging on the application area, in particular by using a metered sprayer, spender, roller or a sponge, or a non-occlusive patch, as appropriate.

It further is preferred if the barrier is skin or at least partly keratinised endothelium and/or nasal or any other mucosa.

The area dose of said penetrant then preferrably is between 0.1 mg per square centimeter (mg $cm^{-2}$) and 40 mg $cm^{-2}$, more preferably is between 0.25 mg $cm^{-2}$ and 30 mg $cm^{-2}$ and even more preferably is between 0.5 mg $cm^{-2}$ and 15 mg cm$^{-2}$, in the case that the penentrant is applied on said skin and/or said at least partly keratinised endothelium.

The area dose of said penetrant preferably is between 0.05 mg per square centimeter (mg cm$^{-2}$) and 20 mg cm$^{-2}$, more preferably is between 0.1 mg cm$^{-2}$ and 15 mg cm$^{-2}$ and even more preferably is between 0.5 mg cm$^{-2}$ and 10 mg cm$^{-2}$, in the case that the penentrant is applied on said nasal or other mucosa.

The area dose of said penetrant preferrably is between 0.0001 mg per square centimeter (mg cm$^{-2}$) and 0.1 mg cm$^{-2}$, more preferrably is between 0.0005 mg cm$^{-2}$ and 0.05 mg cm$^{-2}$ and even more preferrably is between 0.001 mg cm$^{-2}$ and 0.01 mg cm$^{-2}$, in the case that the penetrant is applied on plant body, plant leaves or plant needles.

It is preferred if the method is used for generating an immune response on a human or other mammal by vaccinating said mammal.

It is preferred if the method is used for generating a therapeutic effect in a human or other mammal.

According to the present invention the above mentioned method is preferably used for the treatment of inflammatory disease, dermatosis, kidney or liver failure, adrenal insufficiency, aspiration syndrome, Behcet syndrome, bites and stings, blood disorders, such as cold-haemagglutinin disease, haemolytic anemia, hypereosinophilia, hypoplastic anemia, macroglobulinaemia, trombocytopenic purpura, furthermore, for the management of bone disorders, cerebral oedema, Cogan's syndrome, congenital adrenal hyperplasia, connective tissue disorders, such as lichen, lupus erythematosus, polymyalgia rheumatica, polymyositis and dermatomyositis, epilepsy, eye disorders, such as cataracts, Graves' ophthalmopathy, haemangioma, herpes infections, neuropathies, retinal vasculitis, scleritis, for some gastro-intestinal disorders, such as inflammatory bowel disease, nausea and oesophageal damage, for hypercalcaemia, infections, e.g. of the eye (as in infections mononucleosis), for Kawasaki disease, myasthenia gravis, various pain syndromes, such as postherpetic neuralgia, for polyneuropathies, pancreatitis, in respiratory disorders, such as asthma, for the management of rheumatoid disease and osteoarthritis, rhinitis, sarcoidosis, skin diseases, such as alopecia, eczema, erythema multiforme, lichen, pemphigus and pemphigoid, psoriasis, pyoderma gangrenosum, urticaria, in case of thyroid and vascular disorders.

Without any limitation of the scope of the present invention as defined by the attached claims the invention shall now be described in more detail by referring to the following examples and figures only showing non-limiting embodiments of the present invention.

General Experimental Set-up and Sample Preparation

Figure 1:
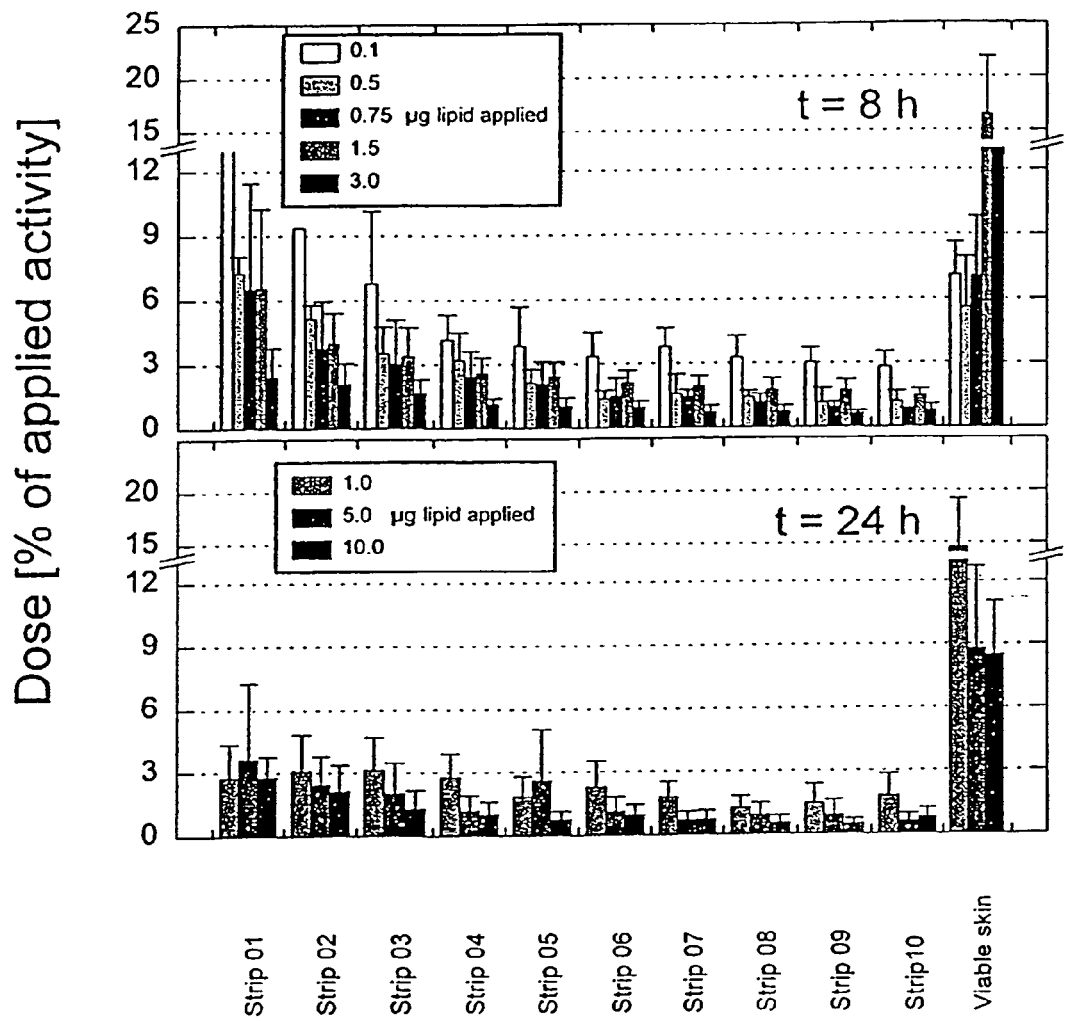
FIG. 1 shows the recovery of relative activity (penetrant amount) in different layers of the skin as a function of applied activity (dose).

Test formulation. Highly adaptable aggregate droplets used within the framework of this work had the form of (oligo)bilayer vesicles. Typically, the test formulation contained biocompatible (phospho)lipids, such as phosphatidylcholine, and (bio)surfactants, such as sodium cholate or polysorbate (Tween 80). Different phospholipid/detergent ratios have been chosen to maintain or select the highest possible aggregate deformability.

Manufacturing was done as described in previous applications of the applicant. In short, a solution of phosphatidylcholine (SPC; Natterman Phospholipids, Cologne, Germany) in chloroform was labelled with the tritiurated SPC (Amersham, XXX) and mixed with sodium cholate (Merck, Darmstadt, Germany) to obtain a phospholipid/detergent ratio of 3.75/1 (mol/mol). The mixture was dispersed in phosphate buffer (pH=7.2) to yield a 10 w-% total lipid suspension.

Vesicles in the suspension were frozen and thawed three times. Subsequently, the formulation was passed under pressure through several micro-porous filters (first 200 nm; then 100 nm, and finally 50 nm or 80 nm; Poretics, Calif.). To check the reproducibility of vesicle manufacturing, the average size of vesicles was measured with dynamic light scattering procedure and found to be in the range of 80 nm to 150 nm.

Test animals. Mice of NMRI strain were 8 to 12 weeks old at the time of experimentation. They had free access to standard chow and water and were kept in suspension cages in groups of 4 to 6. Prior to test formulation administration, the application area on each animals back was shaved carefully. The test preparation was administered under general anaesthesia (0.3 mL per mouse of an isotonic NaCl solution containing 0.0071% Rompun (Bayer, Leverkusen, Germany) and 14.3 mg/mL Ketavet (Parke-Davis, Rochester, N.Y). The administration was done with a high precision pipette on the skin which was left non-occluded. Each animal was finally transferred into an individual cage where it was kept for a day. A different cage was used for each animal for at least 24 hrs. 4 animals were used per test group.

Test measurements. Blood samples were collected from tail end, after termination of experiment at least. In one set of experiments, the early blood sampling was done every 2 hrs. Organ samples included: liver, spleen, kidney, and skin. The latter was also inspected superficially, by taking 10 strips (using a Tesa-Film).

Processing the organ samples was done according to standard procedures: for 3H-measurement, a small part of each organ and 100 μL of the carcass lysate were used to get the desired and quoted experimental data. These were analysed according to the standard procedures.

To determine total label recovery, the carcass of test animals was dissolved and discharged by addition of 50 mL perchloric acid Recovery (% of applied activity) was determined and the recovered doses (% of applied activity per organ) as well as the total delivered amount [μg lipid/g organ] were calculated.

EXAMPLES 1-5

Short Term Administration
Highly adaptable complex droplets (ultradeformable vesicles; Transfersomes)
87.4 mg phosphatidylcholine from soy bean (SPC)
12.6 mg sodium cholate (NaChol)
trace amount of $^3$H-DPPC with specific activity: 750 μCi/500 μL
0.9 mL phosphate buffer, pH 7.3
Duration of experiment: 8 h.
Application area: 1 cm$^2$ on the upper dorsum. The various doses applied on the test area are given in the following table.

|  | Group 1 | Group 2 | Group 3 | Group 4 | Group 5 |
|---|---|---|---|---|---|
| Applied volume [μL] | 1.0 | 5.0 | 7.0 | 15.0 | 30.0 |
| Appl. lipid amount [mg] | 0.10 | 0.50 | 0.75 | 1.50 | 3.00 |
| Applied activity [cpm] | 108998 | 544991 | 817486 | 1634972 | 3269943 |

Results of test measurements are given in FIGS. 1 to 6.

EXAMPLES 6-8

Longer Term Administration
Highly adaptable complex droplets (ultradeformable vesicles; Transfersomes)
87.4 mg phosphatidylcholine from soy bean (SPC)
12.6 mg sodium cholate (NaChol)
0.9 mL phosphate buffer, pH 7.3
trace amount of $^3$H-DPPC with specific activity: 250 μCi/mL
Duration of experiment: 24 h.

Application area: 1 cm squared; dose per area is given in the following table.

|  | Group 6 | Group 7 | Group 8 |
|---|---|---|---|
| Applied volume [μL] | 10.0 | 50.0 | 100.0 |
| Appl. lipid amount [mg] | 1.00 | 5.00 | 10.00 |
| Applied activity [cpm] | 145599 | 727997 | 1E+06 |

To test the effect of changing administered dose per area over longer period of time, even greater suspension volumes were applied on upper back of test mice.

Resulting data are analysed and presented together with those from previous experimental series in FIGS. 1 to 7.

FIG. 1 shows the recovery of relative activity (penetrant amount) in different layers of the skin as a function of applied activity (dose).

Figure 2:
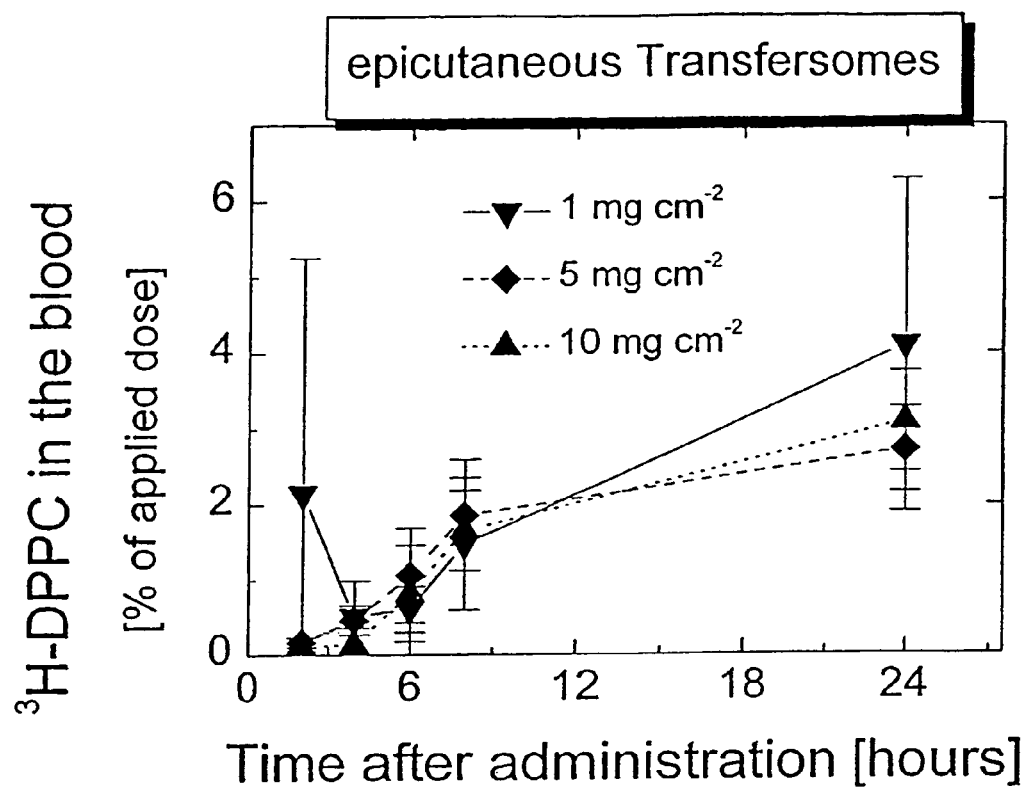
FIG. 2 shows the amount of carrier derived radioactivity ($^3$H-DPPC) in the blood as a function of time and epicutaneously administered penetrant quantity, expressed as percentage of applied dosage.

FIG. 2 shows the amount of carrier derived radioactivity ($^3$H-DPPC) in the blood as a function of time and epicutaneously administered penetrant quantity, expressed as percentage of applied dosage. As can be seen in this figure the relative amount of non-invasively administered lipid found in the blood reaches appreciable level after a clear lag-time of approximately 4 hours, but is nearly independent of the dose used.

Figure 3:
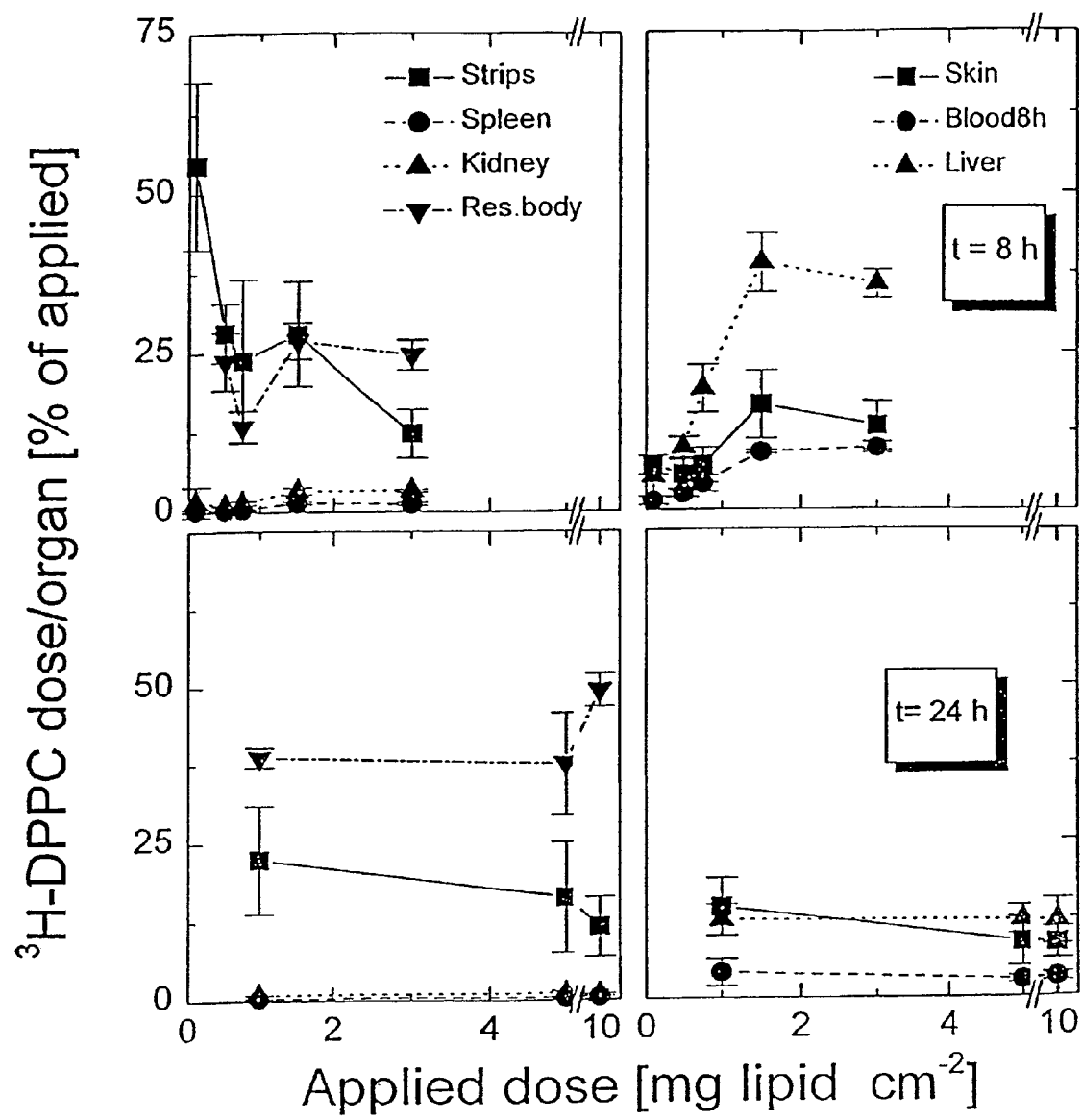
FIG. 3 indicates the relative accumulation of carrier derived radioactivity in various organs at two different time points after an increasing mass of ultradeformable carriers has been administered on the skin.

FIG. 3 indicates the relative accumulation of carrier derived radioactivity in various organs at two different time points after an increasing mass of ultradeformable carriers has been administered on the skin. It is apparent that whereas the relative amount of the carrier derived radioactivity decreases with the applied dosage at both times of exploration, the phospholipid-amount in the blood, viable skin and liver in parallel increases at t =8 h, but remains nearly unchanged at t=24 h.

Figure 4:
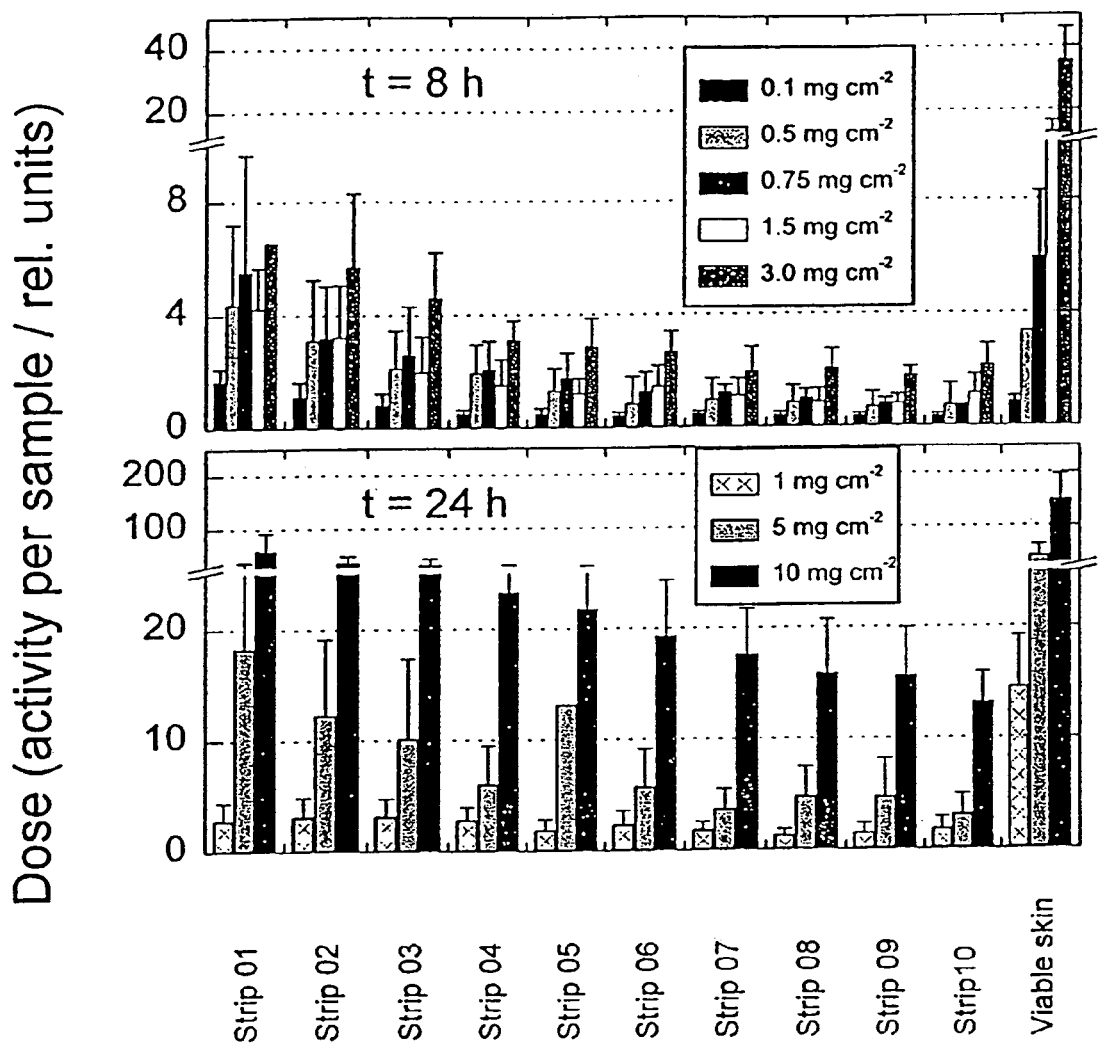
FIG. 4 shows the absolute penetrant distribution profile (in arbitrary units) in different layers of the skin as a function of applied activity (dose).

FIG. 4 shows the absolute penetrant distribution profile (in arbitrary units) in different layers of the skin as a function of applied activity (dose). Little dose dependence is seen in the horny layer for area doses between 0.5 mg cm$^{-2}$ and up to 1.5 mg cm$^{-2}$, but greater penetrant amounts are deposited much more efficiently in the barrier. This is true 8 hours as well as 24 hours after the suspension administration. Viable skin accumulates the penetrant derived material in a dose dependent fashion in entire investigated range.

Figure 5:
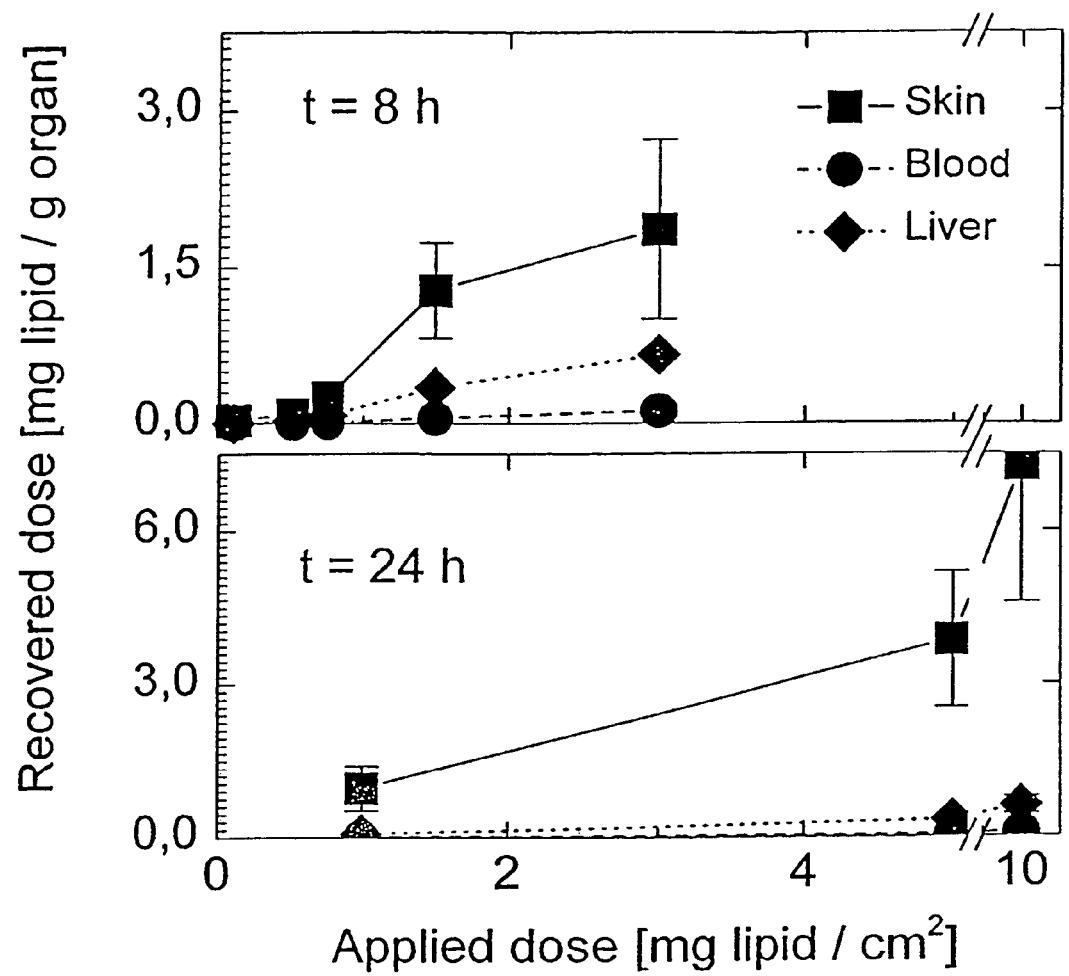
FIG. 5 shows the total amount of penetrant recovered in different tissues (skin, blood, liver) at different times after the administration of an increasing quantity of ultradeformable penetrants on the skin grows with the applied dose per area.

FIG. 5 shows the total amount of penetrant recovered in different tissues (skin, blood, liver) at different times after the administration of an increasing quantity of ultradeformable penetrants on the skin grows with the applied dose per area. However, while at t=8 h, an apparent saturation tendency is observed for doses greater than 1.5 mg cm$^{-2}$, at t=24 h the dose dependence is linear.

Figure 6:
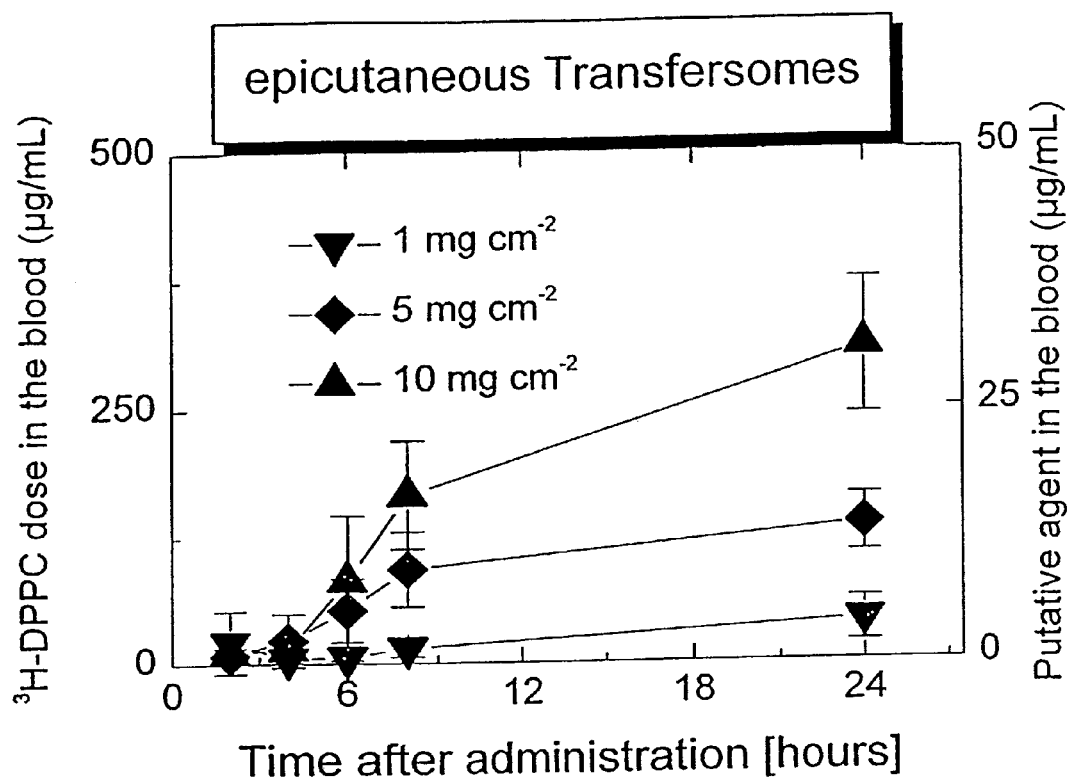
FIG. 6 shows the time dependence of penetrant derived radioactivity in the blood as a function of epicutaneously administered suspension volume (lipid amount).

FIG. 6 shows the time dependence of penetrant derived radioactivity in the blood as a function of epicutaneously administered suspension volume (lipid amount). As can be seen form this figure the temporal penetration characteristics are essentially independent of the applied dose: after a lag-time period of 4-6 hours, nearly steady state situation is observed.

Figure 7:
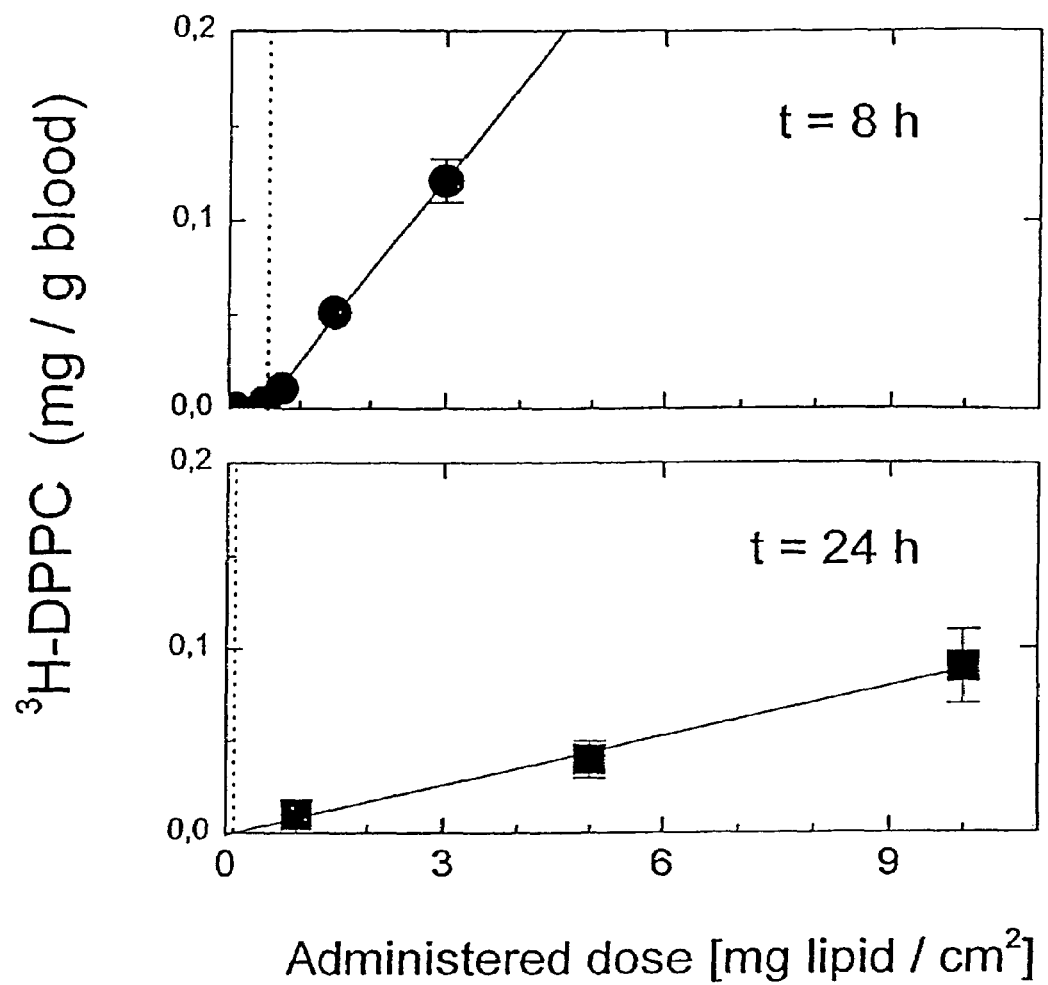
FIG. 7 shows the penetrant derived radioactivity in the blood as a function of epicutaneously administered dose measured 8 h or 24 h after the application.

FIG. 7 shows the penetrant derived radioactivity in the blood as a function of epicutaneously administered dose measured 8 h or 24 h after the application. Linear extrapolation suggests that barrier starts to adapt itself to penetrant transport at approximately 0.75 mg cm$^{-2}$.

Non-occlusive One-compartment and Multicompartment Patches

Figure 8:
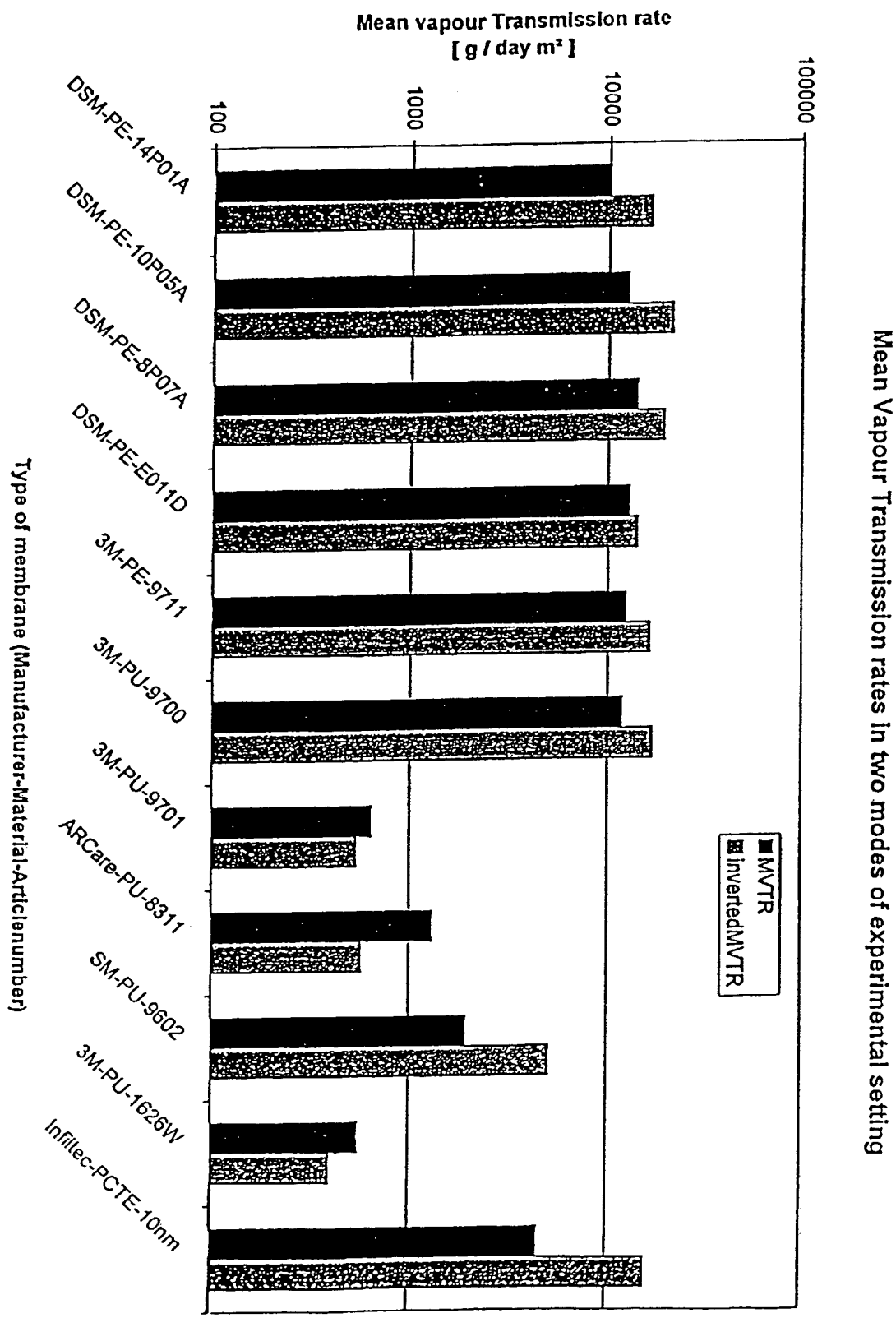
FIG. 8 shows the results obtained by measurement of the mean vapor transmission rate (MVTR) of five microporous polyethylene membranes, four polyurethane membranes and one polycarbonate track etched membrane.

FIG. 8 shows the results obtained by measurement of the mean vapour transmission rate (MVTR) of five microporous polyethylene membranes, four polyurethan membranes and one polycarbonate track etched membrane. Abbreviations used:

| First akronym: | |
|---|---|
| DSM | DSM Solutech, Heerlen, The Netherlands |
| 3M | 3M Medica, Borken, Germany |
| ARCare | Adhesives Research, Limerick, Ireland |
| SM | Smith and Nephew |
| Infiltec | Infiltec, Speyer, Germany |

| Second akronym: | |
|---|---|
| PE | microporous polyethylen |
| PU | polyurethan |
| PCTE | polycarbonate track etched |

The third akronym refers to the article number.

Figure 9:
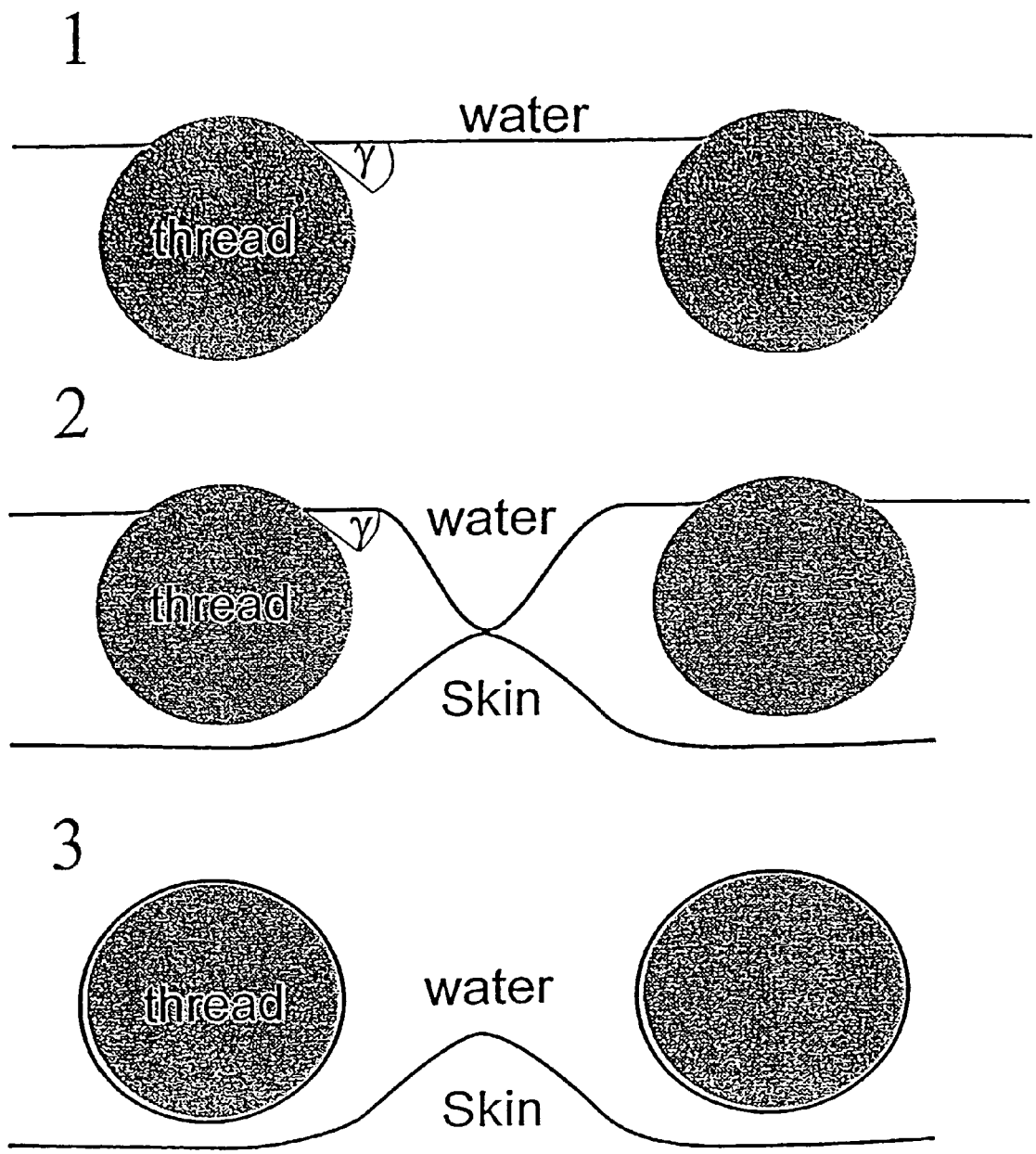
FIG. 9 is a diagram showing the principle of the "switching-effect," which e.g. is observed in connection with the inventive hydrophobic mesh-membranes.

FIG. 9 is a diagram showing the principle of the "switching-effect", which e.g. is observed in connection with the inventive hydrophobic mesh-membranes. A cross-section of two threads of a sieving material is given. In part 1 the threads are covered by a Transfersom®-formulation or lipid suspension without any contact to the skin, e.g. during storage. Contact with skin causes liquid bridges to the surface of the skin (part 2), which finally leads to complete skin wetting and release of Transfersomes® through the "sieve" (part 3).

Figure 10:
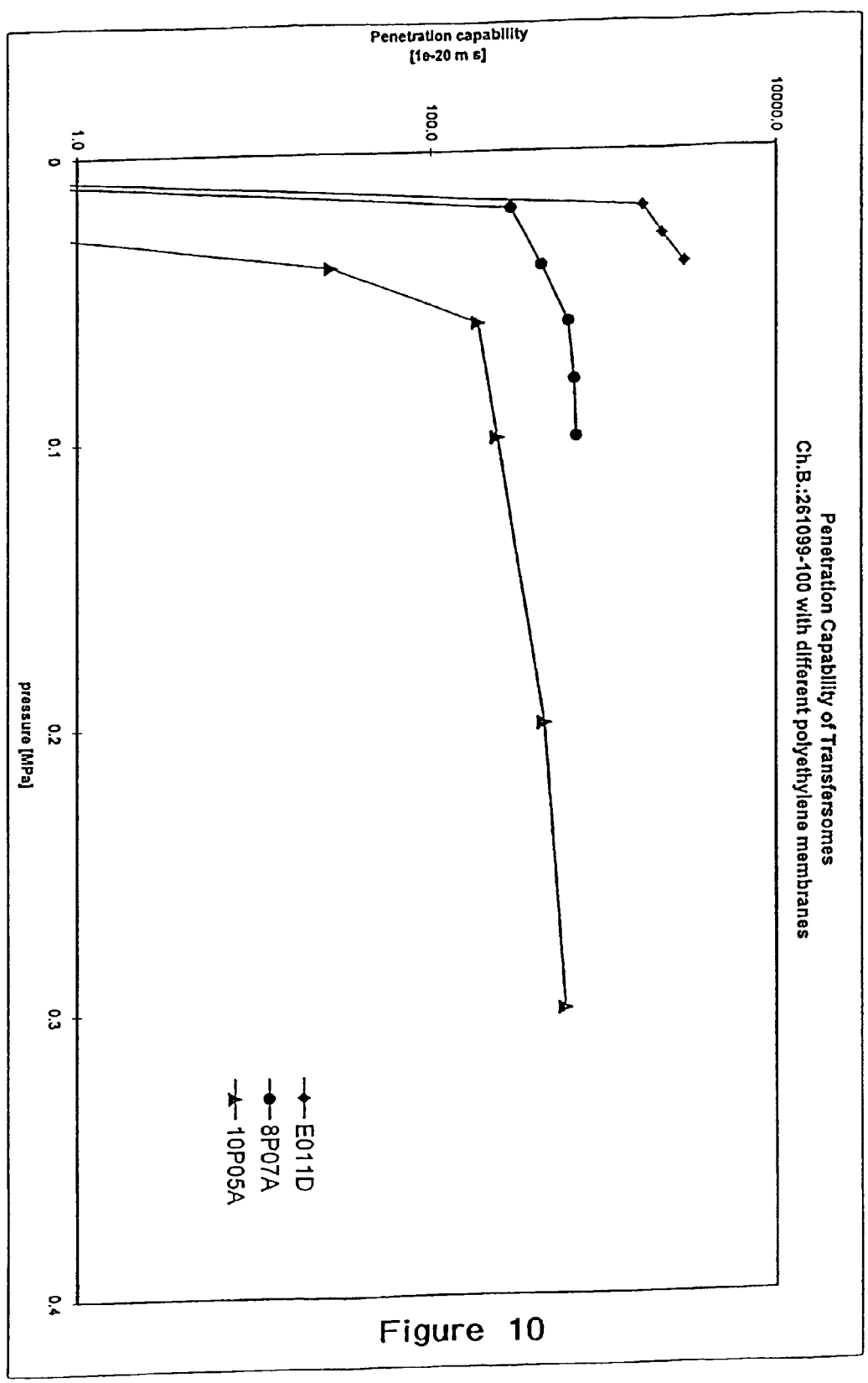
FIG. 10 shows the penetrability of three different microporous polyethylene membranes for Transfersomes namely Type-C; Solupor-E011 D, Solupor-8P07A and Solupor-10P05A (DSM Solutech, Heerlen, The Netherlands).

FIG. 10 shows the penetrability of three different microporous polyethylen membranes for Transfersomes®, namely Type-C; Solupor-E011 D, Solupor-8P07A and Solupor-10P05A (DSM Solutech, Heerlen, The Netherlands). They exhibit a high penetrability at small pressures thus allowing for Transfersomes to wet the skin upon contact. Moreover, it can be taken from the figure, that no penetration of the Transfersomes® through the membranes is observed, when the pressure is 0.

Figure 11:
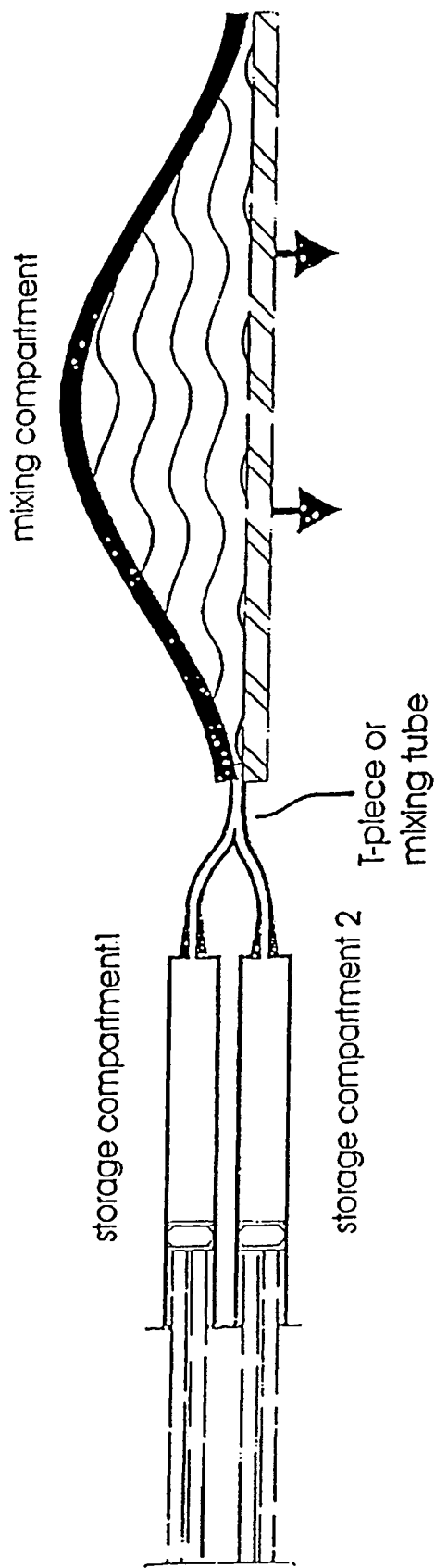
FIG. 11 shows a schematic diagram of a multicompartment patch having external compartments according to the present invention in form of twin syringe serving as storage compartments with mixing tubing or T-piece connector attached to the patch.

FIG. 11 shows a schematic diagram of a multicompartment patch having external compartments according to the present invention in form of twin syringe serving as storage compartments with mixing tubing or T-piece connector attached to the patch.

Figure 12:
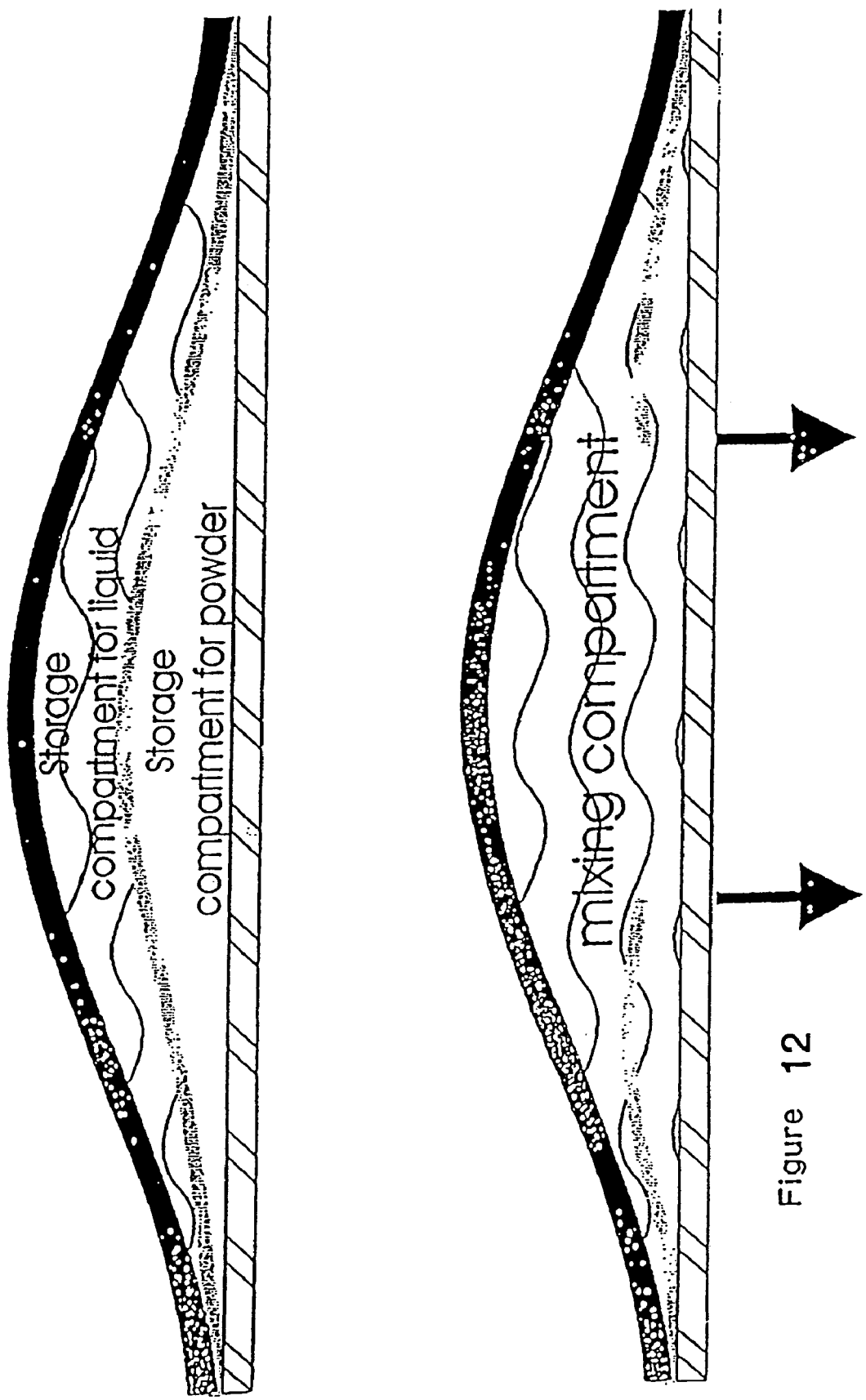
FIG. 12 shows a schematic diagram of a multicompartment patch according to the present invention having vertically stacked compartments.

FIG. 12 shows a schematic diagram of a multicompartment patch according to the present invention having vertically stacked compartments.

Figure 13:
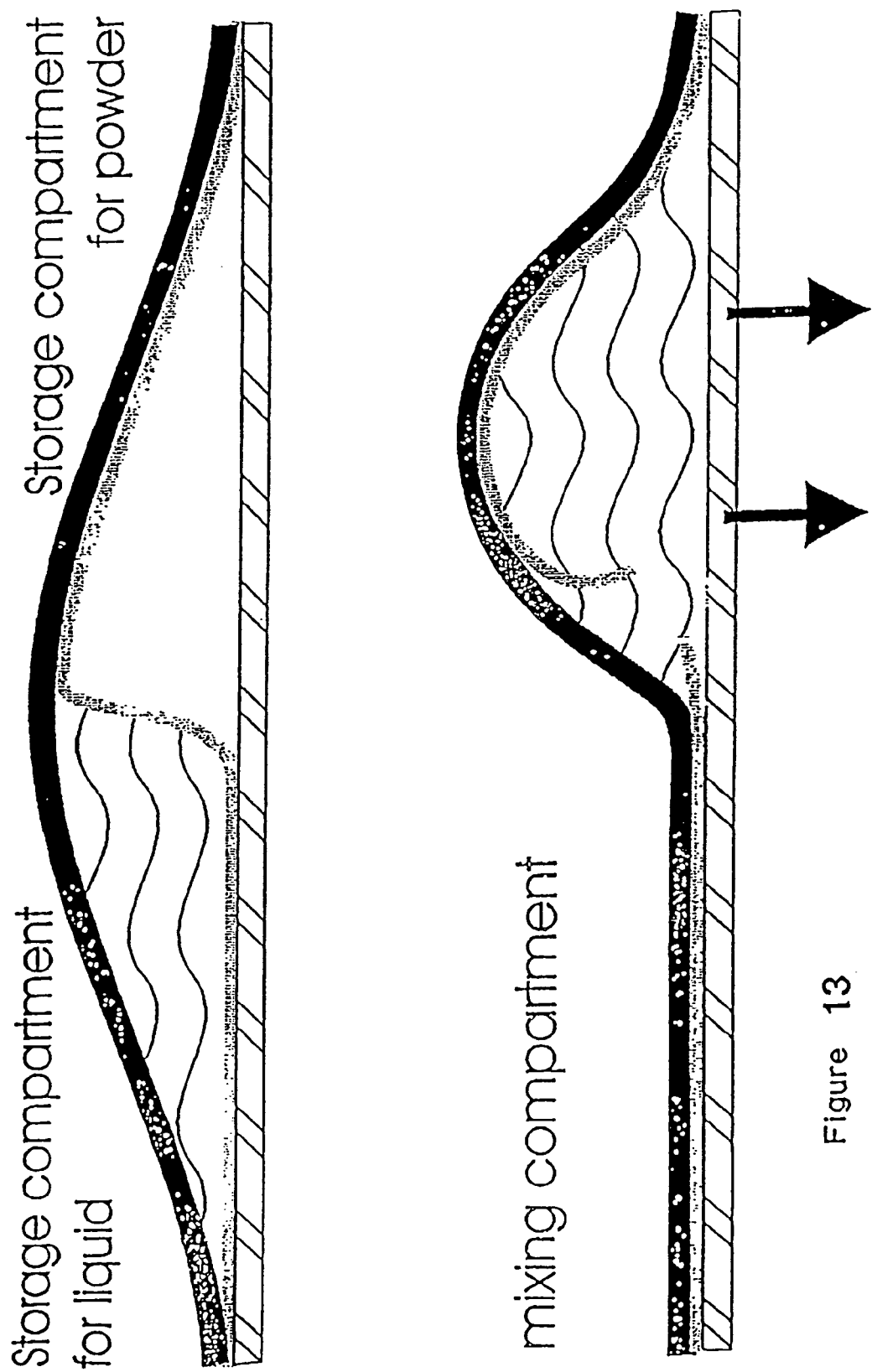
FIG. 13 shows a schematic diagram of a multicompartment patch according to the present invention with a side-by-side alignment of compartments with vertically introduced septum.

FIG. 13 shows a schematic diagram of a multicompartment patch according to the present invention with a side-by-side alignment of compartments with vertically introduced septum.

Figure 14:
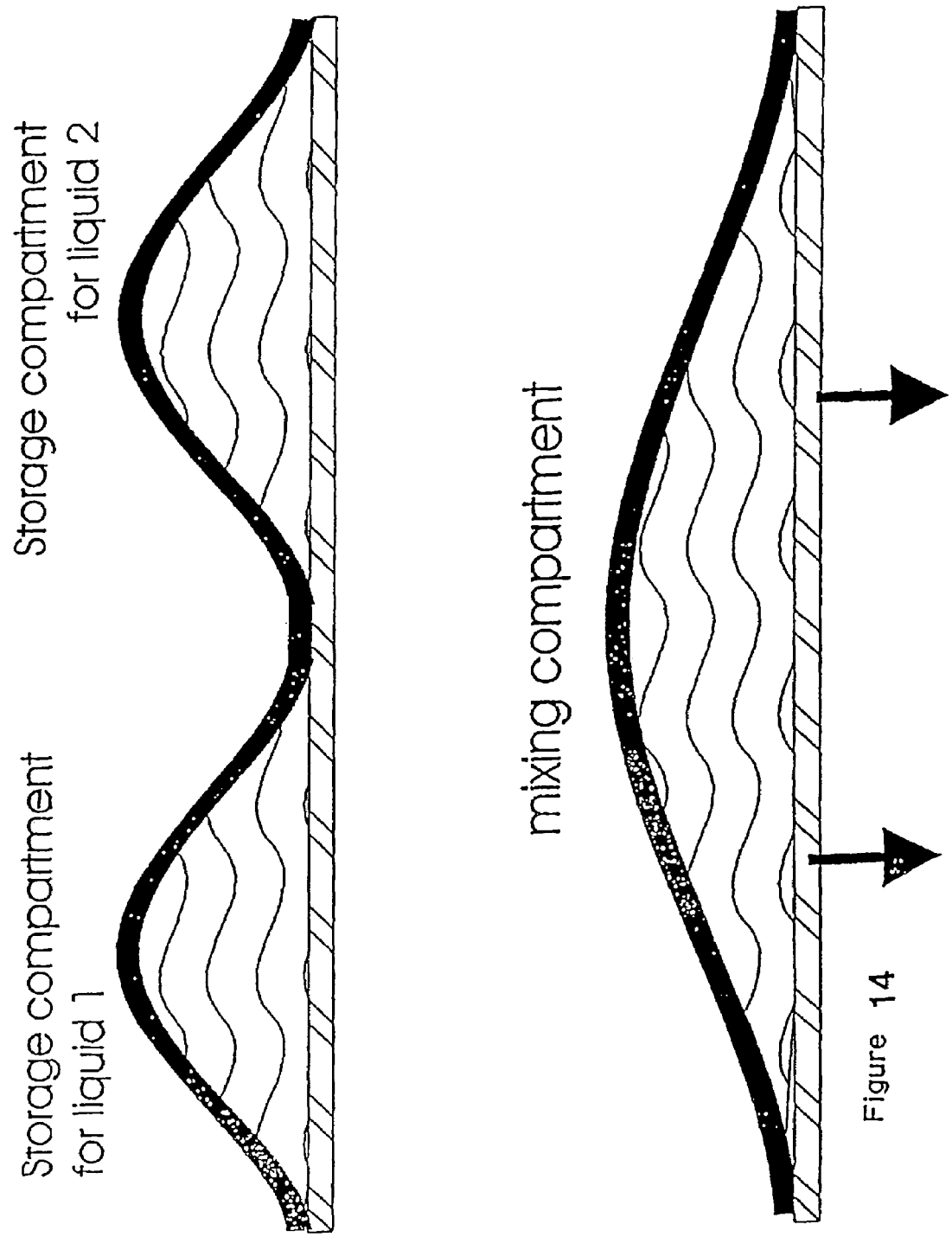
FIG. 14 shows a schematic diagram of a multicompartment patch according to the present invention having a side-by-side alignment of compartments with separating lamination.

FIG. 14 shows a schematic diagram of a multicompartment patch according to the present invention having a side-by-side alignment of compartments with separating lamination.

An example for a patch, which is suited for application of a Transfersome®-formulation (V=0.6 mL) according to the present invention is given below. Said transdermal patch can be used as an one-compartment patch according to the present invention and also can be fitted with external compartments thereby producing a multicompartment patch according to the present invention.

| Type | Material | Dimension |
|---|---|---|
| Backing liner | COTRAN 9701/3M 2 mil Polyurethan 70-0000-3993-6 SLP P261450106 | Inner diameter 3.6 cm outer rectangle 4.5 cm * 4.5 cm |
| Compartment | 3M Foam tape 1779 polyolefin tape double layered # 70-0000-6467-8 | |
| Inner liner | PCTE 100 nm Poretics; Cat 19410 LOT AE84AG11C024 | |
| protective periphery | Leukoplast | |
| Injection tubing | Obturator Venflon 1.2 mm/18G L45 mm Art. No. 4253-1 LOT 931208 | Preinstalled tubing; removed after TFS injection; port sealed with Leukoplast |
| Area of application | | 10 cm$^2$ |
| Application perimeter | | 3.6 cm |
| Concentric seal width | | >0.8 cm |
| Total area | | 20.25 cm$^2$ |

Another example for a patch, which is suited for application of a Transfersome®-formulation according to the present invention is given below. Said patch has no inner liner membrane and is intended for direct application to the skin. Filling of the mixing compartment (formed by the backing liner and the skin) can be done e.g. by external syringes connected to the mixing compartment.

| Type | Material | Dimension |
|---|---|---|
| Backing liner | microporous Polyethylene 9711; 3M Medica #KG-90054 | 6 cm * 8.6 cm rectangle |
| Compartment | 3M Foam tape 1779 polyolefin tape double layered # 70-0000-6467-8 | outer rectangle 6 cm * 8.6 cm inner perimeter 4.4 cm * 7 cm |
| release cover I protective periphery | from foam tape Leukoplast | |
| Injection tubing | Obturator Venflon 1.2 mm/18G L45 mm Art. No. 4253-1 LOT 931208 | Preinstalled tubing; removed after TFS injection; port sealed with Leukoplast |
| Area of application | | 25 cm$^2$ |
| Application perimeter | | 4.4 cm * 7 cm |
| Concentric seal width | | >0.8 cm |
| Total area | | 51.6 cm$^2$ |

The invention claimed is:

1. A method for controlling the flux of penetrants across an adaptable semi-permeable porous barrier, the method comprising the steps of:

preparing a formulation by suspending or dispersing said penetrants in a polar liquid, the penetrants comprising at least two kinds or forms of amphiphilic substances with a tendency to aggregate, wherein said at least two substances differ by at least a factor of 10 in solubility in said polar liquid, and wherein said penetrants are able to transport a drug agent through the pores of said barrier or enable drug agent permeation through the pores of said barrier after the penetrants have entered the pores, the formulation further comprising a thickening agent and having a viscosity that is 0.2 kN s/m² to 5 kN s/m²;

selecting a dose amount of said penetrants to be applied on a predetermined area of said barrier to control the flux of said penetrants across said barrier; and applying said formulation containing the selected dose amount of said penetrants onto said area of said porous barrier, the formulation having a viscosity that enables retention of the drug agent at the area, and wherein the drug agent is a peptide or a protein.

2. The method of claim 1, wherein said substances when in the form of homo-aggregates, for the more soluble substance, or of hetero-aggregates, for any combination of both said substances, have a preferred average diameter smaller than the diameter of homo-aggregates containing merely the less soluble substance.

3. The method of claim 1, wherein the more soluble substance tends to solubilise the penetrants and the content of such substance is to up to 99 mol-% of solubilising concentration or else corresponds to up to 99 mol-% of the saturating concentration in an unsolubilised droplet.

4. The method of claim 1, wherein the presence of the more soluble substance lowers the average elastic energy of the penetrants to a value at least 5 times lower than the average elastic energy of red blood cells or of phospholipid bilayers with fluid aliphatic chains.

5. The method of claim 1, wherein the presence of the more soluble substance lowers the average elastic energy of the penetrants to a value at least 10 times lower than the average elastic energy of red blood cells or of phospholipid bilayers with fluid aliphatic chains.

6. The method of claim 1, wherein the presence of the more soluble substance lowers the average elastic energy of the penetrants to a value of more than 10 times lower than the average elastic energy of red blood cells or of phospholipid bilayers with fluid aliphatic chains.

7. The method of claim 1 wherein the flux across said barrier is increased by enlarging the applied dose per area of said penetrants.

8. The method of claim 1, wherein the pH of the formulation is between 3 and 10.

9. The method of claim 1, wherein the pH of the formulation is between 4 and 9.

10. The method of claim 1, wherein the pH of the formulation is between 5 and 8.

11. The method of claim 1, wherein the formulation viscosity is up to 1 kN s/$m^2$.

12. The method of claim 1, wherein the average diameter of the penetrants is between about 30 nm and 500 nm.

13. The method of claim 1, wherein the average diameter of the penetrants is between about 40 nm and 250 nm.

14. The method of claim 1, wherein the average diameter of the penetrants is between about 50 nm and 200 nm.

15. The method of claim 1, wherein the average diameter of the penetrants is between about 60 nm and 150 nm.

16. The method of claim 1, wherein the total dry weight of the penetrants in a formulation is about 0.01 w-% to 40 w-% of total formulation mass.

17. The method of claim 1, wherein the total dry weight of the penetrants in a formulation is about 0.1 w-% and 30 w-% of total formulation mass.

18. The method of claim 1, wherein the total dry weight of the penetrants in a formulation is about 0.5 w-% and 20 w-% of total formulation mass.

19. The method of claim 1, wherein the penetrants are formed by action of mechanical energy.

20. The method of claim 19, wherein said amphiphilic substances are dissolved in a volatile solvent, or in a pharmaceutically acceptable organic solvent, prior to penetrant formation, and the volatile solvent or the pharmaceutically acceptable organic solvent is then subsequently removed.

21. The method of claim 20, wherein the pharmaceutically acceptable organic solvent is selected from supercritical $CO_2$, and an alcohol.

22. The method of claim 20, wherein the volatile solvent is ethanol or supercritical $CO_2$, and wherein the volatile solvent is removed by evaporation or dilution.

23. The method of claim 20, wherein the pharmaceutically acceptable organic solvent is ethanol, 1- or 2-propanol, benzyl alcohol, propylene glycol, polyethylene glycol or glycerol.

24. The method of claim 20, wherein the volatile solvent is removed by evaporation or dilution.

25. The method of claim 19, wherein the mechanical energy is shaking, stirring, vibrating, homogenization, ultrasonication, freezing and thawing, or filtration using convenient driving pressure.

26. The method of claim 1, wherein the penetrants are formed under the influence of mechanical stress selected from shaking, stirring, high velocity stirring, vibrating, homogenizing, ultrasonication, shearing, freezing and thawing.

27. The method of claim 1, wherein the formation of said penetrants is induced by filtration using a filtering material having pores sizes between about 0.01 μm and 0.8 μm.

28. The method of claim 27, wherein the filtering material has pore sizes between about 0.02 μm and 0.3 μm.

29. The method of claim 27, wherein the filtering material has pore sizes between about 0.05 μm and 0.15 μm.

30. The method of claim 27, wherein several filters are used sequentially or in parallel.

31. The method of claim 1, wherein said drug agent and penetrants are made to associate, at least partly, after the formation of said penetrants, or simultaneously with penetrant formation.

32. The method of claim 31, wherein the drug agent and penetrants are made to associate simultaneously with penetrant formation using a drug co-solution and penetrant ingredients.

33. The method of claim 31, wherein said penetrants, with which the drug agent is associated, are prepared immediately before the application of the formulation from a suitable concentrate or a lyophylisate.

34. The method of claim 1, wherein the formulation is applied by spraying, smearing, rolling or sponging on the application area.

35. The method of claim 34, wherein the formulation is applied by using a metering sprayer, spender, roller, sponge or a non-occlusive patch.

36. The method of claim 1, wherein the barrier is a part of a mammalian body or a plant.

37. The method of claim 36, wherein the barrier is skin, at least partly keratinised endothelium, nasal or any other mucosa.

38. The method of claim 37, wherein the formulation is applied on said skin or said at least partly keratinised endothelium and the area dose of said penetrant is between about 0.1 mg/$cm^2$ and 40 mg/$cm^2$.

39. The method of claim 38, wherein the area dose of said penetrant is between about 0.25 mg/$cm^2$ and 30 mg/$cm^2$.

40. The method of claim 38, wherein the area dose of said penetrant is between about 0.5 mg/$cm^2$ and 15 mg/$cm^2$.

41. The method of claim 37, wherein the formulation is applied on said nasal or other mucosa and the area dose of said penetrant is between about 0.05 mg/cm$^2$ and 20 mg/cm$^2$.

42. The method of claim 41, wherein the area dose of said penetrant is between about 0.1 mg/cm$^2$ and 15 mg/cm$^2$.

43. The method of claim 41, wherein the area dose of said penetrant is between about 0.5 mg/cm$^2$ and 10 mg/cm$^2$.

44. The method of claim 36, wherein the formulation is applied on plant body, plant leaves or plant needles and the area dose of said penetrant is between about 0.0001 mg/cm$^2$ and 0.1 mg/cm$^2$.

45. The method of claim 44, wherein the area dose of said penetrant is between about 0.0005 mg/cm$^2$ and 0.05 mg/cm$^2$.

46. The method of claim 44, wherein the area dose of said penetrant is between about 0.001 mg/cm and 0.01 mg/cm.

47. The method of claim 1, wherein the formulation further comprises at least one antioxidant.

48. The method of claim 47, wherein the at least one antioxidant is present in the formulation in an amount that reduces the increase of oxidation index to less than 100% per 6 months.

49. The method of claim 47, wherein the at least one antioxidant is in an amount that reduces the increase of oxidation index to less than 100% per 12 months.

50. The method of claim 47, wherein the at least one antioxidant is in an amount that reduces the increase of oxidation index to less than 50% per 12 months.

51. The method of claim 1, wherein the formulation further comprises at least one microbicide.

52. The method of claim 51, wherein the at least one microbicide is present in an amount that reduces the bacterial count of 1 million germs added per g of total mass of the formulation to less than 100 in the case of aerobic bacteria, to less than 10 in the case of entero-bacteria, and to less than 1 in the case of Pseudomonas aeruginosa or Staphilococcus aureus, after a period of 4 days.

53. The method of claim 1, wherein the formation of penetrants is induced by evaporation from a reverse phase, by injection or dialysis, or filtration using low to intermediate driving pressure.

54. The method of claim 1, wherein the peptide or protein is insulin or serum albumin.

55. A method for controlling the flux of penetrants across an adaptable semi-permeable porous barrier, the method comprising the steps of:

preparing a formulation by suspending or dispersing said penetrants in a polar liquid, the penetrants comprising at least two kinds or forms of amphiphilic substances with a tendency to aggregate, wherein said at least two substances differ by at least a factor of 10 in solubility in said polar liquid, and wherein said penetrants are able to transport a drug agent through the pores of said barrier or enable drug agent permeation through the pores of said barrier after the penetrants have entered the pores, the formulation further comprising a thickening agent and at least one antioxidant;

selecting a dose amount of said penetrants to be applied on a predetermined area of said barrier to control the flux of said penetrants across said barrier; and applying said formulation containing a selected dose amount of said penetrants onto said area of said porous barrier, the formulation having a viscosity that enables retention of the drug agent at the area, wherein the at least one antioxidant reduces an increase of oxidation index to less than 100% per 12 months, and wherein the drug agent is a peptide or a protein.

56. The method of claim 55, wherein the peptide or protein is insulin or serum albumin.

57. A method for controlling the flux of penetrants across an adaptable semi-permeable porous barrier, the method comprising the steps of:

preparing a formulation by suspending or dispersing said penetrants in a polar liquid, the penetrants comprising at least two kinds or forms of amphiphilic substances with a tendency to aggregate, wherein said at least two substances differ by at least a factor of 10 in solubility in said polar liquid, and wherein said penetrants are able to transport a drug agent through the pores of said barrier or enable drug agent permeation through the pores of said barrier after the penetrants have entered the pores, the formulation further comprising a thickening agent and at least one antioxidant;

selecting a dose amount of said penetrants to be applied on a predetermined area of said barrier to control the flux of said penetrants across said barrier; and applying said formulation containing the selected dose amount of said penetrants onto said area of said porous barrier, the formulation having a viscosity that enables retention of the drug agent at the area, wherein the at least one antioxidant reduces the increase of oxidation index to less than 50% per 12 months and wherein the drug agent is a peptide or a protein.

58. The method of claim 57, wherein the peptide or protein is insulin or serum albumin.

59. A method for controlling the flux of penetrants across an adaptable semi-permeable porous barrier, the method comprising the steps of:

preparing a formulation by suspending or dispersing said penetrants in a polar liquid, the penetrants comprising at least two kinds or forms of amphiphilic substances with a tendency to aggregate, wherein said at least two substances differ by at least a factor of 10 in solubility in said polar liquid, and wherein said penetrants are able to transport a drug agent through the pores of said barrier or enable drug agent permeation through the pores of said barrier after the penetrants have entered the pores, the formulation further comprising a thickening agent and at least one microbicide;

selecting a dose amount of said penetrants to be applied on a predetermined area of said barrier to control the flux of said penetrants across said barrier; and applying said formulation containing the selected dose amount of said penetrants onto said area of said porous barrier, the formulation having a viscosity that enables retention of the drug agent at the area, wherein said at least one microbicide is added in an amount that reduces the bacterial count of 1 million germs added per g of total mass of the formulation to less than 100 in the case of aerobic bacteria, to less than 10 in the case of enterobacteria, and to less than 1 in the case of Pseudomonas aeruginosa or Staphylococcus aureus, after a period of 3 days and wherein the drug agent is a peptide or a protein.

60. The method of claim 59, wherein said at least one microbicide is added in an amount that reduces said bacterial count after a period of 1 day.

61. The method of claim 59, wherein the peptide or protein is insulin or serum albumin.

62. A method for controlling the flux of penetrants across an adaptable semi-permeable porous barrier, the method comprising the steps of:

preparing a formulation by suspending or dispersing said penetrants in a polar liquid, the penetrants comprising at least two kinds or forms of amphiphilic substances with a tendency to aggregate, wherein said at least two substances differ by at least a factor of 10 in solubility in said polar liquid, and wherein said penetrants are able to transport a drug agent through the pores of said barrier or enable drug agent permeation through the pores of said barrier after the penetrants have entered the pores, the formulation further comprising a thickening agent;

selecting a dose amount of said penetrants to be applied on a predetermined area of said barrier to control the flux of said penetrants across said barrier; and applying said formulation containing the selected dose amount of said penetrants onto said area of said porous barrier, the formulation having a viscosity that enables retention of the drug agent at the area, wherein said thickening agent is selected from the class of pharmaceutically acceptable hydrophilic polymers consisting of partially etherified cellulose derivatives; completely synthetic hydrophilic polymers; natural gums comprising alginates, carrageenans, guar-gums, gelatines, tragacanths, amidated pectins, xanthans, chitosan, collagens, agaroses; mixtures and further derivatives or co-polymers thereof, and wherein the drug agent is a peptide or a protein.

63. The method of claim 62, wherein the concentration of said pharmaceutically acceptable hydrophilic polymer is in the range between 0.01 w-% and 10 w-%.

64. The method of claim 62, wherein the partially etherified cellulose derivatives are selected from carboxymethyl-, hydroxyethyl-, hydroxypropyl-, hydroxypropylmethyl- and methyl-celluloses; and wherein the completely synthetic hydrophilic polymers are selected from polyacrylates, polymethacrylates, poly(hydroxyethyl)-, poly(hydroxypropyl)-, poly(hydroxypropylmethyl)methacrylates, polyacrylonitriles, methallyl-sulphonates, polyethylenes, polyoxiethylenes, polyethylene glycols, polyethylene glycol-lactides, polyethylene glycol-diacrylates, polyvinylpyrrolidones, polyvinyl alcohols, poly(propylmethacrylamides), poly(propylene fumarate-co-ethylene glycols), poloxamers, polyaspartamides, hydrazine cross-linked hyaluronic acids, and silicones.

65. The method of claim 62 wherein the peptide or protein is insulin or serum albumin.

66. A method for controlling the flux of penetrants across an adaptable semi-permeable porous barrier, the method comprising the steps of:

preparing a formulation by suspending or dispersing said penetrants in a polar liquid, the penetrants comprising at least two kinds or forms of amphiphilic substances with a tendency to aggregate, wherein said at least two substances differ by at least a factor of 10 in solubility in said polar liquid, and wherein said penetrants are able to transport a drug agent through the pores of said barrier or enable drug agent permeation through the pores of said barrier after the penetrants have entered the pores, the formulation further comprising a thickening agent and at least one antioxidant:

selecting a dose amount of said penetrants to be applied on a predetermined area of said barrier to control the flux of said penetrants across said barrier; and applying said formulation containing the selected dose amount of said penetrants onto said area of said porous barrier, the formulation having a viscosity that enables retention of the drug agent at the area, wherein said at least one antioxidant is selected from synthetic phenolic antioxidants; aromatic amines; phenols and phenolic acids, protocatechuic acid, quinic acid, syringic acid, ellagic acid, salicylic acid, nordihydroguaiaretic acid (NDGA), eugenol; tocopherols and their derivatives; trolox and corresponding amide- and thiocarboxamide analogues; ascorbic acid esters, ascorbic acid and its salts, isoascorbate, (2 or 3 or 6)-o-alkylascorbic acids, ascorbyl esters; non-steroidal anti-inflammatory agents (NSAIDs); sodium bisulphate, sodium metabisulphite, thiourea; chelating agents; glucose, ubiquinol-10; enzymatic antioxidants; flavonoids; cystein, N-acetylcystein, mesna, glutathione, thiohistidine derivatives, triazoles; monothioglycerol, NDGA, tannins, cinnamic acid, hydroxycinnamatic acids and their esters; spice extracts; citric acid; camosic acid, camosol, carsolic acid; rosmarinic acid, rosmarindiphenol, gentisic acid, ferulic acid; oat flour extracts; thioethers, dithioethers, sulphoxides, tetralkyithiuram disulphides; phytic acid, steroid derivatives; tryptophan metabolites; organochalcogenides; and oxidation suppressing enzymes, and wherein the drug agent is a peptide or a protein.

67. The method of claim 66, wherein the at least one antioxidant is selected from tocopherols in a concentration of between 0.005 and 5 w-%, ascorbic acid esters in a concentration of between 0.001 and 5 w-%, ascorbic acid and its salts in a concentration of between 0.001 and 5 w-%, sodium bisuiphite or sodium metabisulphite in a concentration of between 0.001 and 5 w-%, thiourea in a concentration of between 0.0001 and 2 w-%, cystein in a concentration of between 0.01 and 5 w-%, monothioglycerol in a concentration of between 0.01 to and 5 w-%, NDGA in a concentration of between 0.0005-2 w-%, glutathione in a concentration of between 0.005 and 5 w-%, and citric acid in a concentration of between 0.001 and 5 w-%.

68. The method of claim 66, wherein the at least one antioxidant is selected from tocopherols in a concentration of between 0.01 and 0.5 w-%, ascorbic acid esters in a concentration of between 0.005 and 0.5 w-%, ascorbic acid and its salts in a concentration of between 0.005 and 0.5 w-%, sodium bisulphite or sodium metabisulphite in a concentration of between 0.005 and 0.5 w-%, thiourea in a concentration of between 0.0005 and 0.2 w-%, cystein in a concentration of between 0.05 and 2 w-%, glutathione in a concentration of between 0.01 and 0.5 w-%, and citric acid in a concentration of between 0.005 and 3 w-%.

69. The method of claim 66, wherein the at least one antioxidant is selected from tocopherols in a concentration of between 0.05 and 0.075 w-%, ascorbic acid esters in a concentration of between 0.01 and 0.15 w-%, ascorbic acid and its salts in a concentration of 0.01 and 0.1 w-%, sodium bisulphite or sodium metabisulphite in a concentration of between 0.01 -0.15 w-%, thiourea in a concentration of between 0.001-0.01 w-%, cystein in a concentration of between 0.1 to 1.0 w-%, monothioglycerol in a concentration of between 0.1-1.0 w-%, NDGA in a concentration of between 0.005-0.02 w-%, glutathione in a concentration of between 0.05 and 0.2 w-%, and citric acid in a concentration of between 0.01-0.2 w-%.

70. The method of claim 66, wherein the at least one antioxidant is selected from thiourea in a concentration of 0.005 w-%, cystein in a concentration of 0.5 w-%, monothioglycerol in a concentration of 0.5 w-%, NDGA in a concentration of 0.01 w-%, glutathione in a concentration of 0.1 w-%, and citric acid in a concentration of between 0.3 and 2 w-%.

71. The method of claim 66, wherein the synthetic phenolic antioxidants are selected from butylated hydroxyanisol (BHA), butylated hydroxytoluene (BHT), di-tert-butylphenol, tertiary butylhydroquinone (TBHQ), propyl gallate (PG), and 1-O-hexyl-2,3,5-trimethylhydroquinone (HTHQ); wherein the aromatic amines are selected from diphenylamine, p-alkylthio-o-anisidine, ethylenediamine derivatives, carbazol, and tetrahydroindenoindol; wherein the phenols and phenolic acids are selected from guaiacol, hydroquinone, vanillin, gallic acids and their esters, protocatechuic acid, quinic acid, syringic acid, ellagic acid, salicylic acid, nordihydroguaiaretic acid (NDGA), and eugenol; wherein the tocopherols are selected from alpha, beta, gamma, and delta tocopherols and their derivatives; wherein the ascorbyl esters are selected from 6-o-lauroyl, myristoyl, palmitoyl-, oleoyl, and linoleoyl-L-ascorbic acid; wherein the NSAIDs are selected from indomethacin, diclofenac, mefenamic acid, flufenamic acid, phenylbutazone, oxyphenbutazone acetylsalicylic acid, naproxen, diflunisal, ibuprofen, ketoprofen, piroxicam, penicillamine, penicillamine disulphide, primaquine, quinacrine, chloroquine, hydroxychloroquine, azathioprine, phenobarbital, and acetaminophen; wherein the chelating agents are selected from EDTA, GDTA and desferral; wherein the enzymatic antioxidants are selected from superoxide dismutase and metal complexes with a similar activity; wherein the flavonoids are selected from flavones, flavonols, flavonones, flavanoals, chacones, and anthocyanins; wherein the hydroxycinnamatic acids and their esters are selected from coumaric acids and their esters, caffeic acid and their esters, ferulic acid, (iso-) chlorogenic acid, and sinapic acid; wherein the spice extracts are selected from extracts of clove, cinnamon, sage, rosemary, mace, oregano, allspice, and nutmeg; wherein the oat flour extracts are selected from avenanthramide 1 and 2; and wherein the tryptophan metabolites are selected from 3-hydroxykynurenine and 3-hydroxyanthranilic acid.

72. The method of claim 71, wherein the antioxidant is selected from BHA or BHT in a concentration of 0.001 to 2 w-%, TBHQ and PG in a concentration of 0.001 to 2 w-%, and EDTA in a concentration of 0.001 to 5 w-%.

73. The method of claim 71, wherein the antioxidant is selected from BHA or BHT in a concentration of 0.0025 to 0.2 w-%, TBHQ and PG in a concentration of 0.005 to 0.2 w-%, and EDTA in a concentration of 0.005 to 0.5 w-%.

74. The method of claim 71, wherein the antioxidant is selected from BHA or BHT in a concentration of 0.005 to 0.02 w-%, TBHQ and PG in a concentration of 0.01 to 0.02 w-%, and EDTA in a concentration of 0.01 to 0.2 w-%.

75. The method of claim 71, wherein the antioxidant is EDTA in a concentration of 0.05 to 0.975 w-%.

76. The method of claim 66, wherein the tocopherols are selected from tocopheryl-acylates, tocopheryl-acetates, tocopheryl-laurates, tocopheryl-myristates, tocopheryl-palmitates, tocopheryl-oleates, tocopheryl-linoleates, tocopheryl-lipoates, and tocopheryl-POE-succinate; and wherein the enzymatic antioxidants are selected from catalase, glutathione peroxidase, beta-carotene, bilirubin, and uric acid.

77. The method of claim 66, wherein the peptide or protein is insulin or serum albumin.

78. A method for controlling the flux of penetrants across an adaptable semi-permeable porous barrier, the method comprising the steps of:
preparing a formulation by suspending or dispersing said penetrants in a polar liquid, the penetrants comprising at least two kinds or forms of amphiphilic substances with a tendency to aggregate, wherein said at least two substances differ by at least a factor of 10 in solubility in said polar liquid, and wherein said penetrants are able to transport a drug agent through the pores of said barrier or enable drug agent permeation through the pores of said barrier after the penetrants have entered the pores, the formulation further comprising a thickening agent and at least one microbicide;
selecting a dose amount of said penetrants to be applied on a predetermined area of said barrier to control the flux of said penetrants across said barrier; and
applying said formulation containing the selected dose amount of said penetrants onto said area of said porous barrier, the formulation having a viscosity that enables retention of the drug agent at the area, wherein said at least one microbicide is selected from short chain alcohols, hexachlorophene; phenolic compounds; triclosan, parabens; acids; quaternary ammonium compounds; phenoalkecinium salt; mercurium compounds; chlorhexidine or its gluconate; antibiotically active compounds of biological origin, and mixtures thereof, and wherein the drug agent is a peptide or a protein.

79. The method of claim 78, wherein the at least one microbicide is ethyl, propyl, butyl or benzyl alcohol in a concentration of up to 5 w-%.

80. The method of claim 78, wherein the parabens are selected from methyl-, ethyl-, propyl-, butyl-, and benzyl-paraben.

81. The method of claim 80, wherein the at least one microbicide is propyl paraben in a concentration range between 0.002-0.02 w-%.

82. The method of claim 78, wherein the microbicide is selected from parabens in a concentration of 0.05-0.2 w-% and chlorhexidine in a concentration of 0.01-0.05 w-%.

83. The method of claim 78, wherein the short chain alcohols are selected from ethyl, butyl, propyl, and isopropyl alcohol, chlorbutanol, benzyl alcohol, chlorbenzyl alcohol, and dichlorbenzylalcohol; the phenolic compounds are selected from cresol, 4-chloro-m-cresol, p-chloro-m-xylenol, dichlorophene, hexachlorophene, and povidon-iodine; the parabens are selected from alkyl-parabens; the acids are selected from sorbic acid, benzoic acid and its salts; the quaternary ammonium compounds are selected from alkonium salts and cetrimonium salts; the phenoalkecinium salt is selected from phenododecinium bromide and cetylpyridinium chloride; and the mercurium compounds are selected from phenylmercuric acetate, phenylmercuric borate, phenylmercuric nitrate, and thiomersal.

84. The method of claim 83, wherein the at least one microbicide is selected from ethyl, propyl, butyl and benzyl alcohol in a concentration of up to 10 w-%, chlorobutanol in the range between a concentration of 0.3-0.6 w-%; sorbic acid in the range between a concentration of 0.05-0.2 w %, benzoic acid in the range between a concentration of 0.1-0.5 w-%; and phenols and triclosan in the range between 0.1-0.3 w-%.

85. A method for controlling the flux of penetrants across an adaptable semi-permeable porous barrier, the method comprising the steps of:
preparing a formulation by suspending or dispersing said penetrants in a polar liquid, the penetrants comprising at least two kinds or forms of amphiphilic substances with a tendency to aggregate, wherein said at least two substances differ by at least a factor of 10 in solubility in said polar liquid, and wherein said penetrants are able to transport a drug agent through the pores of said baffler or enable drug agent permeation through the pores of said barner after the penetrants have entered the pores, the formulation further comprising a thickening agent;
selecting a dose amount of said penetrants to be applied on a predetermined area of said barrier to control the flux of said penetrants across said barrier; and applying said formulation containing the selected dose amount of said penetrants onto said area of said porous barrier, the formulation having a viscosity that enables retention of the drug agent at the area, wherein the less soluble amongst the aggregating substances is a lipid and the substance which is more soluble in the suspending liquid is a surfactant, and wherein the drug agent is a pevtide or a protein.

86. The method of claim 85 wherein the lipid is a polar lipid.

87. The method of claim 85, wherein the lipid is a lipid from a biological source or a corresponding synthetic lipid.

88. The method of claim 85, wherein the lipid belongs to a class of phospholipids corresponding to the general formula

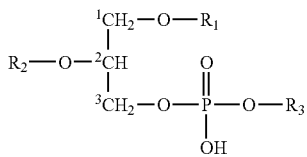

where $R_1$ and $R_2$ are aliphatic chains; and $R_3$ is hydrogen, 2-trimethylamino-1-ethyl, 2-amino-I-ethyl, $C_{1-4}$-alkyl, $C_{1-5}$-alkyl substituted with carboxy, $C_{2-5}$-alkyl substituted with hydroxy, $C_{2-5}$-alkyl substituted with carboxy and hydroxy, or $C_{2-5}$-alkyl substituted with carboxy and amino, inositol, sphingosine, or salts of said substances.

89. The method of claim 88, wherein the lipid is selected from glycerides, isoprenoid lipids, steroids, sterines or sterols of sulphur- or carbohydrate-containing lipids or other bilayer-forming lipids, phosphatidylcholines, phosphatidylethanolamines, phosphatidylglycerols, phosphatidylinositols, phosphatidic acids, phosphatidylserines, sphingomyelins or other sphingophospholipids, glycosphingolipids, gangliosides, glycolipids, and synthetic lipids.

90. The method of claim 89, wherein the glycosphingolipids are selected from cerebrosides, ceramidepolyhexosides, sulphatides, and sphingoplasmalogens.

91. The method of claim 88, wherein the lipids comprise two similar or different chains ester-groups-linked to the lipids' backbone or attached to the lipids' backbone with ether bonds.

92. The method of claim 88, wherein the lipid is selected from half-protonated fluid fatty acids.

93. The method of claim 88, wherein the aliphatic chain is a $C_{10-20}$-acyl, or -alkyl or partly unsaturated fatty acid residue.

94. The method of claim 88, wherein the aliphatic chain is an oleoyl-, palmitoleoyl-, elaidoyl-, linoleyl-, linolenyl-, linolenoyl-, arachidoyl-, vaccinyl-, lauroyl-, myristoyl-, palmitoyl-, or stearoyl chain.

95. The method of claim 85, wherein the surfactant is a nonionic surfactant, a zwitterionic surfactant, an anionic surfactant, a cationic surfactant, or a surface-active polypeptide.

96. The method of claim 85, wherein the surfactant is a fatty-acid or -alcohol, an alkyl-tri/di/methyl-ammonium salt, an alkylsulphate salt, a monovalent salt of cholate, deoxycholate, glycocholate, glycodeoxycholate, taurodeoxycholate, taurocholate, an acyl- or alkanoyl-dimethyl-aminoxide, an alkyl- or alkanoyl-N-methylglucamide, N-alkyl-N,N-dimethylglycine, 3-(acyldimethylammonio)-alkanesuiphonate, N-acyl-sulphobetaine, a polyethylene-glycol-octylphenyl ether, a polyethylene-acyl ether, a polyethyleneglycol-isoacyl ether or polyethylene-acyl ether, polyethylene-glycol-sorbitane-acyl ester, a polyhydroxyethylene-acyl ether or corresponding ester, a sorbitane-monoalkylate, an acyl- or alkanoyl-N-methylglucaniide, an alkyl-suiphate, sodium deoxycholate, sodium glycodeoxycholate, sodium oleate, sodium taurate, a fatty acid salt, a lysophospholipid, -phosphoryiglycerol, or -phosphorylserine, n-acyl-, a corresponding palmitoleoyl-, elaidoyl-, and vaccenyl-lysophospholipid, corresponding short-chain phospholipid, or surface-active polypeptide.

97. The method of claim 96, wherein the polyethylene-acyl ether is a nonaethylen-dodecyl ether; the polyethylene-glycol-sorbitane-acyl ester is selected from polyethylenglykol-20-monolaurate and polyethylenglykol-20-sorbitan-monooleate; the polyhydroxyethylene-acyl ether and corresponding esters are selected from polyhydroxyethylene-4 or 6 or 8 or 10 or 12, -lauryl ether, polyhydroxyethylen-8-stearate, -laurate or -oleate type, and polyethoxylated castor oil 40; the alkyl-sulphate is selected from lauryl- or oleoyl-sulphate; the fatty acid salt is selected from sodium elaidate, sodium linoleate, and sodium laurate; the lysophospholipid is oleoyl-glycerophosphatidic acid; and the phosphoryiglycerol or -phosphorylserine n-acyl- is selected from lauryl or oleoyl-glycero-phosphatidic acid, -phosphoryiglycorol, or -phosphorylserine, n-tetradecyl- glycero-phosphatidic acid, -phosphoryiglycerol, or -phosphorylserine.

98. The method of claim 85, wherein the surfactant is a dodecyl-dimethyl-aminoxide, a nonaethylene-glycol-octylphenyl ether, a octaethylene-glycol -isotridecyl ether, octaethylenedodecyl ether, polyhydroxyethylene-lauryl, -myristoyl, -cetylstearyl, or -oleoyl ether, sorbitane-monolaurate, decanoyl- or dodecanoyl-N-methylglucamide.

99. The method of claim 85, wherein the surfactant is polyethoxylated castor oil 40.

100. The method of claim 85, wherein the peptide or protein is insulin or serum albumin.

101. A method for increasing the flux of a penetrant across the skin or mucosa of a human or animal, the method comprising:
(a) applying a formulation onto a predetermined area of the skin or mucosa, the formulation comprising a penetrant, a polar liquid, and a thickening agent and having a viscosity that is 0.2 kN s/m$^2$ to 5 kN s/m$^2$ the penetrant (i) comprising a phosphatidyicholine and a surfactant and (ii) being capable of transporting a drug agent across the skin or mucosa, wherein the formulation is applied at a selected dose amount of the penetrant per area of the skin or mucosa of a human or animal, the formulation having a viscosity that enables retention of the drug agent at the area; and
(b) enlarging the applied dose amount of penetrant per area of the skin or mucosa of a human or animal,
wherein the drug agent is a peptide or a protein.

102. The method of claim 101, wherein the peptide or protein is insulin or serum albumin.

* * * * *

UNITED STATES PATENT AND TRADEMARK OFFICE
CERTIFICATE OF CORRECTION

| | | |
|---|---|---|
| PATENT NO. | : 7,591,949 B2 | Page 1 of 1 |
| APPLICATION NO. | : 10/984450 | |
| DATED | : September 22, 2009 | |
| INVENTOR(S) | : G. Cevc et al. | |

It is certified that error appears in the above-identified patent and that said Letters Patent is hereby corrected as shown below:

On the title page, item (63) should read as follows:

Related U.S. Application Data

(63) Continuation of application No. 10/037,480, filed on Jan. 4, 2002, which is a continuation of application No. PCT/EP00/06367, filed on Jul. 5, 2000, which is a continuation-in-part of application No. PCT/EP99/04659, filed on Jul. 5, 1999.

Signed and Sealed this

Tenth Day of November, 2009

David J. Kappos
*Director of the United States Patent and Trademark Office*